(12) United States Patent
Hsia et al.

(10) Patent No.: US 12,404,324 B2
(45) Date of Patent: *Sep. 2, 2025

(54) SAFE AND EFFECTIVE METHOD OF TREATING PSORIATIC ARTHRITIS WITH ANTI-IL23 SPECIFIC ANTIBODY

(71) Applicant: Janssen Biotech, Inc., Horsham, PA (US)

(72) Inventors: Elizabeth Hsia, Kennett Square, PA (US); Xie Xu, San Marcos, CA (US)

(73) Assignee: Janssen Biotech, Inc., Horsham, PA (US)

( * ) Notice: Subject to any disclaimer, the term of this patent is extended or adjusted under 35 U.S.C. 154(b) by 216 days.

This patent is subject to a terminal disclaimer.

(21) Appl. No.: 17/385,284

(22) Filed: Jul. 26, 2021

(65) Prior Publication Data

US 2021/0363235 A1    Nov. 25, 2021

Related U.S. Application Data

(63) Continuation of application No. 16/181,733, filed on Nov. 6, 2018, now abandoned.

(60) Provisional application No. 62/744,386, filed on Oct. 11, 2018, provisional application No. 62/581,996, filed on Nov. 6, 2017.

(51) Int. Cl.

| | | |
|---|---|---|
| *A61K 39/395* | (2006.01) | |
| *A61K 9/00* | (2006.01) | |
| *A61K 47/18* | (2017.01) | |
| *A61K 47/26* | (2006.01) | |
| *A61K 47/68* | (2017.01) | |
| *A61P 19/02* | (2006.01) | |
| *C07K 16/24* | (2006.01) | |
| *G16H 50/30* | (2018.01) | |
| *A61K 39/00* | (2006.01) | |

(52) U.S. Cl.
CPC .......... *C07K 16/244* (2013.01); *A61K 9/0019* (2013.01); *A61K 47/183* (2013.01); *A61K 47/26* (2013.01); *A61K 47/6849* (2017.08); *A61P 19/02* (2018.01); *G16H 50/30* (2018.01); *A61K 2039/505* (2013.01); *C07K 2317/21* (2013.01)

(58) Field of Classification Search
CPC .............. A61P 19/02; A61K 2039/505; C07K 2317/21
See application file for complete search history.

(56) References Cited

U.S. PATENT DOCUMENTS

| | | |
|---|---|---|
| 2011/0206680 A1 | 8/2011 | Valdes |
| 2015/0147337 A1 | 5/2015 | Reichert |
| 2018/0094052 A1 | 4/2018 | Randazzo |

FOREIGN PATENT DOCUMENTS

| | | |
|---|---|---|
| WO | 2014004436 | 1/2014 |
| WO | 2015119841 | 8/2015 |
| WO | 2017172771 | 10/2017 |
| WO | 2017180821 | 10/2017 |
| WO | 2018093841 | 5/2018 |

OTHER PUBLICATIONS

Clinical Trial NCT02319759 (v1, Dec. 18, 2014).*
Ungprasert et al. Indirect comparisons of the efficacy of biological agents in patients with psoriatic arthritis with an inadequate response to traditional disease-modifying anti-rheumatic drugs or to non-steroidal anti-inflammatory drugs: A meta-analysis. Semin Arthritis Rheum. Feb. 2016;45(4):428-38.*
Baeten, Dominique et al., "Secukinumab, an Interleukin-17A Inhibitor, in Ankylosing Spondylitis," The New England Journal of Medicine, vol. 373, issue 26 (Dec. 24, 2015) pp. 2534-2548.
Blauvelt, Andrew et al., "Efficacy and safety of guselkumab, an anti-interleukin-23 monoclonal antibody, compared with adalimumab for the continuous treatment of patients with moderate to severe psoriasis: Results from the phase III, double-blinded, placebo- and active comparator—controlled VOYAGE 1 trial", Journal of the American Academy of Dermatology, (Mar. 31, 2017), vol. 76, issue 3 (Mar. 17, 2017) pp. 405-417.
Bowes, John et al., "Confirmation of TNIP1 and IL23A as susceptibility loci for psoriatic arthritis," Annals of Rheumatological Diseases, vol. 70 (Apr. 24, 2011) pp. 1641-1644.
Brown, Alan , "Repository corticotropin injection in patients with refractory psoriatic arthritis: a case series," Open Access Rheumatology: Research and Reviews, vol. 2016, issue 8 (Nov. 11, 2016) pp. 97-102.
Coates, L.C., et al., "Defining minimal disease activity in psoriatic arthritis: a proposed objective target for treatment," Annals of Rheumatological Diseases, vol. 69 (Jan. 11, 2009) pp. 48-53.
Coates, Laura C. et al., "Group for Research and Assessment of Psoriasis and Psoriatic Arthritis/Outcome Measures in Rheumatology Consensus-Based Recommendations and Research Agenda for Use of Composite Measures and Treatment Targets in Psoriatic Arthritis," Arthritis & Rheumatology, vol. 70, issue 3 (Mar. 3, 2018) pp. 345-355.
Coates, Laura C. et al., "Validation of Minimal Disease Activity Criteria for Psoriatic Arthritis Using Interventional Trial Data," Arthritis Care & Research, vol. 62, issue 7 (Jul. 7, 2010) pp. 965-969.
Deodhar, Atul et al., "Efficacy and safety results of guselkumab in patients with active psoriatic arthritis over 56 weeks from a phase 2a, randomized, double-blind, placebo-controlled study," Arthritis and Rheumatic Diseases, vol. 391 (Jun. 2, 2018) pp. 2213-2224.

(Continued)

*Primary Examiner* — Dong Jiang
(74) *Attorney, Agent, or Firm* — Ice Miller LLP

(57) ABSTRACT

A method of treating psoriatic arthritis in a patient by administering an IL-23 specific antibody, e.g., guselkumab, in a clinically proven safe and clinically proven effective amount and the patient achieves significant ACR20/50/70, PASI70/90/100, MDA, HAQ-DI, SF-36 PCS, MCS, LEI/dactylitis, PASDAS, GRACE, mCPDAI, DAPSA or RAPID3 improvement as measured 16, 24, 32, 40 and 48 weeks after initial treatment.

41 Claims, 34 Drawing Sheets

Specification includes a Sequence Listing.

(56) References Cited

OTHER PUBLICATIONS

Duerr, Richard D. et al., "A Genome-Wide Association Study Identifies IL23R as an Inflammatory Bowel Disease Gene," Science, vol. 314, issue 5804 (Dec. 1, 2016) pp. 1461-1463.
Feagan, B. G. et al., "Ustekinumab as Induction and Maintenance Therapy for Crohn's Disease," The New England Journal of Medicine, vol. 375 (Nov. 17, 2016) pp. 1946-1960.
Feagan, Brian G. et al., "Induction therapy with the selective interleukin-23 inhibitor Risankizumab in patients with moderate-to-severe Crohn's disease: a randomized, double-blind, placebo-controlled phase 2 study," Lancet, vol. 389 (Apr. 29, 2017) pp. 1699-1709.
Gordon, K. B. et al., "Phase 3 Trials of Ixekizumab in Moderate-to-Severe Plaque Psoriasis," The New England Journal of Medicine, vol. 375, issue 4 (Jun. 8, 2016) pp. 345-356.
Helliwell, Philip S. et al. "Composite Disease Activity and Responder Indices for Psoriatic Arthritis: A Report from the GRAPPA 2013 Meeting on Development of Cutoffs for Both Disease Activity States and Response," The Journal of Rheumatology, vol. 41, issue 6 (2014) pp. 1212-1217.
Helliwell, Philip S. et al. "Radiographic Progression in Psoriatic Arthritis Achieving a Good Response to Treatment: Data Using Newer Composite Indices of Disease Activity," Arthritis Care & Research, vol. 70, No. 5 (May 2018) pp. 797-800.
Helliwell, Philip S. et al., "Comparison of Composite Measures of Disease Activity in Psoriatic Arthritis Using Data from an Interventional Study with Golimumab," Arthritis Care & Research, vol. 66, No. 5 (May 2014) pp. 749-756.
Her, Minyoung et al. "A review of disease activity measures for psoriatic arthritis: what is the best approach?" Expert Review of Clinical Immunology, vol. 10, No. 9, (Aug. 4, 2014) pp. 1241-1254.
Huber, Wolfgang et al., "Secukinumab, a human anti-IL-17A monoclonal antibody, for moderate to severe Crohn's disease: unexpected results of a randomized, double-blind placebo-controlled trial," Gut, vol. 61, issue 12 (Dec. 2012) pp. 1693-1700.
Krstic, Aleksandra et al., "The potential of interleukin-17 to mediate hematopoietic response," Immunology Research, vol. 52 (Mar. 4, 2012) pp. 34-41.
Langley, Richard G. et al., "Secukinumab in Plaque Psoriasis—Results of Two Phase 3 Trials," The New England Journal of Medicine, vol. 371, issue 4 (Jul. 24, 2014) pp. 326-338.
Lebwohl, M. et al., "Phase 3 Studies Comparing Brodalumab with Ustekinumab in Psoriasis," The New England Journal of Medicine, vol. 373, issue 14 (Oct. 1, 2015) pp. 1318-1328.
Leonardi, Craig L. et al., "Efficacy and safety of ustekinumab, a human interleukin-12/23 monoclonal antibody, in patients with psoriasis: 76-week results from a randomised, double-blind, placebo-controlled trial (Phoenix 1)," Lancet, vol. 371 (May 17, 2008) pp. 1665-1674.
Liu, Ying, et al. "A Genome-Wide Association Study of Psoriasis and Psoriatic Arthritis Identifies New Disease Loci," PLoS Genetics, vol. 4, issue 3 (May 2008) e1000041 pp. 1-14.
Lloyd, Peter et al., "Psoriatic arthritis: an update," Arthritis, vol. 2012 (Oct. 13, 2012) pp. 1-6.
Mease, P., "A short history of biological therapy for psoriatic arthritis," Clinical and Experimental Rheumatology, vol. 33, suppl. 93 (Sep. 25, 2015) pp. S104-S108.
Medical Phamplet for TALTZ (ixekizumab) injection, for subcutaneous use Initial U.S. Approval: 2016 (Revised May 2020).

Mumtaz, Aizad et al. "Development of a preliminary composite disease activity index in psoriatic arthritis," Annals of Rheumatological Disease, vol. 70, issue 2 (Apr. 1, 2011) pp. 272-277.
Nair, Rajan P. et al., "Genome-wide Scan Reveals Association of Psoriasis with IL-23 and NF-kappaB pathways," Nature Genetics, vol. 41, issue 2 (Sep. 16, 2009) pp. 199-204.
NCT02319759 on Jan. 26, 2015; "A Phase 2a, Multicenter, Randomized, Double-blind, Placebo-controlled Study Evaluating the Efficacy and Safety of Guselkumab in the Treatment of Subjects With Active Psoriatic Arthritis," (Jan. 26, 2015), pp. 1-3.
Olivieri, Ignazio et al., "Advances in the management of psoriatic arthritis," Nature Reviews Rheumatology, vol. 10, issue 9 (Jul. 8, 2014) pp. 531-542.
Orchard, T. R. et al., "Peripheral arthropathies in inflammatory bowel disease: their articular distribution and natural history," Gut, vol. 42, issue 3 (Mar. 1998) pp. 387-391.
Papp, Kim A. et al., "Efficacy and safety of ustekinumab, a human interleukin-12/23 monoclonal antibody, in patients with psoriasis: 52-week results from a randomised, double-blind, placebo-controlled trial (Phoenix 2)," Lancet, vol. 371 (May 17, 2008) pp. 1675-1684.
Rahman, Proton et al., "Association of Interleukin-23 Receptor Variants with Ankylosing Spondylitis," Arthritis & Rheumatism, vol. 58, issue 4 (Apr. 2008) pp. 1020-1025.
Reich, Kristian et al., "Efficacy and safety of guselkumab, an anti-interleukin-23 monoclonal antibody, compared with adalimumab for the treatment of patients with moderate to severe psoriasis with randomized withdrawal and retreatment: Results from the phase III, double-blind, placebo- and active comparator-controlled VOYA", Journal of the American Academy of Dermatology, vol. 76, No. 3 (Jan. 2, 2017) pp. 418-431.
Sands, Bruce E, et al., "Efficacy and Safety of MEDI2070, an Antibody Against Interleukin 23, in Patients with Moderate to Severe Crohn's Disease: A Phase 2a Study," Gastroenterology, vol. 153, No. 1 (2017) pp. 77-86.
Scher, Jose U. et al., "Decreased Bacterial Diversity Characterizes an Altered Gut Microbiota in Psoriatic Arthritis and Resembles Dysbiosis of Inflammatory Bowel Disease," Arthritis & Rheumatology, vol. 67, issue 1 (Jan. 2015) pp. 128-139.
Schoels, Monika M. et al., "Disease activity in psoriatic arthritis (PsA): defining remission and treatment success using the DAPSA score," Annals of Rheumatological Diseases, vol. 75, issue 5 (Aug. 12, 2015) pp. 811-818.
Targan, Stephan R. et al., "A Randomized, Double-Blind, Placebo-Controlled Phase 2 Study of Brodalumab in Patients with Moderate-to-Severe Crohn's Disease," American Journal of Gastroenterology, vol. 111, issue 11 (Nov. 2016) pp. 1599-1607.
Taylor, William et al., "Classification Criteria for Psoriatic Arthritis," Arthritis & Rheumatism, vol. 54, issue 8 (Aug. 2006) pp. 2665-2673.
Nakamura et al., "Guselkumab for the Treatment of Psoriasis: A Review of Phase III Trials," Dermatology and Therapy (2017), vol. 7, pp. 281-292.
Gossec, L. et al., "European League Against Rheumatism (EULAR) recommendations for the management of psoriatic arthritis with pharmacological therapies: 2015 update," Annals of Rheumatological Diseases (2016), vol. 75, pp. 499-510.
Coates, L.C. et al., " Group for Research and Assessment of Psoriasis and Psoriatic Arthritis 2015 Treatment Recommendations for Psoriatic Arthritis ," Arthritis & Rheumatology (2016), vol. 68, No. 5, pp. 1060-1071.

* cited by examiner p-values are based on Cochran-Mantel-Haenszel test.
Patients with dactylitis assessed based on imputed values with EE and missing data rules applied.

Patients within dactylitis subset who did not EE and continued at Week 24 – observed data.

SAFE AND EFFECTIVE METHOD OF TREATING PSORIATIC ARTHRITIS WITH ANTI-IL23 SPECIFIC ANTIBODY

CROSS-REFERENCE TO RELATED APPLICATIONS

This application is a Continuation of U.S. patent application Ser. No. 16/181,733, filed 6 Nov. 2018, currently pending, which claims the benefit of U.S. Provisional Application Ser. No. 62/581,996, filed 6 Nov. 2017, and U.S. Provisional Application Ser. No. 62/744,386, filed 11 Oct. 2018. The entire contents of the aforementioned applications are incorporated herein by reference in their entireties.

SEQUENCE LISTING

The instant application contains a Sequence Listing which has been submitted electronically in ASCII format and is hereby incorporated by reference in its entirety. Said ASCII copy, created on 22 Jul. 2021, is named JBI5144U-SCNT1SEQLIST.txt and is 78 kilobytes in size.

FIELD OF THE INVENTION

The present invention concerns methods for treating psoriatic arthritis with an antibody that binds the human IL-23 protein. In particular, it relates to a method of administering an anti-IL-23 specific antibody and specific pharmaceutical compositions of an antibody, e.g., guselkumab, which is safe and effective for patients suffering from psoriatic arthritis.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell. IL-12 signaling concurrent with antigen presentation is thought to invoke T cell differentiation towards the T helper 1 (Th1) phenotype, characterized by interferon gamma (IFNγ) production. Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23. IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells. Recent studies have demonstrated that the biological functions of IL-23 are distinct from those of IL-12, despite the structural similarity between the two cytokines.

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis. However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Studies have confirmed through IL-23p19 deficient mice or specific antibody neutralization of IL-23 that IL-23 inhibition can provide equivalent benefit as anti-IL-12p40 strategies. Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over current therapeutic options.

Psoriasis is a common, chronic immune-mediated skin disorder with significant co-morbidities, such as psoriatic arthritis (PsA), depression, cardiovascular disease, hypertension, obesity, diabetes, metabolic syndrome, and Crohn's disease. Plaque psoriasis is the most common form of the disease and manifests in well demarcated erythematous lesions topped with white silver scales. Plaques are pruritic, painful, often disfiguring and disabling, and a significant proportion of psoriatic patients have plaques on hands/nails face, feet and genitalia. As such, psoriasis negatively impacts health-related quality of life (HRQoL) to a significant extent, including imposing physical and psychosocial burdens that extend beyond the physical dermatological symptoms and interfere with everyday activities. For example, psoriasis negatively impacts familial, spousal, social, and work relationships, and is associated with a higher incidence of depression and increased suicidal tendencies.

Psoriatic arthritis (PsA) is a multi-system disease characterized by joint inflammation and psoriasis, with diverse clinical and radiographic manifestations including dactylitis, enthesitis, sacroiliitis, and/or joint deformity. Functional impairment, decreased quality of life, and increased healthcare resource utilization associated with poorly-controlled PsA present significant economic burden. Despite availability of biologics (e.g., tumor-necrosis-factor [TNF]α inhibitors, ustekinumab, secukinumab), and other agents (e.g., apremilast), significant unmet needs exist for new PsA therapies that can provide high levels of efficacy and safety in treating heterogeneous disease components Histologic characterization of psoriasis lesions reveals a thickened epidermis resulting from aberrant keratinocyte proliferation and differentiation as well as dermal infiltration and co-localization of CD3+ T lymphocytes and dendritic cells. While the etiology of psoriasis is not well defined, gene and protein analysis have shown that IL-12, IL-23 and their downstream molecules are over-expressed in psoriatic lesions, and some may correlate with psoriasis disease severity. Some therapies used in the treatment of psoriasis modulate IL-12 and IL-23 levels, which is speculated to contribute to their efficacy. Th1 and Th17 cells can produce effector cytokines that induce the production of vasodilators, chemoattractants and expression of adhesion molecules on endothelial cells which in turn, promote monocyte and neutrophil recruitment, T cell infiltration, neovascularization and keratinocyte activation and hyperplasia. Activated keratinocytes can produce chemoattractant factors that promote neutrophil, monocyte, T cell, and dendritic cell trafficking, thus establishing a cycle of inflammation and keratinocyte hyperproliferation.

Elucidation of the pathogenesis of psoriasis has led to effective biologic treatments targeting tumor necrosis factor-alpha (TNF-α), both interleukin (IL)-12 and IL-23 and, most recently, IL-17 as well as IL-23 alone (including in Phase 1 and 2 clinical trials using guselkumab). Guselkumab (also known as CNTO 1959) is a fully human IgG1 lambda monoclonal antibody that binds to the p19 subunit of IL-23 and inhibits the intracellular and downstream signaling of IL-23, required for terminal differentiation of T helper (Th)17 cells. Biologics targeting IL-12/23 or the downstream IL-17 or IL-17R (e.g., ustekinumab, secukinumab, ixekizumab, brodalumab) have consistently demonstrated robust efficacy in phase-2/3 psoriasis/PsA trials.

SUMMARY OF THE INVENTION

In a first aspect, the invention concerns a method of treating psoriastic arthritis in a patient comprising subcutaneously administering an anti-IL-23 specific antibody (also referred to as IL-23p19 antibody), e.g., guselkumab, to the patient, wherein the anti-IL-23 specific antibody is administered at an initial dose, a dose 4 weeks thereafter, and at a dosing interval of once every 8 weeks thereafter, e.g., a dose at 0, 4, 8, 16, 24, 32, 40 and 48 weeks.

In another aspect, the composition used in the method of the invention comprises a pharmaceutical composition comprising: an anti-IL-23 specific antibody in an amount from about 1.0 µg/ml to about 1000 mg/ml, specifically at 50 mg or 100 mg. In a preferred embodiment, the anti-IL-23 specific antibody is guselkumab at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In an embodiment of the method of the invention, PsA patients achieved significant improvement in ACR20 response for guselkumab vs. placebo by week 24 (58% vs 18.4% of guselkumab vs. placebo-treated patients) and consistently higher ACR50 and ACR70 responses over time through week 24.

In another aspect of the invention, the pharmaceutical composition comprises an isolated anti-IL23 specific antibody having the guselkumab CDR sequences comprising (i) the heavy chain CDR amino acid sequences of SEQ ID NO: 5, SEQ ID NO: 20, and SEQ ID NO: 44; and (ii) the light chain CDR amino acid sequences of SEQ ID NO: 50, SEQ ID NO: 56, and SEQ ID NO: 73 at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

Another aspect of the method of the invention comprises administering a pharmaceutical composition comprising an isolated anti-IL-23 specific antibody having the guselkumab heavy chain variable region amino acid sequence of SEQ ID NO: 106 and the guselkumab light chain variable region amino acid sequence of SEQ ID NO: 116 at 100 mg/mL; 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

BRIEF DESCRIPTION OF THE DRAWINGS

FIGS. 3A-J. Show proportions of patients achieving MDA (3A) and VLDA (3B) at Week 16 and Week 24 (full analysis set; NRI) and proportions of patients achieving disease activity states, and mean changes from baseline at Week 16 and Week 24 for PASDAS (3C, 3D), GRACE (3E, 3F), mCPDAI (3G, 3H), and DAPSA (3I, 3J) PsA-specific composite endpoints (full analysis set; last observation carried forward for missing data). DAPSA=Disease Activity Index for PSoriatic Arthritis, GRACE=Group for Research and Assessment of Psoriasis and Psoriatic Arthritis (GRAppa) Composite scorE, mCPDAI=modified Composite Psoriatic Disease Activity Index, MDA=minimal disease activity, NRI=nonresponder imputation, PASDAS—Psoriatic ArthritiS Disease Activity Score, PsA=psoriatic arthritis, VLDA=very low disease activity.

DETAILED DESCRIPTION OF THE PREFERRED EMBODIMENTS

Figure 1:
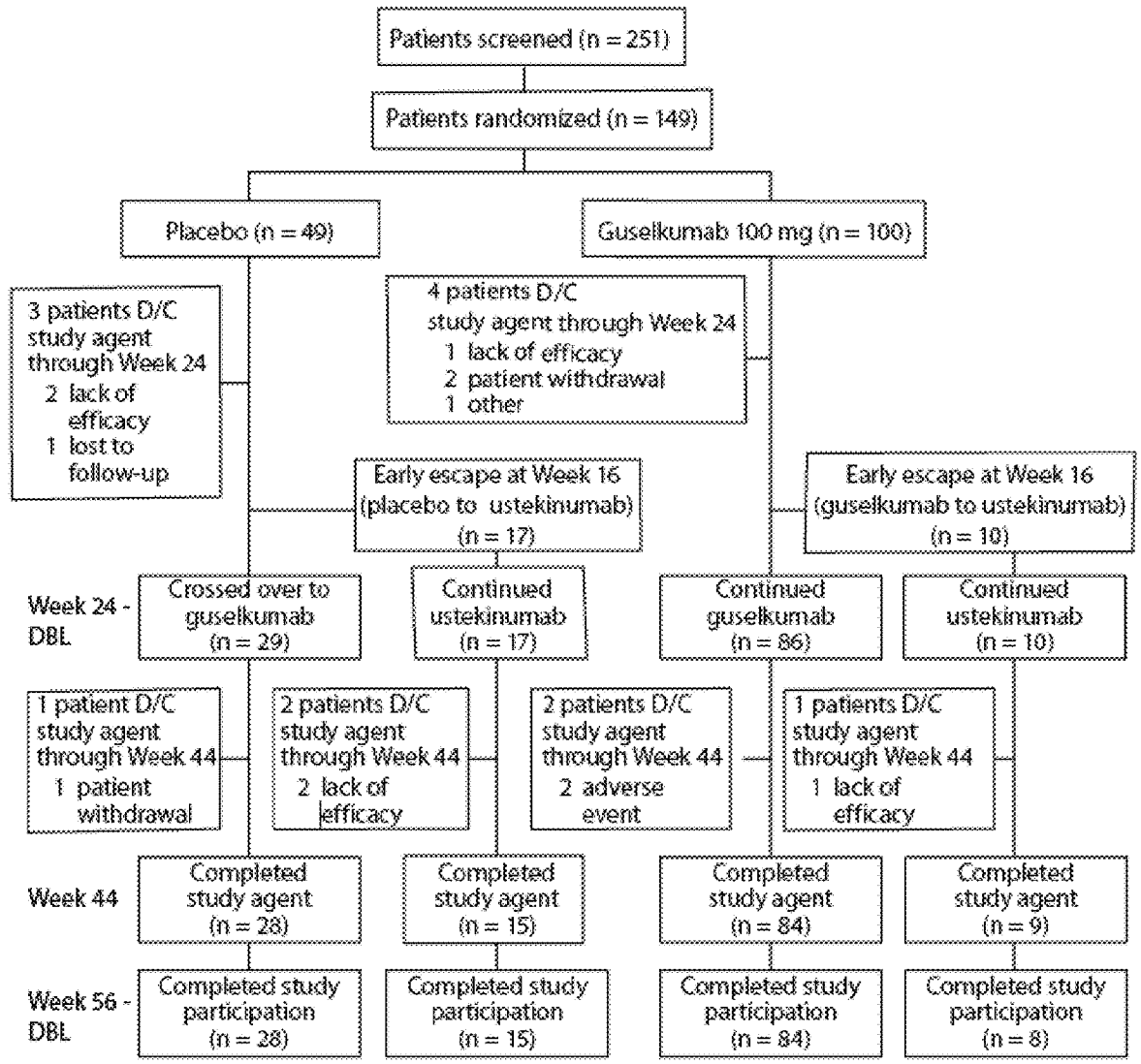
FIG. 1. Shows a Schematic Overview of the Trial Study. Note that one patient who completed 44 weeks of treatment with the study drug was lost to follow-up and did not attend the week 56 follow-up visit.

As used herein the method of treatment of psoriasis comprises administering isolated, recombinant and/or synthetic anti-IL-23 specific human antibodies and diagnostic and therapeutic compositions, methods and devices.

As used herein, an "anti-IL-23 specific antibody," "anti-IL-23 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23 antibody, specified portion or variant of the present invention can bind at least one IL-23 molecule, or specified portions, variants or domains thereof. A suitable anti-IL-23 antibody, specified portion, or variant can also optionally affect at least one of IL-23 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-23. For example, antibody fragments capable of binding to IL-23 or portions thereof, including, but not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos.

6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-23 specific (also termed IL-23 specific antibodies) (or antibodies to IL-23) useful in the methods and compositions of the present invention can optionally be characterized by high affinity binding to IL-23 and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344: 1125-1127 (1994), entirely incorporated herein by reference). "Low immunogenicity" can also be defined as the incidence of titrable levels of antibodies to the anti-IL-23 antibody in patients treated with anti-IL-23 antibody as occurring in less than 25% of patients treated, preferably, in less than 10% of patients treated with the recommended dose for the recommended course of therapy during the treatment period.

The terms "clinically proven efficacy" and "clinically proven effective" as used herein in the context of a dose, dosage regimen, treatment or method refer to the clinically proven effectiveness of a particular dose, dosage or treatment regimen. Efficacy can be measured based on change in the course of the disease in response to an agent of the present invention based on the clinical trials conducted, e.g., Phase 2 clinical trials and earlier. For example, an anti-IL-23 antibody of the present invention (e.g., the anti-IL-23 antibody guselkumab) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, an anti-IL-23 antibody of the present invention may be administered to achieve an improvement in a patient's condition related to psoriatic arthritis. Improvement may be indicated by an improvement in an index of disease activity, by amelioration of clinical symptoms or by any other measure of disease activity. One such index of disease is the ACR 20% improvement criteria (ACR20). Also, the Psoriasis Area and Severity Index (PAST) is an index of disease used to assess skin disease severity/extent, e.g., PASI75=75% improvement, PASI90=90% improvement and PASI100= substantially cleared of plaques. The measure of efficacy can also comprise HAQ-DI, enthesitis/dactylitis improvements in patients with baseline enthesitis/dactylitis, changes in SF-36 mental and physical component summary (MCS and PCS) scores, and achievement of minimal disease activity (MDA) criteria score.

The term "clinically proven safe," as it relates to a dose, dosage regimen, treatment or method with an anti-IL-23 antibody of the present invention (e.g., the anti-IL-23 antibody guselkumab), refers to a relatively low or reduced frequency and/or low or reduced severity of treatment-emergent adverse events (referred to as AEs or TEAEs) from the clinical trials conducted, e.g., Phase 2 clinical trials and earlier, compared to the standard of care or to another comparator. An adverse event is an untoward medical occurrence in a patient administered a medicinal product. In particular, clinically proven safe as it relates to a dose, dosage regimen or treatment with an anti-IL-23 antibody of the present invention refers to a relatively low or reduced frequency and/or low or reduced severity of adverse events associated with administration of the antibody if attribution is considered to be possible, probable, or very likely due to the use of the anti-IL-23 antibody.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMEA or a corresponding national regulatory agency. For example, the clinical study may be an adequately sized, randomized, double-blinded study used to clinically prove the effects of the drug.

Utility

The isolated nucleic acids of the present invention can be used for production of at least one anti-IL-23 antibody or specified variant thereof, which can be used to measure or effect in a cell, tissue, organ or animal (including mammals and humans), to diagnose, monitor, modulate, treat, alleviate, help prevent the incidence of, or reduce the symptoms of psoriasis.

Such a method can comprise administering an effective amount of a composition or a pharmaceutical composition comprising at least one anti-IL-23 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

Citations

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, 2$^{nd}$ Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention—Production and Generation

At least one anti-IL-23 antibody used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, 2$^{nd}$ Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

A preferred anti-IL-23 antibody is guselkumab (also referred to as CNTO1959) having the heavy chain variable region amino acid sequence of SEQ ID NO: 106 and the light chain variable region amino acid sequence of SEQ ID NO: 116 and having the heavy chain CDR amino acid sequences of SEQ ID NO: 5, SEQ ID NO: 20, and SEQ ID NO: 44; and the light chain CDR amino acid sequences of SEQ ID NO: 50, SEQ ID NO: 56, and SEQ ID NO: 73. Other anti-IL-23 antibodies have sequences listed herein and are described in U.S. Pat. No. 7,935,344, the entire contents of which are incorporated herein by reference).

Human antibodies that are specific for human IL-23 proteins or fragments thereof can be raised against an appropriate immunogenic antigen, such as an isolated IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NS0, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsried/Planegg, DE; Biovation, Aberdeen, Scotland, UK; BioInvent, Lund, Sweden; Dyax Corp., Enzon, Affymax/Biosite; Xoma, Berkeley, CA; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, MA; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/online-comp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human IL-23 specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human IL-23 specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively, or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human IL-23 specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human IL-23 (or anti-IL-23) antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human IL-23 specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human IL-23 specific antibody of the present invention is expressed in cells that express beta (1,4)-N-acetylglucosaminyltransferase III (GnT III), such that GnT III adds GlcNAc to the human IL-23 antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The anti-IL-23 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-23 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, CA), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL23 antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873, 316; 5,849,992; 5,994,616; 5,565,362; 5,304,489, and the like, each of which is entirely incorporated herein by reference.

Antibodies used in the method of the present invention can additionally be prepared using at least one anti-IL23 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-23 with a wide range of affinities ($K_D$). In a preferred embodiment, a human mAb can optionally bind human IL-23 with high affinity. For example, a human mAb can bind human IL-23 with a $K_D$ equal to or less than about $10^{-7}$M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, NY (1984); Kuby, Janis Immunology, W. H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one anti-IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-23 antibody or variable region; and nucleic acid molecules which comprise a nucleotide sequence substantially different from those described above but which, due to the degeneracy of the genetic code, still encode at least one anti-IL-23 antibody as described herein and/or as known in the art. Of course, the genetic code is well known in the art. Thus, it would be routine for one skilled in the art to generate such degenerate nucleic acid variants that code for specific anti-IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, CA (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenylation or transcription terminator sequences are typically incorporated into the vector. An example of a terminator sequence is the polyadenylation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23 Antibodies.

An anti-IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-23 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to the IL-23 receptor or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-23 antibody to inhibit an IL-23-dependent activity is preferably assessed by at least one suitable IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other transgenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-23 specific antibody can comprise at least one of a heavy or light chain variable region having a defined amino acid sequence. For example, in a preferred embodiment, the anti-IL-23 antibody comprises at least one of at least one heavy chain variable region, optionally having the amino acid sequence of SEQ ID NO:106 and/or at least one light chain variable region, optionally having the amino acid sequence of SEQ ID NO:116. Antibodies that bind to human IL-23 and that comprise a defined heavy or light chain variable region can be prepared using suitable methods, such as phage display (Katsube, Y., et al., *Int J Mol. Med,* 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-23 with high affinity (e.g., $K_D$ less than or equal to about $10^{-9}$M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-23 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

Anti-IL-23 antibodies can include, but are not limited to, at least one portion, sequence or combination selected from 5 to all of the contiguous amino acids of at least one of SEQ ID NOS: 5, 20, 44, 50, 56, and 73.

IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-23 antibody can further optionally comprise a polypeptide of at least one of 70-100% of 5, 17, 10, 11, 7, 9, 119, or 108 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences.

"Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, MD).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following:
(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)

Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

$n_n \le x_n - (x_n \cdot y)$, wherein $n_n$ is the number of nucleotide alterations, $x_n$ is the total number of nucleotides in sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or:

n.sub.a.ltorsim.x.sub.a−(x.sub.a.y),
wherein n.sub.a is the number of amino acid alterations, x.sub.a is the total number of amino acids in the SEQ ID NOs above, and y is, for instance 0.70 for 70%, 0.80 for 80%, 0.85 for 85% etc., and wherein any non-integer produce of x.sub.a and y is rounded down to the nearest integer prior to subtracting it from x.sub.a.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphoramide linkages. Suitable methods to introduce activating groups into molecules are known in the art (see for example, Hermanson, G. T., *Bioconjugate Techniques*, Academic Press: San Diego, CA (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Bocdiaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, CA (1996).

The method of the present invention also uses an anti-IL-23 antibody composition comprising at least one, at least two, at least three, at least four, at least five, at least six or more anti-IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-23 antibody amino acid sequence selected from the group consisting of 70-100% of the contiguous amino acids of the SEQ ID NOs above, or specified fragments, domains or variants thereof. Preferred anti-IL-23 antibody compositions include at least one or two full length, fragments, domains or variants as at least one CDR or LBP containing portions of the anti-IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, PA, 2001; Health Professional's Drug Guide 2001, ed., Shannon, Wilson, Stang, Prentice-Hall, Inc, Upper Saddle River, NJ; Pharmacotherapy Handbook, Wells et al., ed., Appleton & Lange, Stamford, CT, each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook.)

Anti-IL-23 antibody compositions can further comprise at least one of any suitable and effective amount of a composition or pharmaceutical composition comprising at least one anti-IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, 2$^{nd}$ Edition, Appleton and Lange, Stamford, CT (2000); PDR Pharmacopoeia, Tarascon Pocket Pharmacopoeia 2000, Deluxe Edition, Tarascon Publishing, Loma Linda, CA (2000), each of which references are entirely incorporated herein by reference.

Anti-IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18$^{th}$ Edition, Mack Publishing Co. (Easton, PA) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23 antibody, portion or variant compositions according to the invention are known in the art, e.g., as listed in "Remington: The Science & Practice of Pharmacy," 19$^{th}$ ed., Williams & Williams, (1995), and in the "Physician's Desk Reference," 52$^{nd}$ ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-23 specific antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-23 specific antibody, and a second vial comprising an aqueous diluent of prescribed buffer or preservative, wherein said packaging material comprises a label that instructs a patient to reconstitute the anti-IL-23 specific antibody in the aqueous diluent to form a solution that can be held over a period of twenty-four hours or greater.

The anti-IL-23 specific antibody used in accordance with the present invention can be produced by recombinant means, including from mammalian cell or transgenic preparations, or can be purified from other biological sources, as described herein or as known in the art.

The range of the anti-IL-23 specific antibody includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyols, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-23 specific antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23 specific antibody and preservative in an aqueous diluent is carried out using conventional dissolution and mixing procedures. To prepare a suitable formulation, for example, a measured amount of at least one anti-IL-23 specific antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, MN, www.mediject.com), and similarly suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-23 specific mAbs bind to similar or different epitopes and/or compete with each other. Abs are individually coated on ELISA plates. Competing mAbs are added, followed by the addition of biotinylated hrIL-23. For positive control, the same mAb for coating may be used as the competing mAb ("self-competition"). IL-23 binding is detected using streptavidin. These results demonstrate whether the mAbs recognize similar or partially overlapping epitopes on IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(epsilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(epsilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating psoriasis, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etanacept (Enbrel™), adalimumab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, CT (2000); PDR Pharmacopoeia, Tarascon Pocket Pharmacopoeia 2000, Deluxe Edition, Tarascon Publishing, Loma Linda, C A (2000); Nursing 2001 Handbook of Drugs, 21st edition, Springhouse Corp., Springhouse, P A, 2001; Health Professional's Drug Guide 2001, ed., Shannon, Wilson, Stang, Prentice-Hall, Inc, Upper Saddle River, NJ, each of which references are entirely incorporated herein by reference.

Therapeutic Treatments

Typically, treatment of psoriatic arthritis is affected by administering an effective amount or dosage of an anti-IL-23 antibody composition that total, on average, a range from at least about 0.01 to 500 milligrams of an anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 19, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-23 specific antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EXAMPLES

Materials and Methods

Patients

The trial enrolled patients aged ≥18 years with PsA for ≥6 months, fulfilling Classification Criteria for Psoriatic Arthritis (CASPAR); (Taylor W. et al. Arthritis Rheum 2006, 54: 2665-73) ≥3 tender and ≥3 swollen joints, C-reactive protein [CRP]≥0.3 mg/dL, ≥3% body surface area (BSA) of plaque psoriasis; and inadequate response to standard therapies (≥3 months of non-biologic disease modifying anti-rheumatic drugs [DMARDs]; ≥4 weeks of oral corticosteroids or nonsteroidal anti-inflammatory drugs [NSAIDs]); or intolerance of such therapies) were eligible. Patients with one prior anti-TNFα agent were permitted, but limited to 20% of participants, following 8-12 weeks of washout. Patients were ineligible if they had a history or current signs of severe, progressive, or uncontrolled medical conditions or had current or history of malignancy within 5 years, except nonmelanoma skin cancer (NMSC). Patients with history or symptoms of active tuberculosis (TB) were excluded. Patients could not participate if they had received guselkumab or adalimumab previously; other anti-TNF-α therapy within 3 months; other treatment targeting IL-12/23, IL-17, or IL-23 within 6 months; or any systemic immunosuppressants (e.g., methotrexate) or phototherapy within 4 weeks.

Study Design

The study was a double-blind, placebo-controlled study conducted at 34 sites in seven countries (Canada, Germany, Poland, Romania, Russia, Spain, United States) from Mar. 27, 2015-Jan. 17, 2017. Patients were randomized 2:1 (stratified by prior anti-TNFα use) to receive subcutaneous guselkumab 100 mg or placebo at Week0, Week4, and every 8 weeks (q8 w). This dose regimen was selected based on the dose-response in psoriasis, where a higher dose (200 mg q12 w) did not yield incremental benefit.

At Week16, all patients with <5% improvement in swollen and tender joint counts were eligible for early-escape to open-label ustekinumab (placebo→ustekinumab, guselkumab→ustekinumab). Patients continuing placebo crossed over to receive guselkumab 100 mg (placebo→guselkumab) at Week24, Week28, and q8 w through Week44 with a final follow-up at Week56. MTX (≤25 mg/week), oral corticosteroids (≤10 mg/day of prednisone/equivalent), and NSAIDs were permitted but not required; with stable doses through Week24. Sulfasalazine (≤3 g/day) and leflunomide (≤20 mg/day) were permitted post-Week24. Other DMARDs and biologics were prohibited through Week56.

This trial (NCT02319759) was conducted per Declaration of Helsinki and Good Clinical Practice guidelines. The protocol (available at NEJM.org) was approved by governing ethical bodies; patients provided written informed consent. Janssen Research & Development, LLC funded the study and analyzed data (BD/YW/YZ/WB/XLX). All authors interpreted the data and collaborated on manuscript preparation, supported by a Janssen-funded medical writer. All authors decided to submit the manuscript for publication and attest to data veracity/completeness and study fidelity to the protocol.

An institutional review board or ethics committee approved the study protocol at participating sites; patients provided written informed consent before study initiation.

Assessments

Independent assessors evaluated joints for tenderness (N=68) and swelling (N=66, excluding hips). Patients reported pain (0-100 mm visual analog scale [VAS]), global disease activity (0-100 mm VAS), and physical function (Health Assessment Questionnaire-Disability Index [HAQ-DI]). Investigators completed the global assessment of disease activity (0-100 mm VAS), and serum CRP was determined. The joint assessor also assessed dactylitis severity for each finger/toe on a scale of 0 (no dactylitis) to 3 (severe dactylitis), with a total score of 0-60, and the presence of enthesitis using the Leeds Enthesitis Index (LEI).

The Psoriasis Area and Severity Index (PAST) assessed skin disease severity/extent. The 36-item Short-Form (SF-36) Health Survey assessed mental and physical health and quality of life. The primary endpoint was the proportion of patients meeting the ACR 20% improvement criteria (ACR20) at Week24. Secondary endpoints included ACR20 at Week16; and PASI75/90/100, ACR50/70, HAQ-DI, enthesitis/dactylitis improvements in patients with baseline enthesitis/dactylitis, changes in SF-36 mental and physical component summary (MCS and PCS) scores, and achievement of minimal disease activity (MDA) criteria through Week56. Adverse events (AEs) were monitored.

Statistical Analyses

Efficacy analyses through Week24 employed the modified Intent-to-Treat population (mITT or Full Analysis Set; randomized and treated patients). Treatment group comparisons employed the Cochran-Mantel-Haenszel test stratified by prior TNFα-inhibitor use for binary endpoints and a mixed model for repeated measures, analysis of variance, or Wilcoxon rank sum test for continuous endpoints. To control type I error for multiplicity, two secondary analyses at Week24 (PASI75, HAQ-DI change) were to be performed sequentially, contingent upon primary analysis/preceding hypothesis success ($\alpha=0.05$; 2-sided). Further analytical details are provided online.

Data handling rules were applied to all efficacy analyses through Week24. Patients who met treatment-failure criteria, early-escaped, or had missing data were considered nonresponders for dichotomous ACR/MDA responses after treatment-failure/early-escape through Week24. For continuous endpoints through Week24, patients with missing baseline were excluded. Last-observation-carried-forward methodology was employed to impute post-baseline missing data or data post-early-escape. ACR/MDA responses through Week56 also were analyzed post-hoc in the mITT population using nonresponder imputation (NRI) for treatment-failure, early-escape, or missing data.

Results

Patients

Among 251 screened patients, 149 were randomized to placebo (N=49) or guselkumab (N=100). Seventeen (34.7%) placebo- and 10 (10.0%) guselkumab-treated patients qualified for early-escape to ustekinumab at Week16. Three (6.1%) patients receiving placebo, 1 (3.4%) receiving placebo→guselkumab, and 6 (6.0%) in the guselkumab group discontinued study agent through Week44 (FIG. 1).

Baseline characteristics were generally similar between groups and indicated moderate-to-severe arthritis. Mean BSA/PASI scores appeared somewhat higher with guselkumab vs. placebo, and more patients in the guselkumab vs. placebo groups had baseline dactylitis/enthesitis, although no difference was statistically significant. Most (87.9%) patients had previously received conventional DMARDs; 44.3% were receiving MTX at baseline; and 8.7% previously received an anti-TNFα agent (Table 1).

Efficacy During Placebo-Controlled Period (Week 0-24)

Figure 2A:
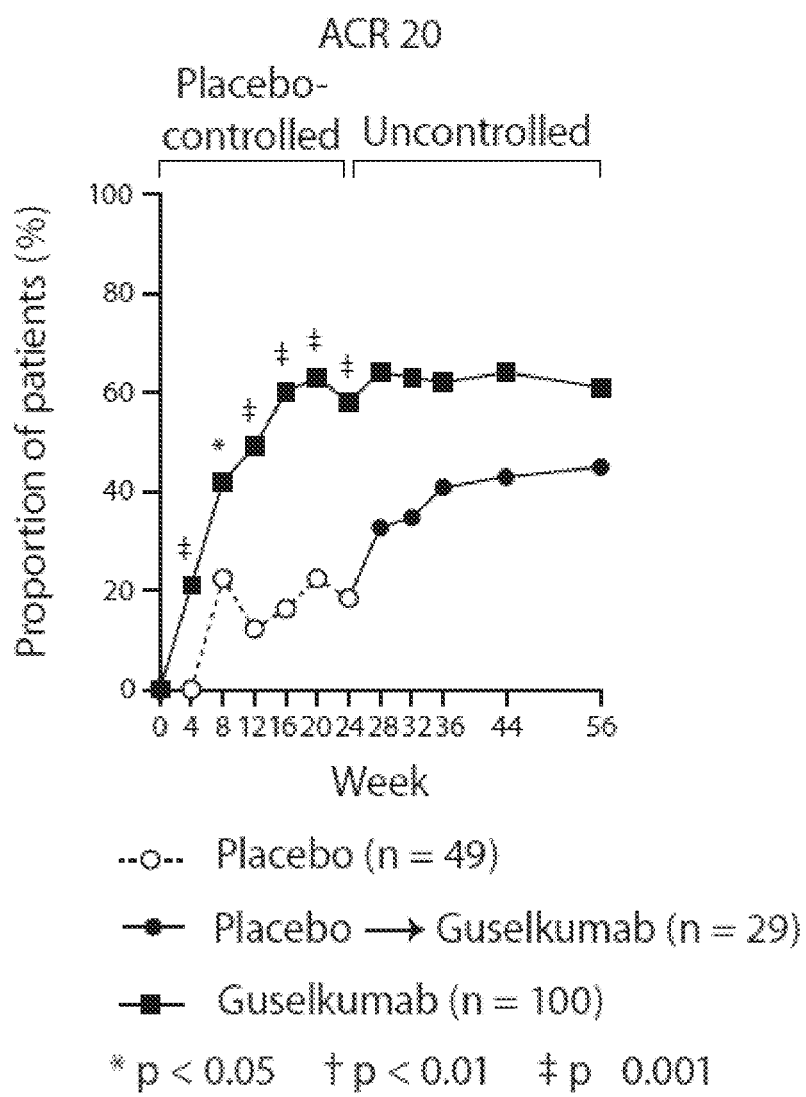
FIGS. 2A-D. Show the proportions of patients achieving ACR20 (2A), ACR50 (2B), ACR70 (2C), and Minimal Disease Activity, MDA (2D) responses over time, in the modified intention-to-treat (mITT/FAS) population using NRI for treatment-failures, early-escape, and missing data. P values derived from CMH testing. P values for ACR50 (other than Week24), ACR70 and MDA at Week16 were calculated post-hoc. ACR20/50/70—American College of Rheumatology 20/50/70% improvement=proportion of patients with at least 20%, 50%, and 70% improvement in signs or symptoms of psoriatic arthritis, according to ACR criteria, CMH—Cochran-Mantel-Haenszel, MDA—minimal disease activity, FAS—full analyses set, mITT—modified intent-to-treat.
Figure 2B:
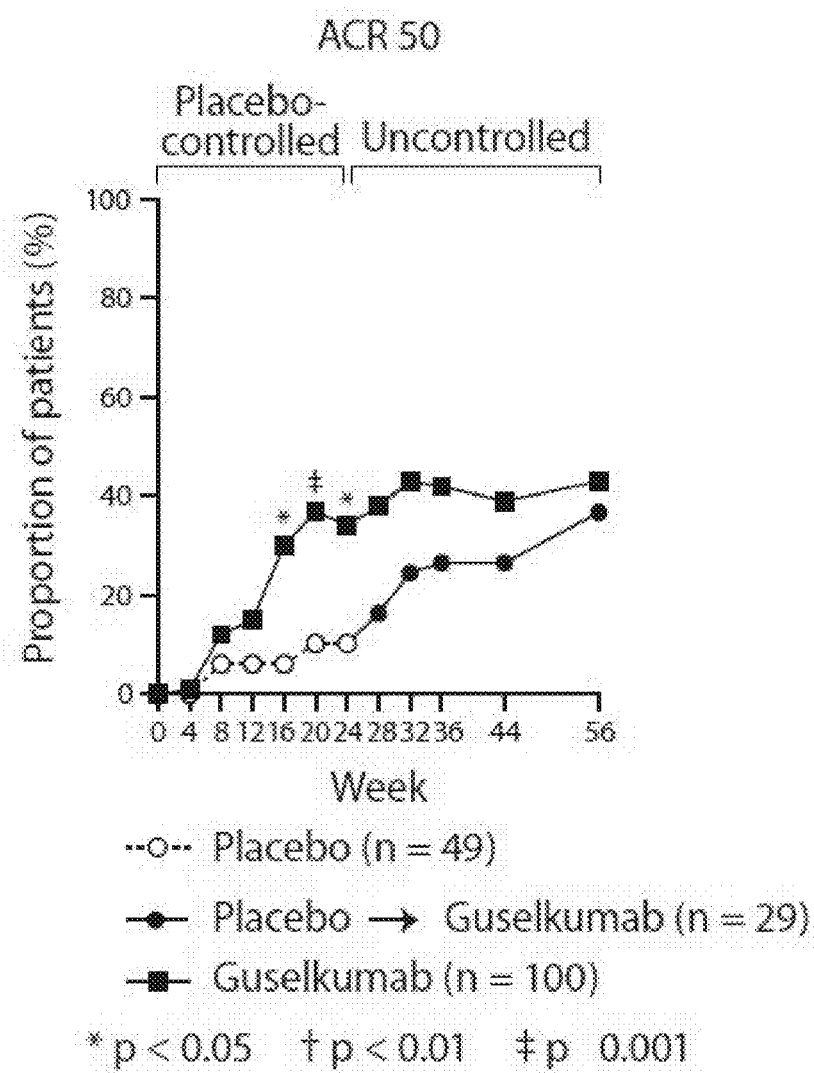
Figure 2C:
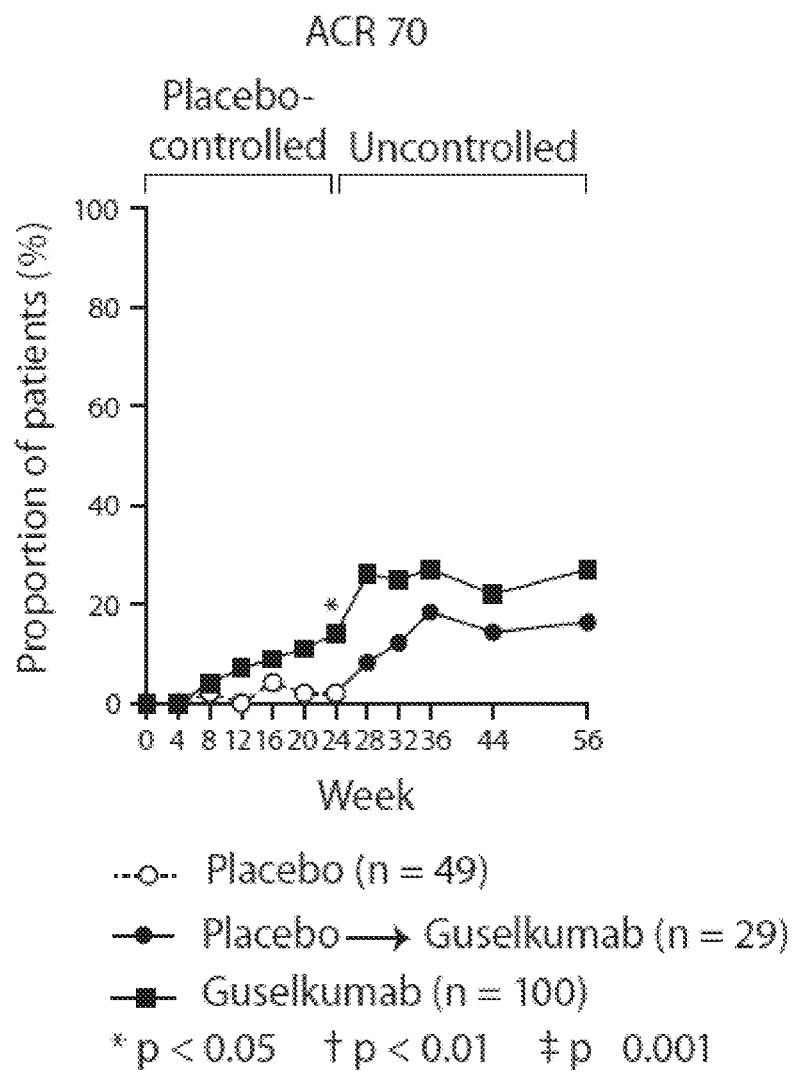
Figure 2D:
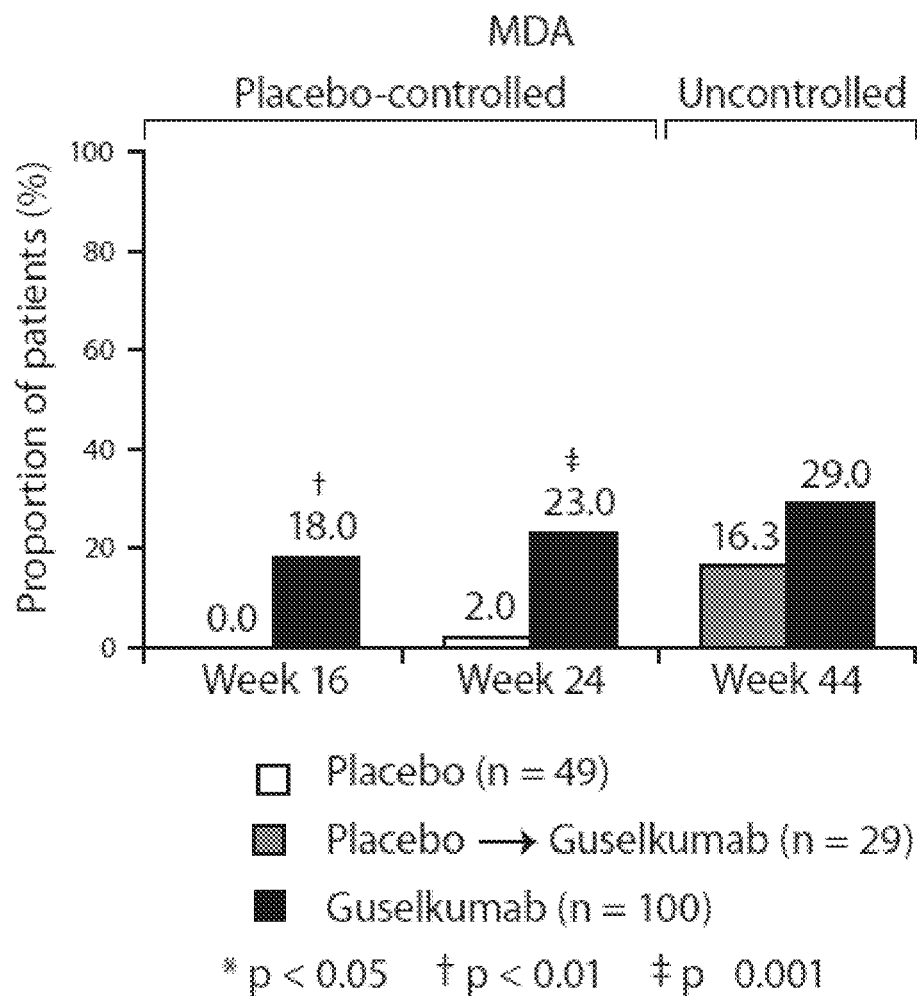

The primary endpoint was met during the placebo-controlled period (Week 0-24). 58.0% vs. 18.4% of guselkumab- vs. placebo-treated patients (P<0.001) achieved an ACR20 response at Week24. Sensitivity analyses were confirmatory (Table 51), and results were consistent regardless of concomitant MTX use (Table 2). Significant improvement in ACR20 response for guselkumab vs. placebo was observed by Week4 (21.0% vs 0, p<0.001), reaching maximum by Week16 (60.0% vs. 16.3%; P<0.001; FIG. 2A). ACR50 and ACR70 (FIG. 2B, 2C) responses were consistently higher among guselkumab- than placebo-treated patients over time through Week24 (ACR50: 34.0% vs. 10.2%, P=0.002; ACR70: 14.0% vs. 2.0%, P=0.023 [calculated post hoc]) (Table 2). Significant improvements were observed in all ACR components at Week24 (P<0.001) (Table S2). Physical function, assessed by HAQ-DI, was significantly improved by guselkumab vs. placebo at Week24 (LSMean difference [95% CI] in HAQ-DI change from baseline: −0.31 [−0.47, −0.15]; P<0.001) (Table 2).

PASI75/90 responses were significantly higher for guselkumab vs. placebo by Week4 (data not shown) and through Week24 (PASI75: 78.6% vs. 12.5%, and PASI90: 66.3% vs. 6.3%, P<0.001; Table 2). PASI100 response was significantly higher at Week24 (39.8% vs. 6.3%; P<0.001).

Among those with baseline enthesitis, 56.6% vs. 29.0% of guselkumab- vs. placebo-treated patients had enthesitis resolution at Week24 (P=0.012). Similar findings were observed for dactylitis resolution at Week24 (55.2% vs. 17.4%; P=0.001) (Table 2). Guselkumab yielded significantly greater improvement in LEI/dactylitis scores than placebo (both with median percent improvements from baseline of 100.0% vs. 33.3%; P≤0.009) among patients with these baseline symptoms. Significantly higher proportions of guselkumab- than placebo-treated patients achieved MDA response at Week24 (23.0% vs. 2.0%; P=0.001; Table 2). Guselkumab significantly improved SF-36 PCS (mean change from baseline: 6.59 vs. 0.46; P<0.001) and MCS (mean change from baseline: 4.95 vs. 0.42; P=0.002) scores vs. placebo by Week24 (Table 2).

Efficacy Post-Week24

Consistent with Week24 results, efficacy outcomes rapidly improved following crossover from placebo→guselkumab at Week24 and were maintained through Week44 (last on-treatment efficacy assessment) and Week56 (final follow-up visit) among patients who continued guselkumab. ACR/MDA responses through Week56 are shown using NRI, FIGS. 2A-D) or based on observed data (Table S3).

Safety

Guselkumab was generally well tolerated. Through Week24, 36.0% of guselkumab- and 32.7% of placebo-treated patients reported ≥1 AEs. Through Week56, 39.5% of guselkumab-treated patients, including 46% of those receiving guselkumab from Week0→Week44, reported ≥1 AEs. AE incidences were comparable regardless of concomitant MTX use and showed no disproportional increase with longer guselkumab exposure (Table 3).

No deaths, anaphylactic/serum sickness-like reactions, or suicidal ideation were reported through Week56. Serious AEs were reported by one placebo (2.0%, joint injury) and one guselkumab (1.0%, myocardial infarction) patients through Week24 and by five additional guselkumab-treated patients (osteoarthritis, pneumonia, pupils unequal, radius fracture, ulcerative keratitis) through Week56. All serious AEs were considered unrelated to study drug by investigators and resolved. The patient with myocardial infarction presented with multiple risk factors (male >45 years, hypertension, hyperlipidemia, family history of early coronary artery disease [<55 years], obesity, tobacco use history), and had atherosclerosis at baseline with prior carotid endarterectomy. Two (1.6%) guselkumab-treated patients discontinued treatment due to AEs through Week44 (last study agent administration) (Table 3). Except one case of basal cell carcinoma in a guselkumab-treated woman (67-year-old Caucasian/fair skin, frequently outdoors), no other malignancy occurred. No injection-site reactions were reported among 750 guselkumab administrations.

Investigators-identified infections occurred in 16.0% and 24.0% of guselkumab- and placebo-treated patients, respectively, through Week24, and in 20.9% of all guselkumab-treated patients through Week56. Serious infections occurred in one (0.8%) guselkumab-treated 78-year-old woman who had two episodes of acute pneumonia (Days179/209) and subsequently discontinued treatment. No candidiasis, active tuberculosis, or opportunistic infections were reported.

Five (3.9%) guselkumab-treated patients reported AEs of neutropenia/neutrophil count decreased, of which four also reported leukopenia/WBC decreased. However, Grade-2

(1000-1500 cells/mm³) or Grade-3 (500-1000 cells/mm³) neutropenia per National Cancer Institute Common Terminology Criteria for AEs (NCI-CTCAE) occurred in three (3.0%, two receiving MTX) and one (1.0%, no MTX), respectively, guselkumab-treated patients through Week56. The patient with Grade-3 neutropenia discontinued treatment, with subsequent spontaneous resolution. Grade-2 neutrophil count decreases were observed for just one visit among each of the three patients and resolved spontaneously with continuous guselkumab. No infections were reported in these four patients through the final follow-up. The proportions of patients with alanine aminotransferase (ALT) or aspartate aminotransferase (AST) increase meeting NCI-CTCAE Grade 1 (1.0-3.0× upper limit of normal [ULN]) or higher criteria were generally comparable between placebo and guselkumab through Week24. Through Week56, four (3.1%) guselkumab-treated patients (three with concomitant MTX) demonstrated ALT increases and five (3.9%) (four with MTX including one with chronic liver disease at baseline) had AST increases meeting NCI-CTCAE Grade 2 (3.0-5.0×ULN). Grade 3 (5.0-20.0×ULN) or higher ALT/AST increases through Week56, not observed in guselkumab-treated patients, occurred in one (2.0%) placebo-treated patient.

Through Week56, 4.7% of guselkumab-treated patients developed non-neutralizing antibodies to guselkumab. No unexpected safety findings were observed in patients early-escaping to ustekinumab through Week56 (Table 3).

Discussion

Guselkumab, a human monoclonal anti-IL-23p19 antibody recently approved in the United States for treating moderate-to-severe psoriasis (Janssen Biotech, Inc, TREMFYA® https://www.tremfyahcp.com), is the first-in-class to demonstrate efficacy in PsA. In this POC trial, guselkumab 100 mg at Week0, Week4, and q8 w significantly reduced joint and skin disease, enthesitis/dactylitis, and improved physical function/quality of life. This study met its primary and all secondary endpoints. Significant improvement of joint/skin disease was observed at Week4 (first post-baseline assessment); improvement was consistently observed in all ACR components and in patient subgroups defined by demographic/disease characteristics (data not shown) and prior/concomitant medications (Table 2). Efficacy was well maintained through ~1 year. The robust efficacy demonstrated by guselkumab verified a critical role of IL-23 in PsA pathogenesis, consistent with findings from previous PsA ustekinumab studies. Both guselkumab and ustekinumab have demonstrated very high clinical response rates in clinical studies of moderate-to-severe psoriasis (Leonardi C L et al. Lancet 2008, 371:1665-74; Papp K A et al, Lancet 2008, 371:1675-84; Blauvelt A. et al, 2017, 76:405-417; Reich K et al, J Am Acad Dermatol 2017, 76:418-31, also highlighting the central role of IL-23 in both psoriasis and PsA.

Genetic polymorphisms in IL-23/IL-23R genes are linked to susceptibility in psoriasis, PsA, and IBD (Bowes J et al, Ann Rheum Dis 2011, 70:1641-44; Duerr R H et al, Science 2006, 314:1461-3; Liu Y et al. PLoS Genet 2008, 4(3): e1000041; Nair R P et al. Nat Genet 2009, 41:199-204. PsA patients have increased risk for IBD (Orchard T R et al, Gut 1998, 42:387-91 and often demonstrate gut bacterial profiles like IBD patients (Scher J U et al, Arthritis Rheum 2015, 67:128-39. Thus, the common immune-mediated inflammatory pathways of the "skin-joint-gut axis" in PsA may be microbiome-induced/mediated, and IL-23 may be crucial to this mechanism. Ustekinumab effectively treats Crohn's disease (CD) (Feagan B G et al, N Engl J Med 2016, 375:1946-60, and two agents targeting IL-23p19 (risankizumab/MEDI2070) have shown promising results in phase-2 CD studies Sands B E et al, J. gastro. 2017, S0016-5085(17)35401-X; Feagan B G et al, Lancet 2017, 389:1699-709. Conversely, two anti-IL-17 agents (secukinumab/brodalumab) did not improve or worsened CD in phase-2 trials (Targan S R et al, Am J Gastroenterol 2016, 111:1599-607, Hueber W et. al. Gut 2012, 61:1693-700, and new onset/worsened IBD was reported in phase-3 secukinumab and ixekizumab studies (Baeten D et al. N Engl J Med 2015, 373:2534-48; Gordon K B et al, N Engl J Med 2016, 375:345-56. Herein, no patient had baseline IBD and no AE of IBD was reported. Guselkumab efficacy in IBD requires evaluation in future clinical studies.

In our PsA population, guselkumab safety through Week56 was generally consistent with that observed in psoriasis (Blauvelt A. et al, 2017, 76:405-417; Reich K et al, J Am Acad Dermatol 2017, 76:418-31), with frequencies of AEs, including infections, comparable to placebo through Week24. NCI-CTCAE Grade-2/3 neutrophil decreases occurred in four (4.0%) guselkumab-treated patients through Week56 and were not associated with MTX use. Neutrophil homeostasis/tissue trafficking are regulated by an IL-17/granulocyte-colony-stimulating-factor-cytokine-controlled loop (Krstic A et al, Immunol Res 2012; 52:34-41, with IL-17 playing an important role in granulopoiesis (Rahman P et al, Arthritis Rheum 2008; 58:1020-5; Langley R G et al, N Engl J Med 2014; 371:326-38; Novartis Pharmaceuticals Corporation. COSENTYX®, https://www.pharma.us.novartis.com/sites/www.pharma.us.novartis.com/files/cosentyx.pdf). Increased incidence of Grade-1/2/3 neutropenia was reported in large phase-3 trials of the anti-IL-17 antibodies secukinumab (Langley R G et al, N Engl J Med 2014; 371:326-38; Novartis Pharmaceuticals Corporation. COSENTYX®, https://www.pharma.us.novartis.com/sites/www.pharma.us.novartis.com/files/cosentyx.pdf), ixekizumab (Eli Lilly and Company, http://pi.lilly.com/us/taltz-uspi.pdf) and brodalumab (Lebwohl et al, N Engl J Med 2015; 373:1318-28); however, in the combined analysis of two large, phase-3, guselkumab psoriasis trials (Blauvelt A. et al, 2017, 76:405-417; Reich K et al, J Am Acad Dermatol 2017, 76:418-31), no cases of Grade-3 or Grade-4 neutropenia were observed and the frequencies of Grade-2 neutropenia were comparable for placebo (3/416, 0.7%) and guselkumab 100 mg (6/821, 0.7%) treatment through Week16 during the placebo-controlled period. Through Week48, Grade-4 neutropenia was not observed, and Grade-3 neutropenia occurred in 1/1,363 (0.1%) guselkumab- and 2/576 (0.3%) adalimumab-treated patients. The frequencies of Grade-2 neutropenia were similar between guselkumab- (22/1363, 1.6%) and adalimumab- (16/576, 2.8%) treated patients. Guselkumab had no remarkable effect on other laboratory parameters, including liver transaminases, glucose, or lipids. Guselkumab's effect on neutrophil counts, liver enzymes, and other laboratory parameters among PsA patients will be further evaluated in large phase-3 trials.

Study limitations include small sample size, relatively short duration, and no assessment of dose response. Lack of an active comparator also limits comparison with other PsA therapies. ACR20 response was selected as the appropriate primary endpoint for this phase-2 POC study with limited sample size, and ACR50, which may be more clinically meaningful, was evaluated as a secondary endpoint, with both showing significant improvement with guselkumab treatment. Guselkumab efficacy/safety in PsA patients with no or limited psoriasis require further evaluation, since all study participants had ≥3% BSA of psoriasis. Too few patients were previously exposed to TNFα-inhibitors to reliably estimate clinical response in this population, as were the numbers of patients with specific PsA subsets (e.g., psoriatic spondylitis). Small imbalances in baseline BSA, PASI, enthesitis, dactylitis and MTX use were due to the small number of placebo patients and are not expected to impact interpretation of efficacy findings.

Thus, among patients with active PsA and ≥3% BSA of psoriasis, guselkumab significantly improved joint symptoms, physical function, psoriasis, enthesitis, dactylitis, and quality of life, with a favorable safety profile possibly differing from IL-17-inhibitors. Findings confirm the critical role of IL-23, and validate it as a treatment target, in PsA.

Additional Clinical Indices

Routine Assessment of Patient Index Data (RAPID3)

The Routine Assessment of Patient Index Data 3 (RAPID3) was also used to evaluate the effect of guselkumab (GUS) on patients with psoriatic arthritis (PsA). RAPID3 (0-30) is derived from the Multi-Dimensional Health Assessment Questionnaire (MDHAQ) numerical rating scale (0-10) for pain and general health. A change of 5.1 in RAPID3 score was identified as the minimally important difference (MID) in PsA, and RAPID3 ≤3.0 was used to define PsA remission.

In a phase 2 trial, patients with active PsA and ≥3% body surface area of plaque psoriasis despite current or previous treatment with standard-of-care therapies, including anti-TNFα agents, were randomized 2:1 to receive GUS 100 mg (n=100) or placebo (PBO, n=49) subcutaneously at weeks 0, 4, and every 8 weeks (q8 w) thereafter through week44. At week16, patients from either group with <5% improvement from baseline in both swollen and tender joint counts were eligible for early escape to open-label ustekinumab. At week24, all remaining PBO patients crossed-over to receive GUS 100 mg, and then received GUS at week28 and q8 w thereafter through week44. Change in RAPID3 and proportion of patients achieving MID were compared between treatments. Correlations of RAPID3 scores with the PsA Disease Activity Score (PASDAS), GRACE index, Disease Activity in Psoriatic Arthritis (DAPSA), and Modified Composite Psoriatic Disease Activity Index (mCPDAI) were evaluated using Spearman correlation.

The mean (SD) RAPID3 score at baseline was 16.9 (5.19). At Week 24, patients in the GUS group achieved statistically significantly greater improvement in RAPID3 (5.81+/−6.0) than the PBO group (0.57+/−0.51, p<0.001), and 50% patients in the GUS group versus 20.4% in the PBO group achieved an MID (p<0.001). Higher remission rate in the GUS than the PBO group (14.0% versus 2.4%, p=0.022) was observed. At week44, mean (SD) improvement was further increased from week24 (6.36 [6.205] to 7.48 [6.310]) in patients who continued Guselkumab. Among patients who switched from PBO to GUS at week24, mean (SD) improvement in RAPID3 was increased from 2.28 (5.244) at week24 while on placebo to 7.60 (6.588) at week44 after switching to GUS. The RAPID3 score was highly correlated with PASDAS (r=0.84, p<0.001), GRACE index (r=0.89, p<0.001), DAPSA (r=0.77 p<0.001) and mCPDAI (r=0.65, p<0.001) at week16.

Lead Enthesitis Index (LEI)

Enthesitis was assessed using the Leeds enthesitis index (LEI). Enthesitis scores during the 24-week double-blind treatment were analyzed using LOCF imputation for missing data and early escape. Enthesitis after week24 was analyzed using observed data.

Of 149 total patients with active PsA, 107 (72%) presented with enthesitis at baseline (PBO N=31, mean [SD] LEI=2.6 [1.48], median [range]=2.0 [1, 6]; GUS N=76, mean (SD) LEI=2.7 [1.54], median [range]=2.0 [1, 6]) and 85 continued at Week 24 (PBO→GUS N=18; GUS→GUS N=67). Except for higher tender/swollen joint counts & CRP, baseline characteristics of the enthesitis subset was similar to the overall population. Guselkumab significantly reduced the LEI by Week 8 (mean [SD]] change from baseline, PBO: −0.4 [1.59]; GUS: −1.2 [1.65]; p=0.037), and through Week 24 (mean [SD] change from baseline, PBO: −0.7 [1.53]; GUS: −1.5 [1.81]; p=0.045). After Week 24, the PBO→GUS group achieved rapid, sustained resolution (Week 56: mean[SD] change from BL=−2.1 [1.65]; 62.5% of patients with resolution), similar to GUS→GUS group (Week 56: mean[SD] change from BL=−1.9 [1.59], 70.8% of patients with resolution). Guselkumab also significantly increased the percent of patients with enthesitis resolution. Improvement in enthesitis was observed at each enthesitis site assessed. Improvement was greater in ACR20 responders versus non-responders in Guselkumab-treated patients. Enthesitis improvement was correlated with reduction in tender (R=0.37, p=0.001), swollen (R=0.27, p=0.020) joint counts, physician's (R=0.47, p<0.0001) and patient's global assessment of disease activity (R=0.32, p=0.005), change in SF36 PCS (R=0.27, p=0.02) and MCS (R=0.35, p=0.002).

Guselkumab treatment produces rapid and sustained improvement of enthesitis in patients with active PsA, which correlates with improvement in joint symptoms and patient-reported outcomes.

Dactylitis Index

Dactylitis was assessed by scoring each digit from 0-3 (0=absent, 1=mild, 2=moderate, 3=severe), for a combined score of 0-60. Sensitivity analysis of change from BL through week24 in dactylitic digits was performed (combined score 20). Dactylitis scores during the 24-week double-blind treatment was analyzed using LOCF imputation for missing data and early escape (EE). Dactylitis after week24 was evaluated using observed data.

Figure 7A:
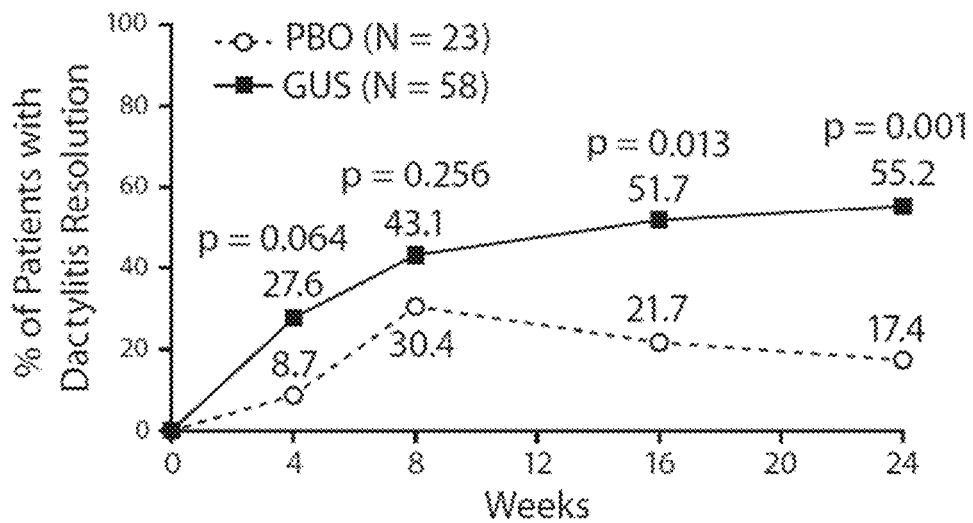
FIGS. 7A and 7B. Show proportion of patients with dactylitis resolution over time.
Figure 7B:
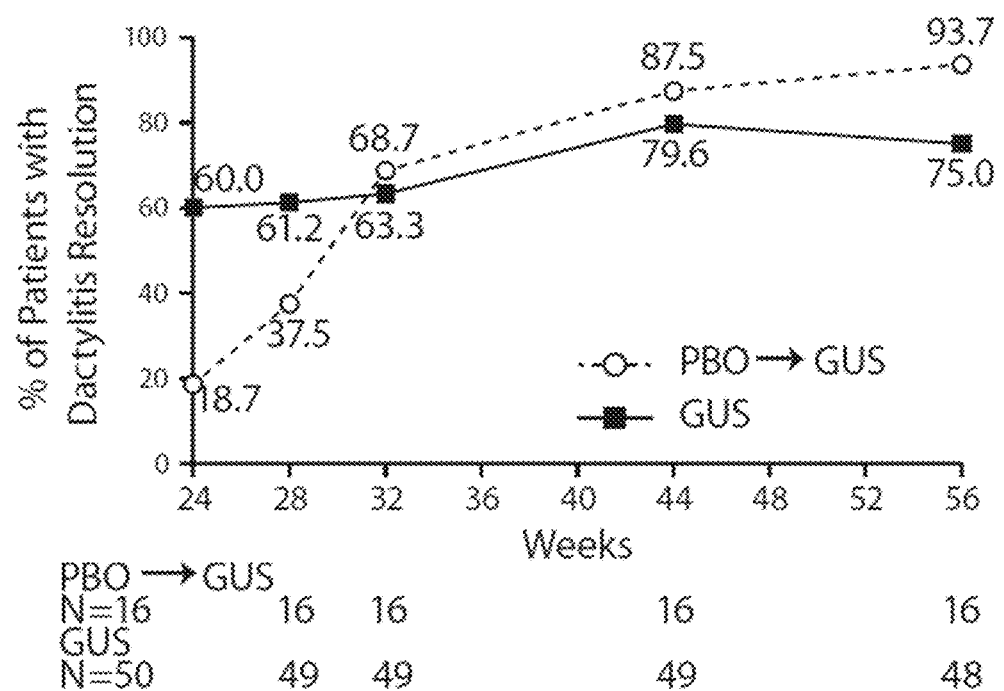

Of 149 patients, 81 presented with dactylitis at baseline (PBO N=23, mean[SD]=3.9[3.01]; GUS N=58, mean[SD]= 6.5[6.15]) and 66 continued to the active treatment period (PBO→GUS N=16; GUS→GUS N=50). The dactylitis subset was similar to the overall population at baseline characteristics except for higher median values for the number of swollen joints, the number of tender joints, and CRP. At weeks 16 and 24, the GUS group had a significantly greater reduction in the dactylitis score (week24 mean [SD] change from baseline, PBO: −0.4 [6.06]; GUS: −3.8 [4.93]; p=0.006) and a greater % of patients w/ dactylitis resolution, compared to the PBO group (FIGS. 7A and 7B). Consistent results were obtained with number digits with dactylitis (week24 mean [SD] change from baseline, PBO: −0.2 [3.04]; GUS: −2.1 [2.21]; p=0.003). Improvement in dactylitis seen at week24 was maintained in the GUS→GUS group (week56: mean[SD] change from BL=−5.5 [4.84], 75% of pts w/ resolution) and the values for the PBO→GUS group (week56: mean[SD] change from BL=−4.4 [3.50], 93.7% of patients with resolution) approached those of the GUS→GUS group. Improvement in dactylitis was greater in ACR20/ACR50 responders versus non-responders in GUS-treated patients (Table S5) and was significantly correlated with improvement in TJC (R=0.38, p=0.004), SJC (R=0.50, p<0.0001), & HAQ-DI score (R=0.33, p=0.013).

GUS is efficacious in resolving symptoms of dactylitis in patients with active PsA. This effect on dactylitis is correlated with improvement in joint symptoms and physical function.

Composite Endpoints PASDAS, GRACE, mCPDAI and DAPSA

Psoriatic ArthritiS Disease Activity Score (PASDAS), GRAppa Composite scorE (GRACE) Index, modified Composite Psoriatic Disease Activity Index (mCPDAI), and Disease Activity Index for PSoriatic Arthritis (DAPSA) are composite indices recently developed to assess disease activity in psoriatic arthritis (PsA). Given the diverse and highly individual clinical and radiographic presentations of psoriatic arthritis (PsA), composite indices may be more useful in assessing disease activity and defining clinically meaningful treatment targets compared with conventional scoring systems. While multiple PsA composite indices have recently been proposed, there currently is no consensus within the rheumatology community regarding the choice of composite disease activity measures, and performance data for PsA-specific composite indices are lacking. The effect of guselkumab (GUS) on these indices was evaluated in a Phase 2 study in patients with active PsA. The performance of the PsA composite indices was assessed using standardized mean difference, effect size and standardized response mean.

Materials and Methods

Ethics

This study (NCT02319759) was conducted according to Declaration of Helsinki and Good Clinical Practice guidelines. The protocol was approved by each site's governing ethical body; patients provided written informed consent.

Study Design

As reported (Deodhar 2018), patients enrolled into this double-blind, placebo-controlled, parallel-group, two-arm, multicenter trial were centrally randomized (2:1) to receive subcutaneous guselkumab or placebo. Study drugs were provided in identical prefilled syringes; all patients received the same number of injections at the same time points.

Patients randomized to guselkumab received guselkumab 100 mg at Weeks0, 4, 12, 20, 28, 36, and 44, and placebo at Week24. Patients randomized to placebo received placebo at Weeks0, 4, 12, and 20 and guselkumab 100 mg at Weeks24, 28, 36, and 44.

Patients with <5% improvement in swollen and tender joint counts (TJCs and SJCs) at Week16 early escaped to open-label ustekinumab (Janssen Biotech, Inc., Horsham, PA, USA), i.e., placebo→ustekinumab or guselkumab→ustekinumab, at Weeks16, 20, 32, and 44 according to approved country-specific prescribing information. A final follow-up visit occurred at Week56.

Patients

Eligible patients included adults with PsA for ≥6 months, fulfilling Classification Criteria for Psoriatic Arthritis (CASPAR) (Taylor 2006), ≥3 tender and ≥3 swollen joints, C-reactive protein (CRP) ≥0.3 mg/dL, ≥3% BSA of plaque psoriasis, and an inadequate response to standard therapies (Deodhar 2018). Patients who received one prior anti-tumor necrosis factor alpha agent were permitted, but limited to 20% of participants, following 8-12 weeks of washout. Stable doses of methotrexate (MTX; ≤25 mg/week), oral corticosteroids (≤10 mg/day of prednisone/equivalent), and nonsteroidal anti-inflammatory drugs were permitted, but not required, through Week24. Sulfasalazine (≤3 g/day) and leflunomide (≤20 mg/day) were permitted following Week24. Other disease-modifying antirheumatic drugs (DMARDs) and biologics were prohibited.

Procedures

Independent assessors evaluated joint tenderness (N=68) and swelling (N=66, excluding hips). Patients reported pain (0-100 mm visual analog scale [VAS]), global disease activity (0-100 mm VAS for arthritis, psoriasis, and both), and physical function (HAQ-DI). Investigators completed the global assessment of disease activity (0-100 mm VAS), and serum CRP was determined. The joint assessor also evaluated dactylitis (0-none to 3-severe) for each finger and toe (total score 0-60) and enthesitis using the LEI. The PASI assessed skin disease severity and extent. The SF-36 assessed physical and mental HRQoL. Key efficacy assessments were performed at screening, baseline, every 4 weeks through Week36, Week44, and Week56.

Outcomes

As reported (Deodhar A et al. Lancet, 2018, 391:2213-24), patients achieved MDA if meeting ≥5/7 criteria: TJC ≤1/68, SJC ≤1/66, PASI ≤1, patient pain VAS ≤15, patient global disease activity VAS (arthritis and psoriasis)≤20, HAQ-DI≤0.5, and tender entheseal points ≤1 (Coates 2010). Patients meeting all seven criteria achieved VLDA (Coates L C et al, Ann Rheum Dis 2010; 69:48-53).

The PASDAS (Helliwell 2013, Helliwell 2014b) was calculated using: patient global VAS (arthritis and psoriasis, 0-100 mm), physician global VAS (0-100 mm), TJC, SJC, CRP (rescaled to mg/L), enthesitis (LEI), dactylitis (scores of 0-3 recoded to 0-1, where any score >0 equaled 1), and the PCS score of the SF-36. Disease activity cutoffs were: very low (≤1.9), low (>1.9-≤3.2), moderate (>3.2-<5.4), high (≥5.4) (Helliwell P S et al, Ann Rheum Dis 2010, 69:48-53).

The GRACE derives from the Arithmetic Mean of the Desirability Function (AMDF), calculated by transforming the following variables, using predefined algorithms and expressing the total score as a mean ranging from 0-1, where 1 indicates a better state than 0: TJC, SJC, HAQ-DI, patient's global VAS (arthritis and psoriasis, 0-100 mm), patient's assessment of skin disease activity VAS (0-100 mm), patient's global assessment VAS (arthritis, 0-100 mm), PASI, derived PsAQoL index (PsAQoL=25.355+[2.367× HAQ-DI]−[0.234×SF-36 PCS score]−[0.244×SF-36 mental component summary score]). The GRACE was then calculated as (1−AMDF)×10, with the following disease activity cutoffs: low (≤2.3), moderate (>2.3-<4.7), high (≥4.7) (Helliwell P S et al, Ann Rheum Dis 2010, 69:48-53; Helliwell P S et al, Arthritis Care Res 2014b; 66:749-56).

The CPDAI (Mumtaz 2011), modified for PsA (mCPDAI) to assess four domains (joints, skin, entheses, dactylitis), was calculated based on TJCs, SJCs, HAQ-DI, PASI, and dactylitis/enthesitis scores. Within each domain, scores of 0-3 were assigned according to predefined cutoffs and summed to yield a total score of 0-12. Adjusted disease activity cutoffs ([CPDAI/15]×12) were: low (≤3.2), moderate (>3.2-<6.4), high (≥6.4) (Helliwell P S et al, Arthritis Care Res 2014b; 66:749-56).

The DAPSA was calculated as the sum of the TJC, SJC, CRP (mg/dL), patient assessment of pain VAS (0-10), and patient global assessment VAS (arthritis, 0-10) (Helliwell 2014b). The disease activity cutoffs were: remission (≤4), low (>4-≤14), moderate (>14-≤28), high (>28) (Schoels M M et al, Ann Rheum Dis 2016; 75:811-8).

Statistical Analyses

All efficacy analyses through Week24 included patients who received ≥1 administration of randomized study drug with data handling rules applied (full analysis set). Patients who met treatment-failure criteria (i.e., discontinued study agent resulting from lack of efficacy/PsA worsening, initiated or increased the dose of MTX or oral corticosteroids for PsA, or initiated protocol-prohibited medications and/or therapies) were considered nonresponders for MDA/VLDA after treatment failure through Week24, as were patients who had missing data or early escaped at Week16. For continuous endpoints and response endpoints derived from continuous variables through Week24, patients with missing baseline data were excluded. Last-observation-carried-forward methodology was employed to impute post-baseline missing data or data post-early escape. Post-Week24, all patients received active treatment, and no statistical comparisons were planned. Therefore, observed data were employed to summarize post-Week24 data among the 29 patients who early escaped from placebo→guselkumab and the 86 guselkumab-randomized patients who did not early escape at Week16 and did not discontinue study drug prior to Week24, with Week24 data in these patients included as a reference. Statistical analyses were performed using SAS version 9.2 (SAS Institute, Inc., Cary, NC, USA).

To examine correlations between improvements in disease activity detected by each PsA composite index with improvements in HRQoL, mean improvements from baseline to Week24 in the SF-36 PCS score were summarized by disease activity state among guselkumab-treated patients. Changes in composite index scores from baseline to Week16 and Week24 were summarized using descriptive statistics, and between-treatment comparisons of change in composite indices were performed using an analysis of variance (ANOVA). Between-treatment comparisons of the proportions of patients achieving very low disease activity or remission were performed post hoc with Fisher's Exact test.

The relative performance of each index was assessed via calculation of treatment group effect size (ES; the absolute value of the mean difference between baseline and Week24 values divided by the standard deviation [SD] at baseline). ES values are used to categorize treatment effects as trivial ($<0.20$), small ($\geq 0.20$ to $<0.50$), moderate ($\geq 50$ to $<0.80$), or large ($\geq 0.80$) (Altman 1991). Additional comparative statistics included standardized mean differences (SMDs; the absolute value of mean difference in change from baseline [guselkumab minus placebo] divided by the pooled SD of change from baseline at Week24) and treatment group standardized response means (SRMs; the absolute value of mean change from baseline divided by the SD of change from baseline at Week24). The proportions of patients meeting residual disease activity criteria (defined by CRP ≤upper limit of normal [0.287 mg/dL], dactylitis score=0, enthesitis LEI score=0, PASI ≤1, TJC ≤1/68, SJC ≤1/66) were assessed among patients achieving PsA-specific composite endpoint low disease activity/remission states, MDA, or VLDA at Week24.

Results

Disposition and Baseline Characteristics

This Phase 2 trial was conducted at 34 sites (Canada, Germany, Poland, Romania, Russia, Spain, United States). Patient screening began on Mar. 27, 2015, and the last patient visit was completed on Jan. 17, 2017. Patient disposition has been reported (Deodhar 2018). Briefly, 149 patients were randomized to placebo (N=49) or guselkumab 100 mg (N=100). Seventeen of 49 (34.7%) placebo- and 10/100 (10.0%) guselkumab-treated patients qualified for early escape to ustekinumab at Week16. Twenty-nine of 49 (59.2%) patients in the placebo group crossed over to receive guselkumab at Week24; 28 placebo→guselkumab patients completed the study through Week44. Eighty-six of 100 (86.0%) patients in the guselkumab group completed Week24 and continued guselkumab treatment; 84 patients completed the study through Week44.

Baseline characteristics were generally similar between randomized groups and indicated moderate-to-severe arthritis, with substantial disability (mean HAQ-DI: 1.39). At study outset, 71.8% and 54.4% of patients presented with enthesitis and dactylitis, respectively (Deodhar 2018). Baseline mean PASDAS (6.5), GRACE (6.1), mCPDAI (7.5), and DAPSA (46.7) scores also demonstrated moderate-to-high disease activity across treatment groups. Further, the proportions of patents with moderate-to-high disease activity at baseline were comparable between treatment arms for each of the PASDAS (both 100%), GRACE (both 100%), mCPDAI (both ~96%), and DAPSA (100% and 99%) composite indices (FIGS. 3C-J).

Validation of PsA-Specific Composite Indices Using SF-36 PCS as an Anchor

Changes from baseline to Week24 in SF-36 PCS scores were consistent with disease activity states defined by each PsA composite index in guselkumab-treated patients. Specifically, the largest improvements in SF-36 PCS were observed in patients with remitted/very low/low disease activity at Week24 (9.5-12.9 across indices), which were significantly higher than those observed in patients with moderate (4.1-6.4; $p<0.05$) or high (0.6-2.7; $p<0.001$) disease activity at Week24 (FIGS. 4A-D).

The Effect of Guselkumab on PsA-Specific Composite Endpoints

Placebo-Controlled Period:

Guselkumab significantly improved disease activity from baseline to Week24, relative to placebo, when assessed using the PASDAS (mean changes: −2.5 vs. −0.5, respectively), GRACE (−2.7 vs. −0.4), mCPDAI (−3.9 vs. −0.8), and DAPSA (−23.1 vs. −5.0) composite indices (all $p<0.001$; FIGS. 3D, 3F, 3H, 3J). Consistently, significantly higher proportions of guselkumab- than placebo-treated patients achieved low disease activity when assessed by the PASDAS (35.0% vs. 4.1%; $p<0.001$), GRACE (29.6% vs. 2.1%; $p<0.001$), mCPDAI (51.0% vs. 16.7%; $p<0.001$), and DAPSA (40.0% vs. 12.2%; $p<0.01$) composite indices.

Figure 3A:
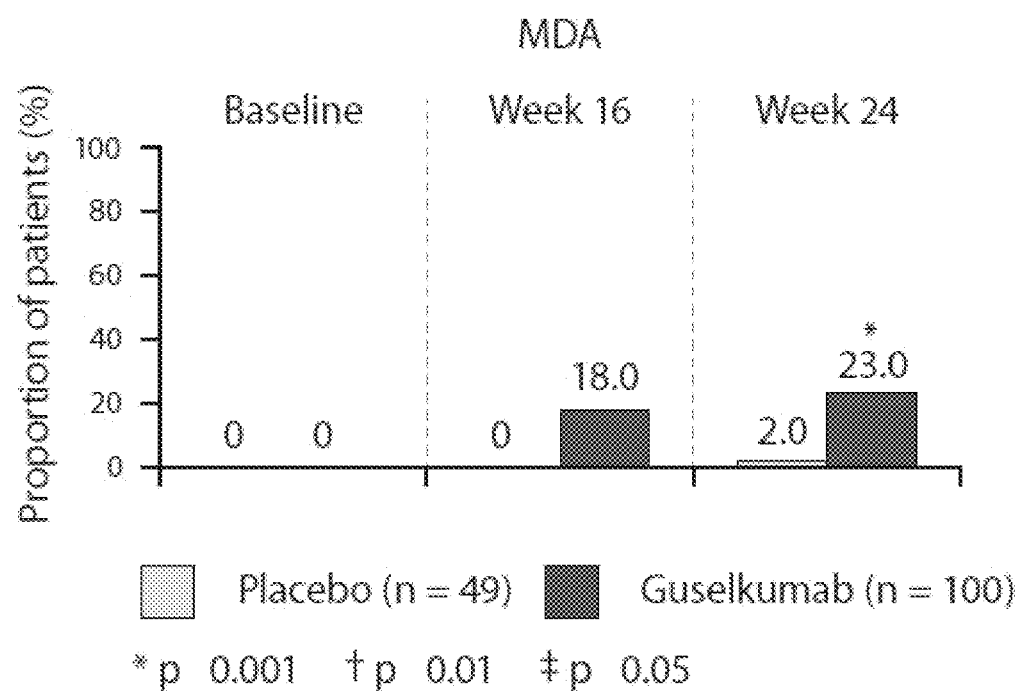
Figure 3B:
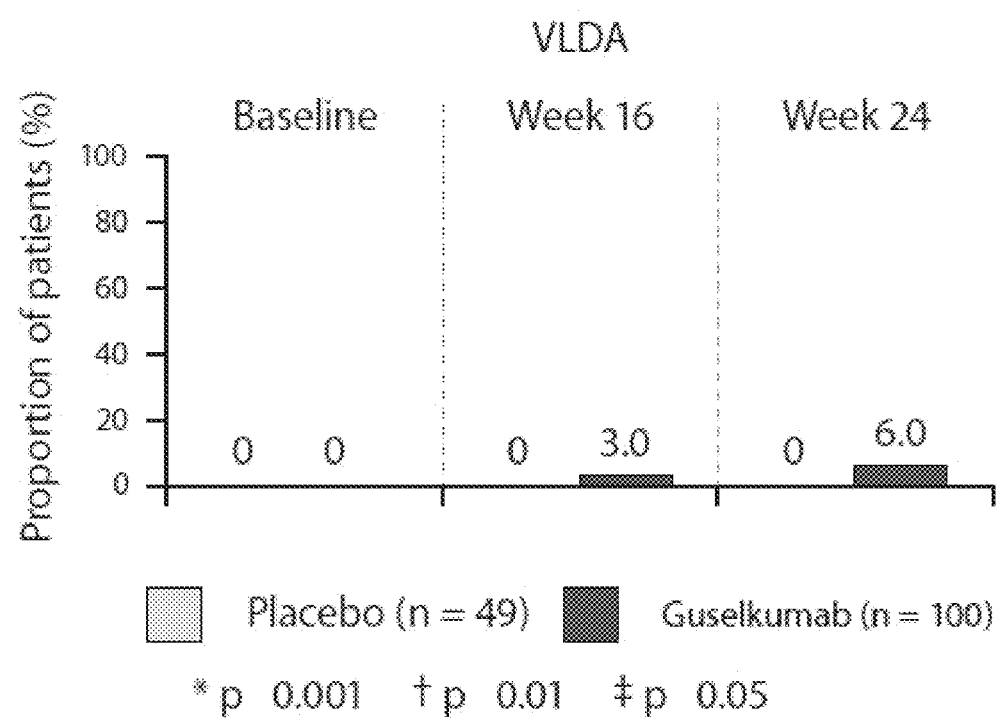
Figure 3C:
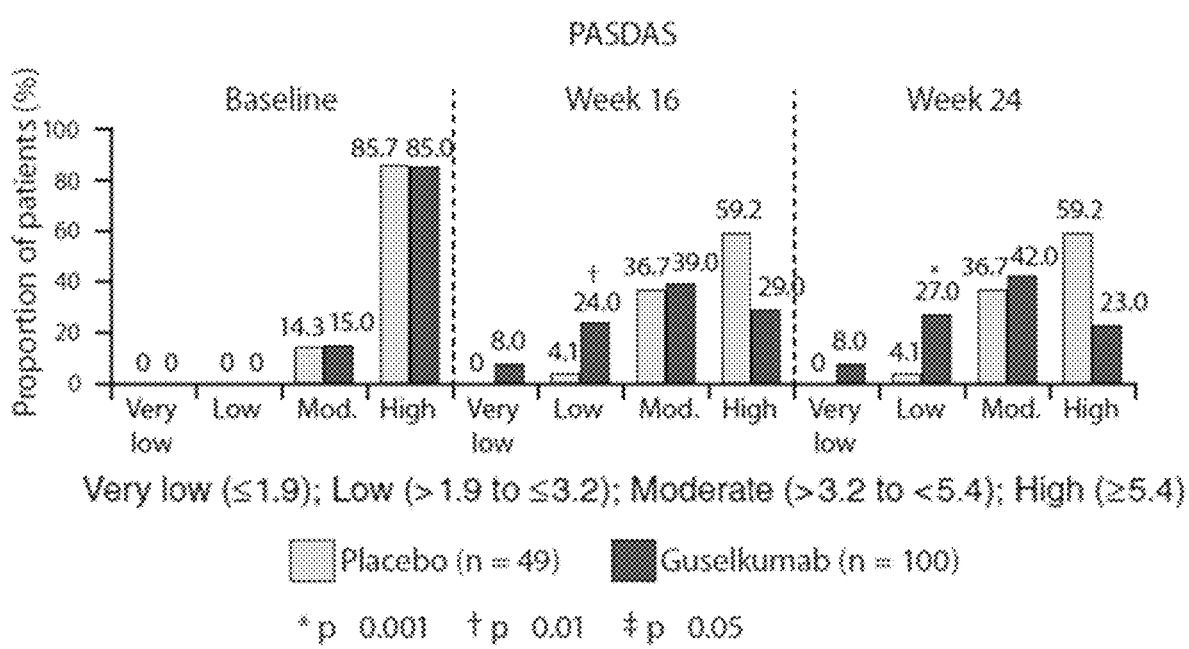
Figure 3D:
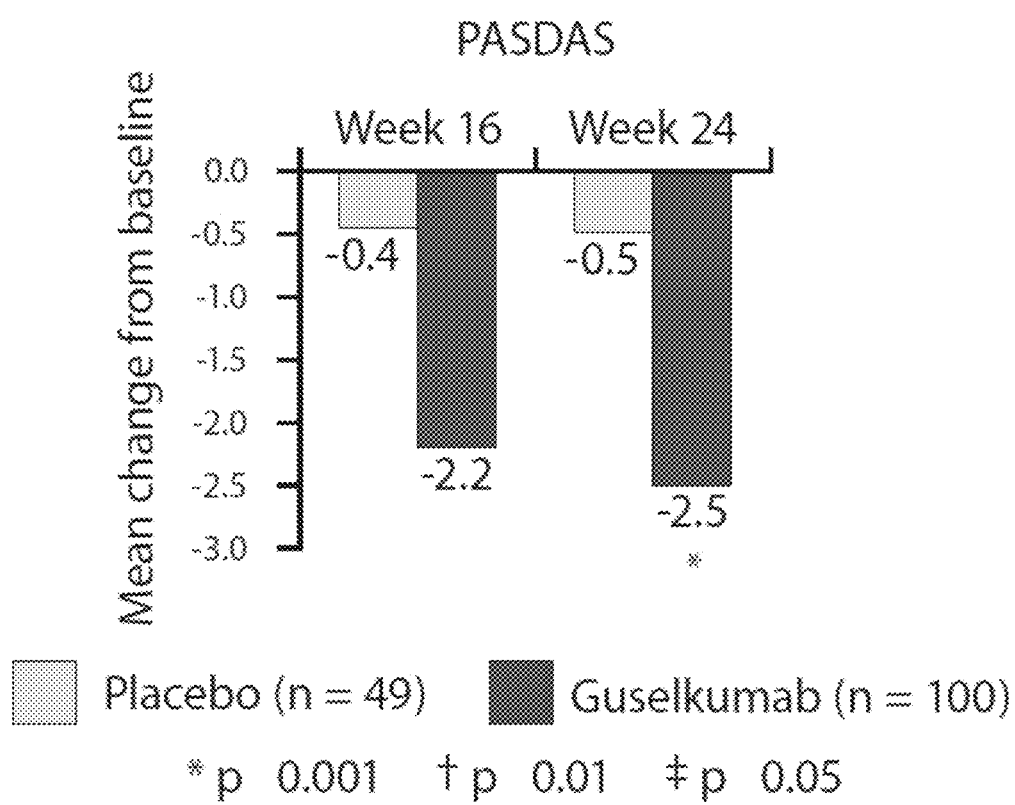
Figure 3E:
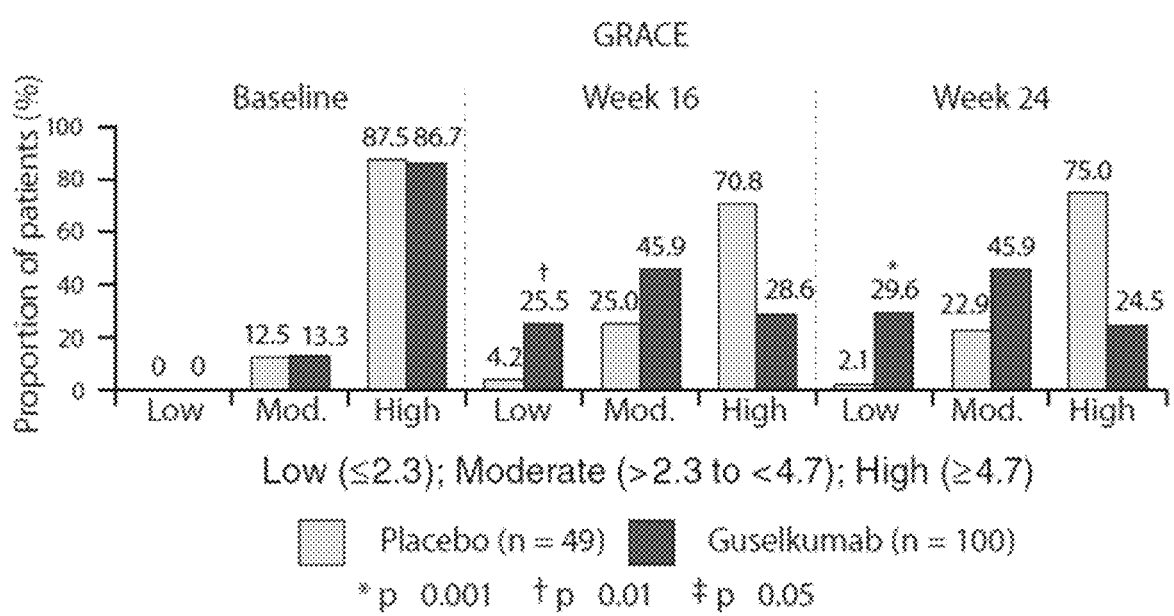
Figure 3F:
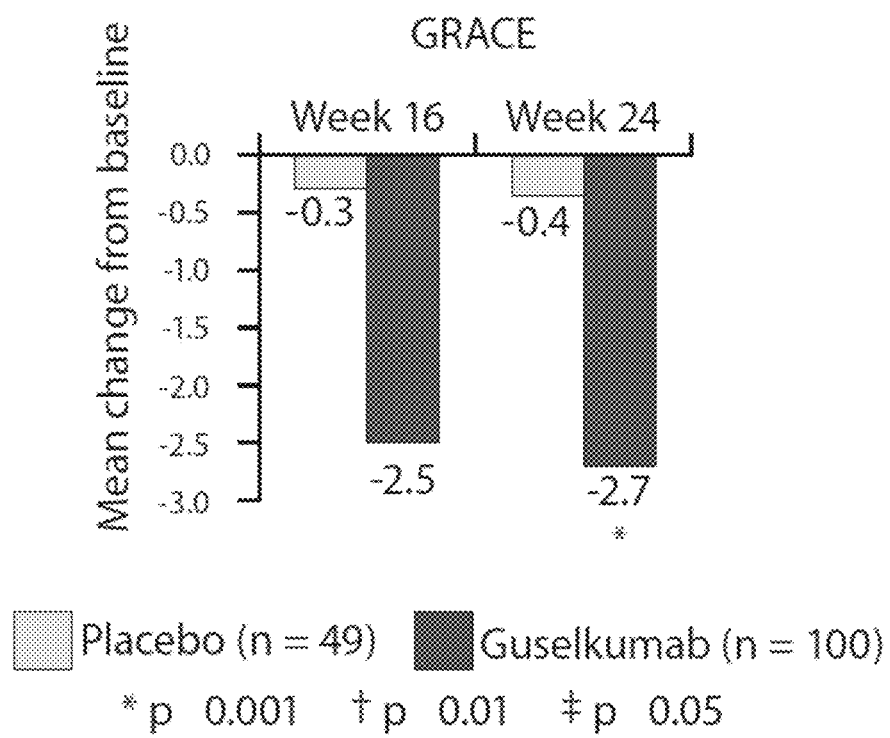
Figure 3G:
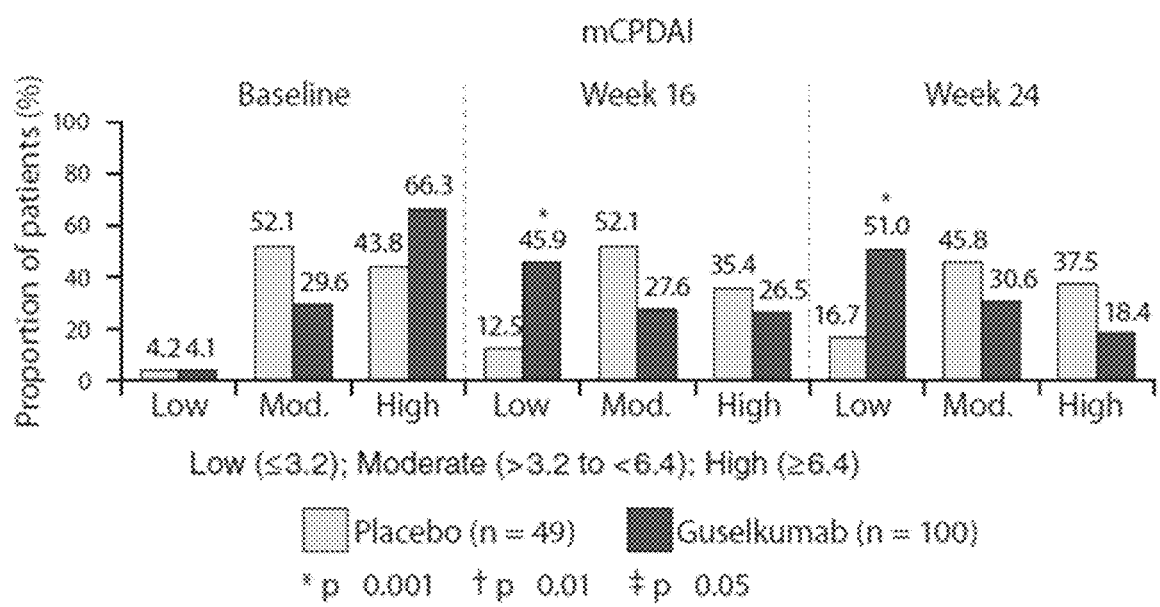
Figure 3H:
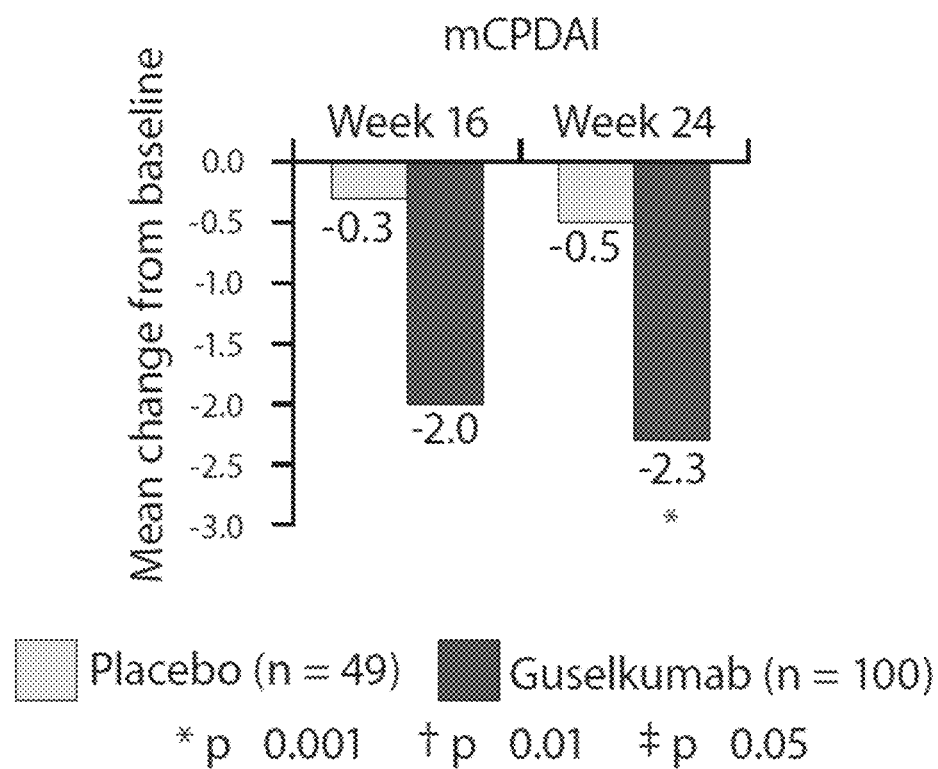
Figure 31:
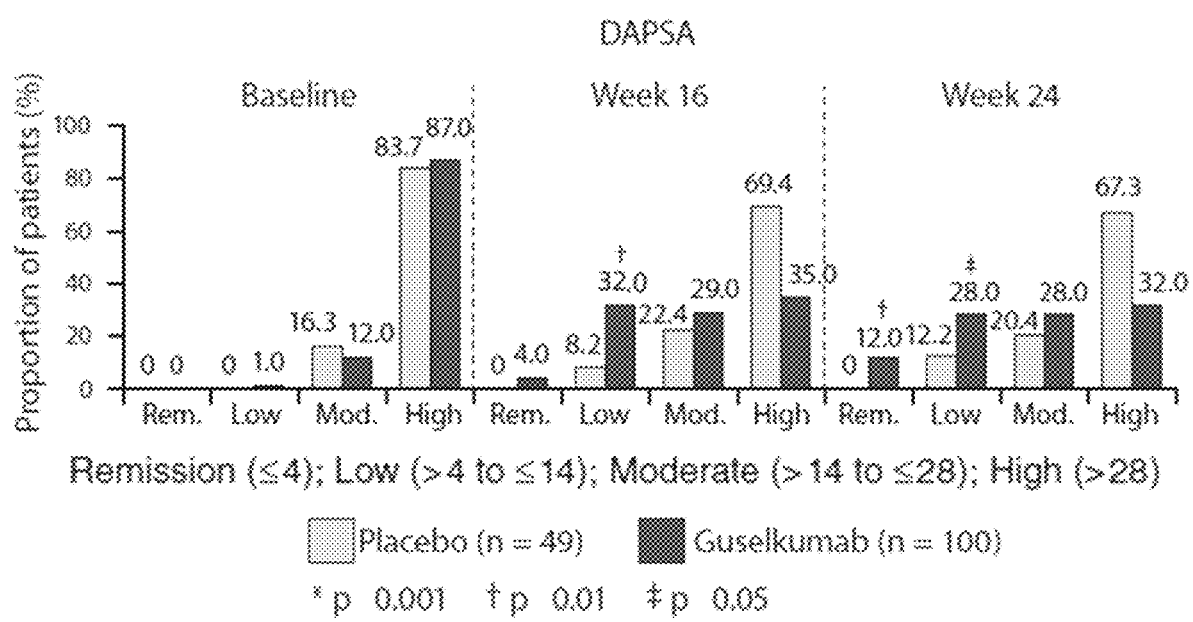
Figure 3J:
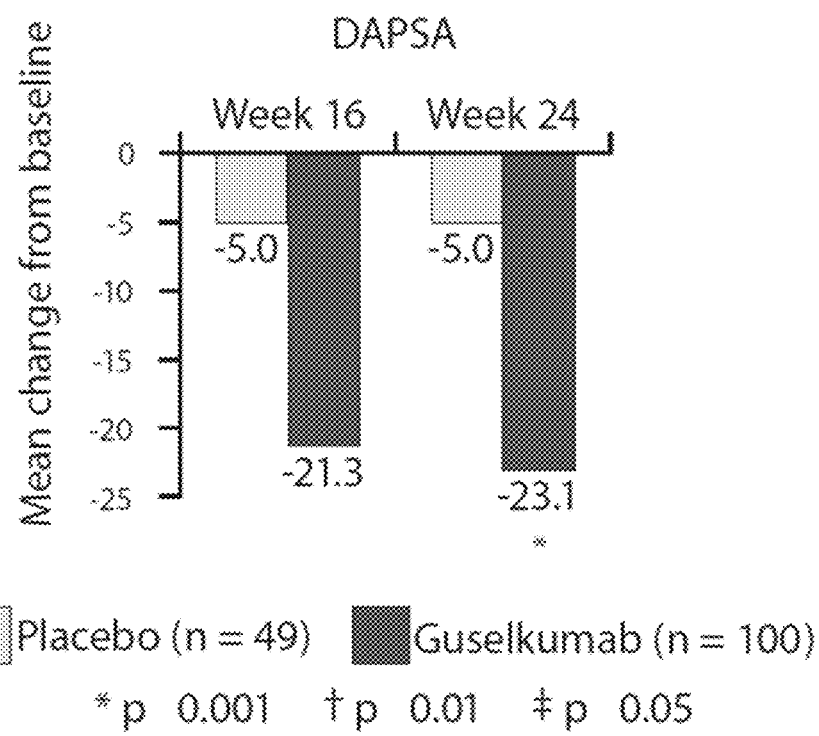
Figure 4A:
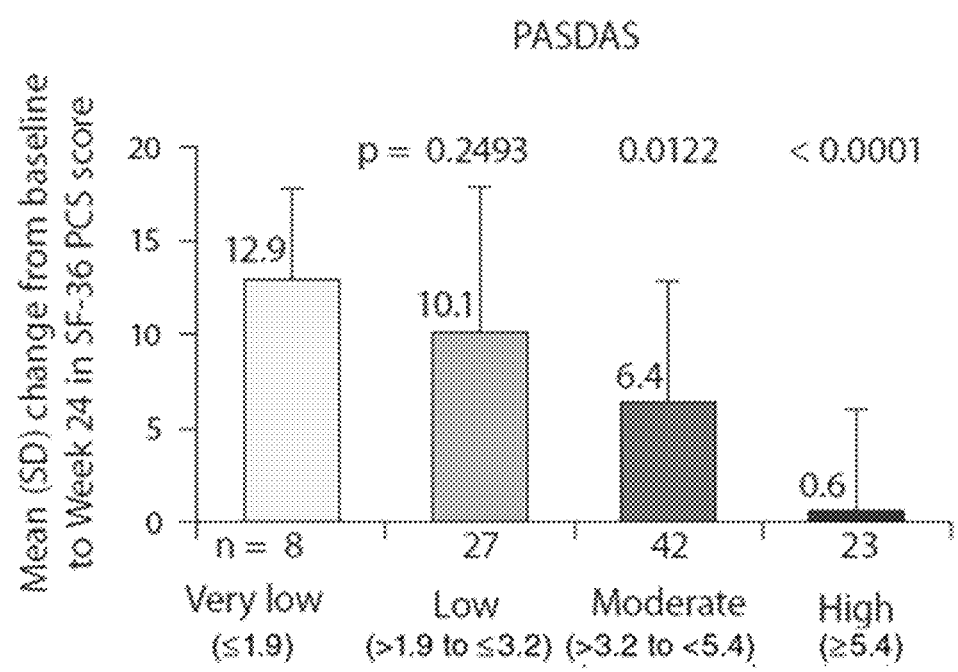
FIGS. 4A-D. Show mean changes from baseline at Week 24 in the SF-36 PCS score by disease activity state according to the PASDAS (4A), GRACE (4B), mCPDAI (4C), and DAPSA (4D) PsA-specific composite endpoints (guselkumab-treated patients in the full analysis set; last observation carried forward for missing data). DAPSA=Disease Activity Index for PSoriatic Arthritis, GRACE=Group for Research and Assessment of Psoriasis and Psoriatic Arthritis (GRAppa) Composite scorE, mCPDAI=modified Composite Psoriatic Disease Activity Index, PASDAS=Psoriatic ArthritiS Disease Activity Score, PCS=physical component summary, PsA=psoriatic arthritis, SF-36=36-item Short Form health survey.
Figure 4B:
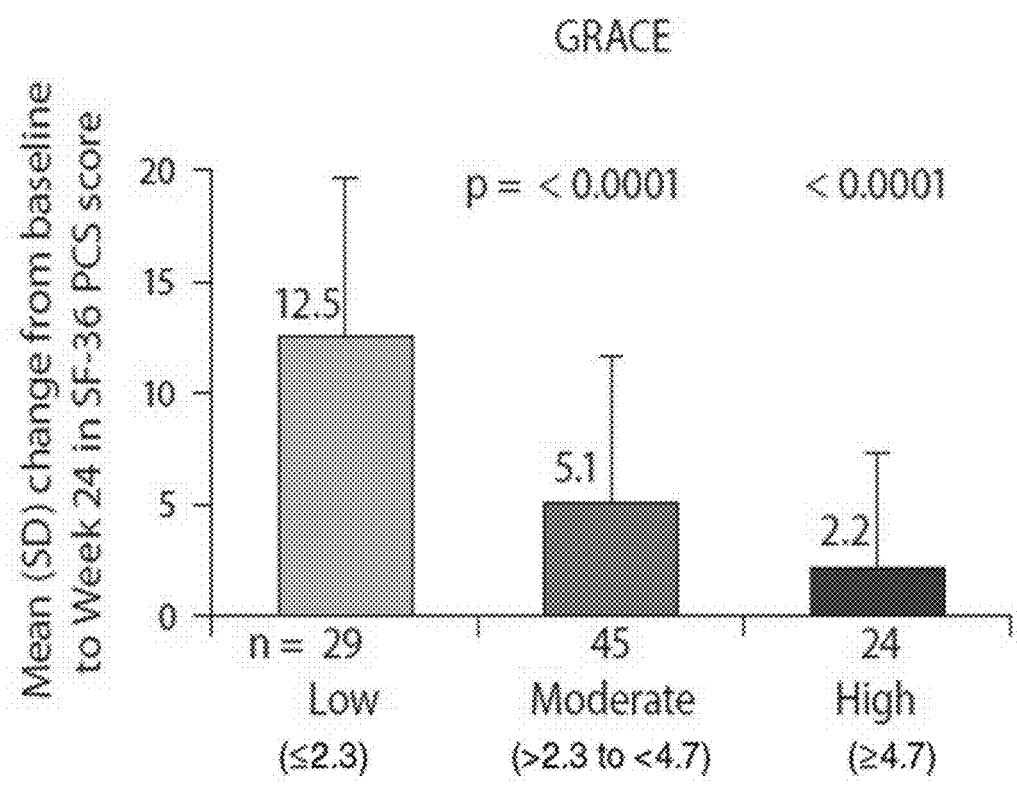
Figure 4C:
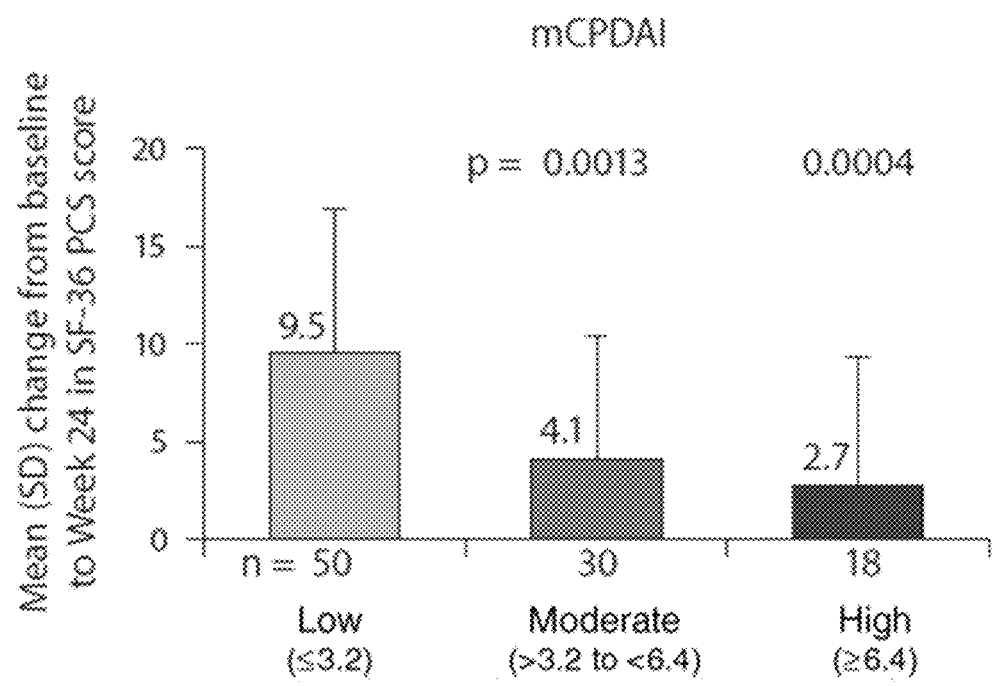
Figure 4D:
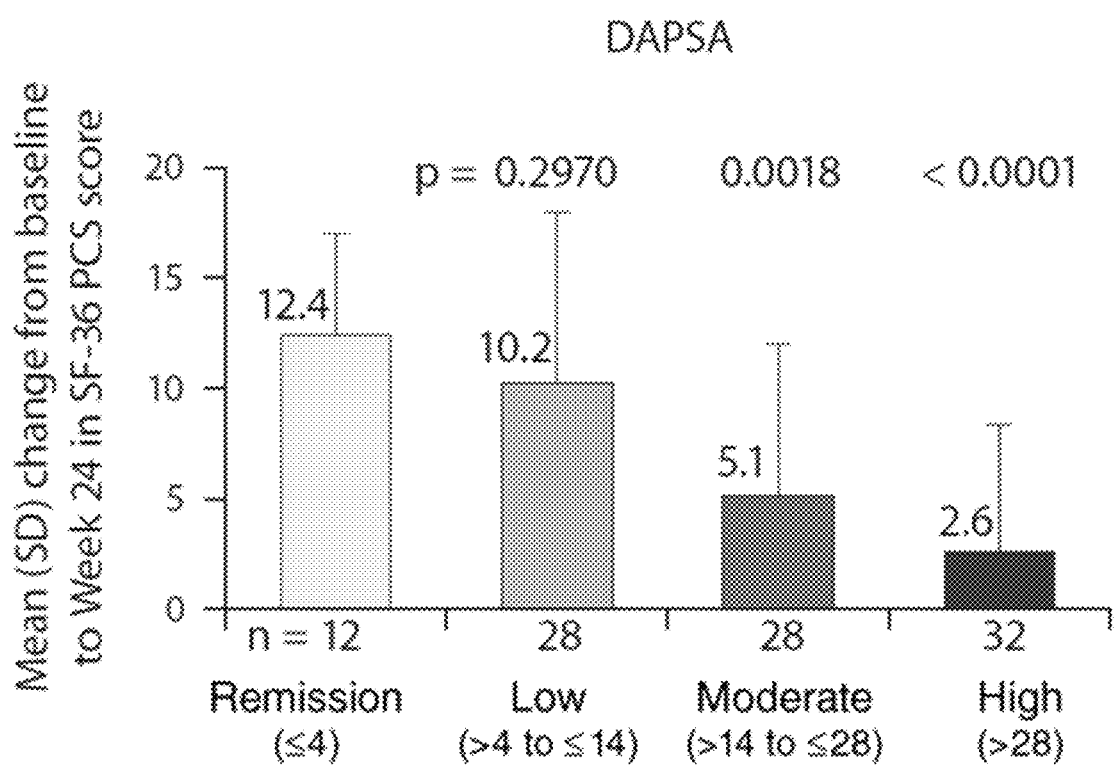

Further, more patients achieved very low disease activity based on PASDAS (8.0% vs. 0, $p=0.053$) and significantly more patients achieved DAPSA remission (12.0% vs. 0; $p<0.01$) (FIGS. 3C, 3E, 3G, 3I). For comparison, as reported previously (Deodhar 2018), 23% of guselkumab-treated patients achieved MDA vs. 2.0% of placebo-treated patients ($p=0.001$) (FIG. 3A). A similar response pattern was observed for VLDA, i.e., 6% of guselkumab-treated patients vs. no placebo-treated patients ($p=0.076$) (FIG. 3B).

Figure 5A:
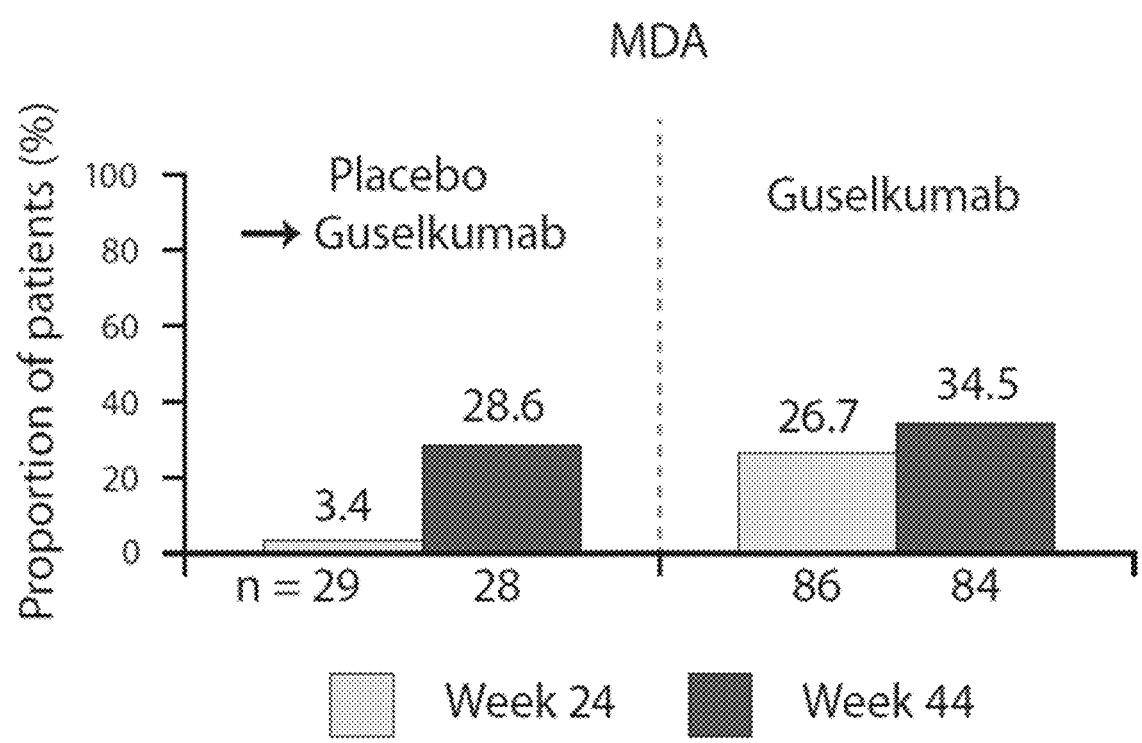
FIGS. 5A-J. Show proportions of patients achieving MDA (5A) and VLDA (5B) and proportions of patients achieving disease activity states, and mean changes from baseline, post-Week 24 for PASDAS (5C, 5D), GRACE (5E, 5F), mCPDAI (5G, 5H), and DAPSA (5I, 5J) PsA-specific composite endpoints (post-Week 24 efficacy analysis set; observed data). Week-24 observed data in the same population included as a reference. DAPSA=Disease Activity Index for PSoriatic Arthritis, GRACE=Group for Research and Assessment of Psoriasis and Psoriatic Arthritis (GRAppa) Composite scorE, mCPDAI=modified Composite Psoriatic Disease Activity Index, MDA=minimal disease activity, PASDAS—Psoriatic ArthritiS Disease Activity Score, PsA=psoriatic arthritis, VLDA=very low disease activity.
Figure 5B:
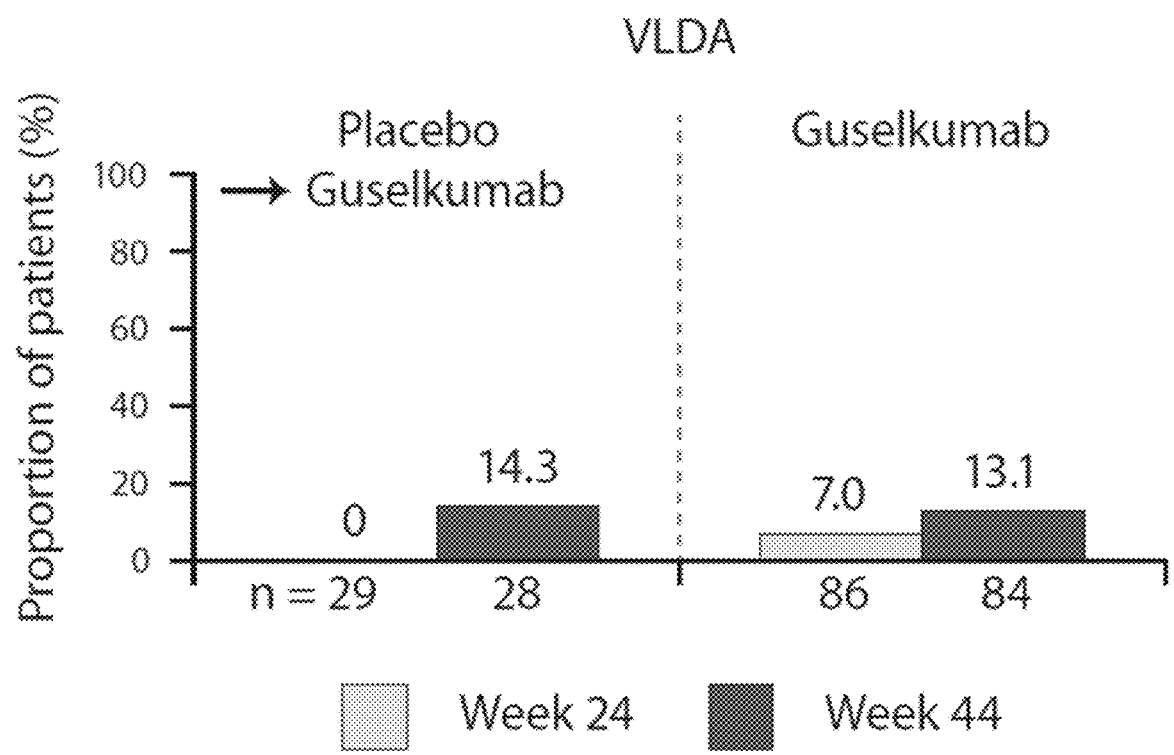
Figure 5C:
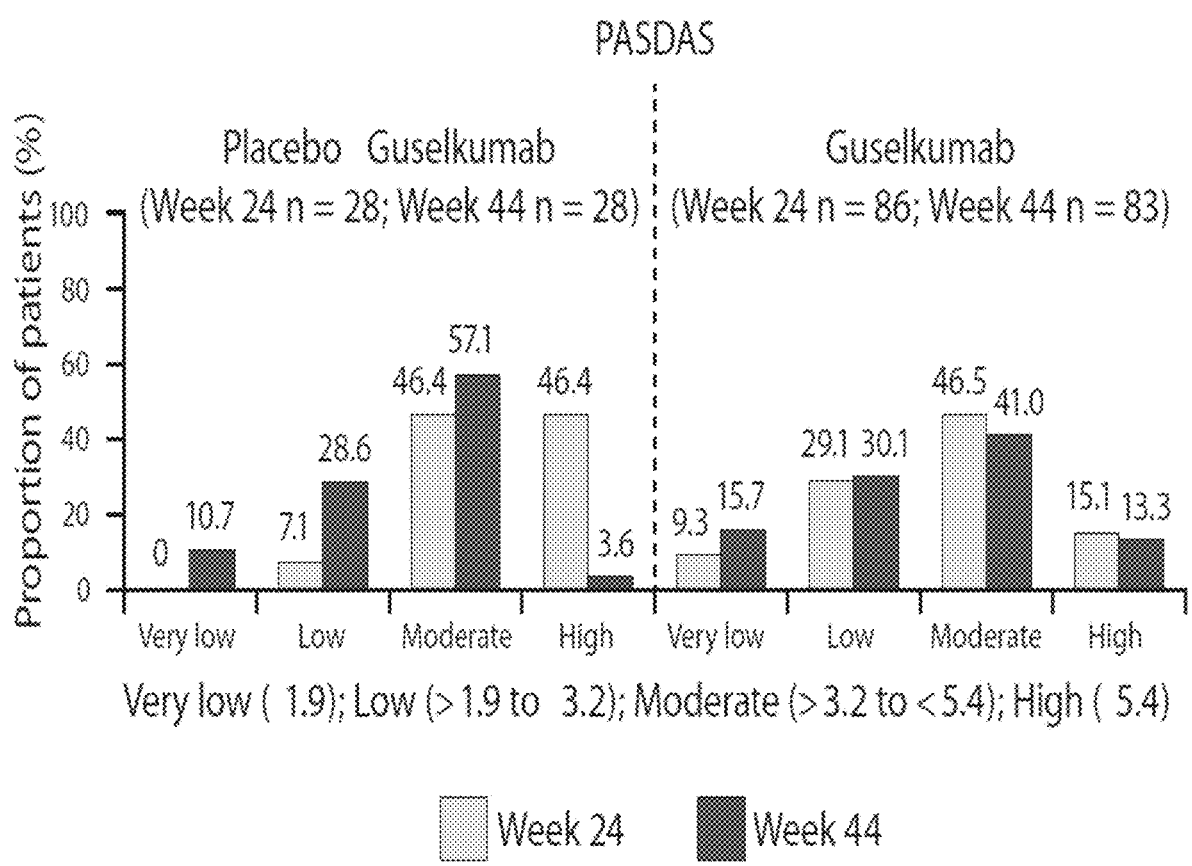
Figure 5D:
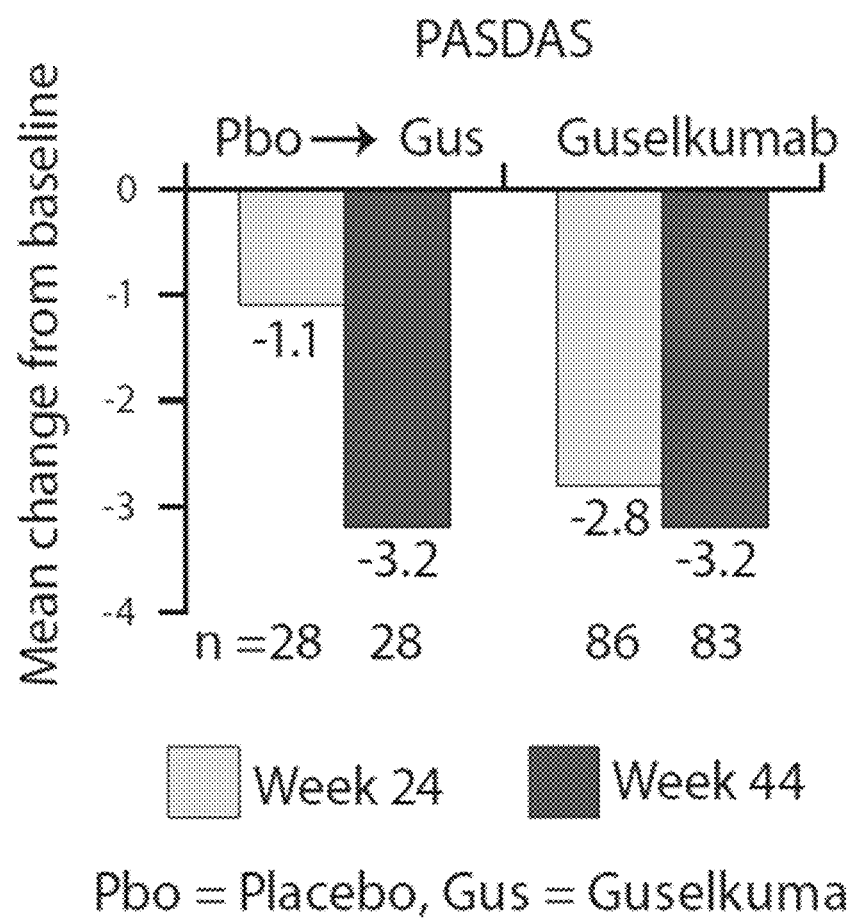
Figure 5E:
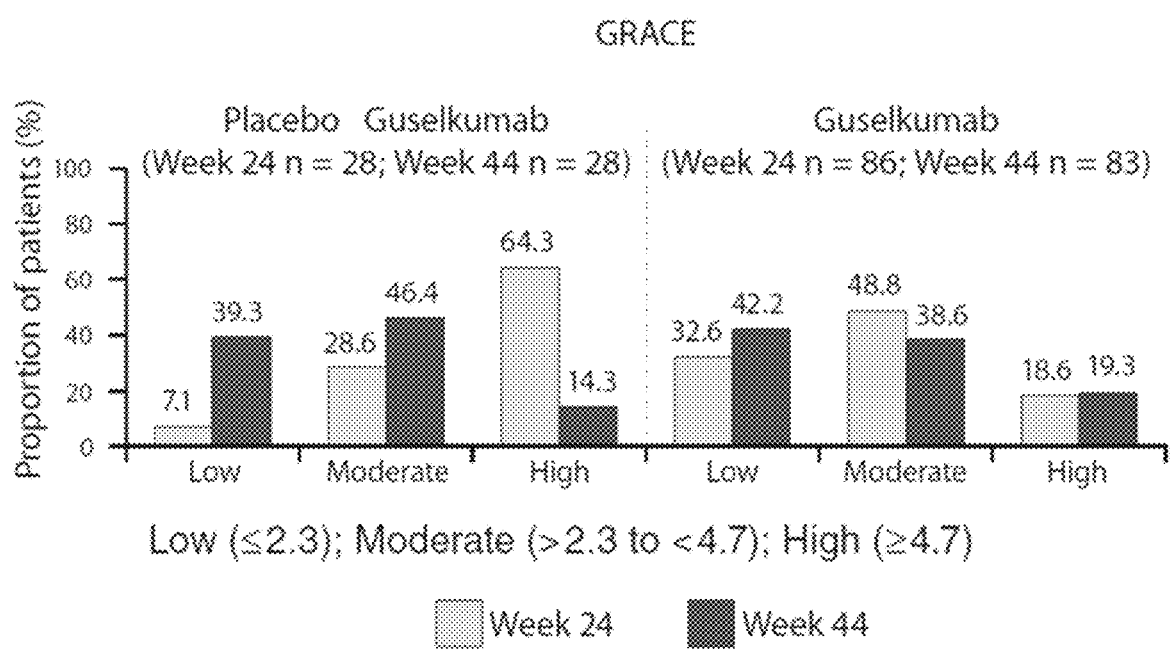
Figure 5F:
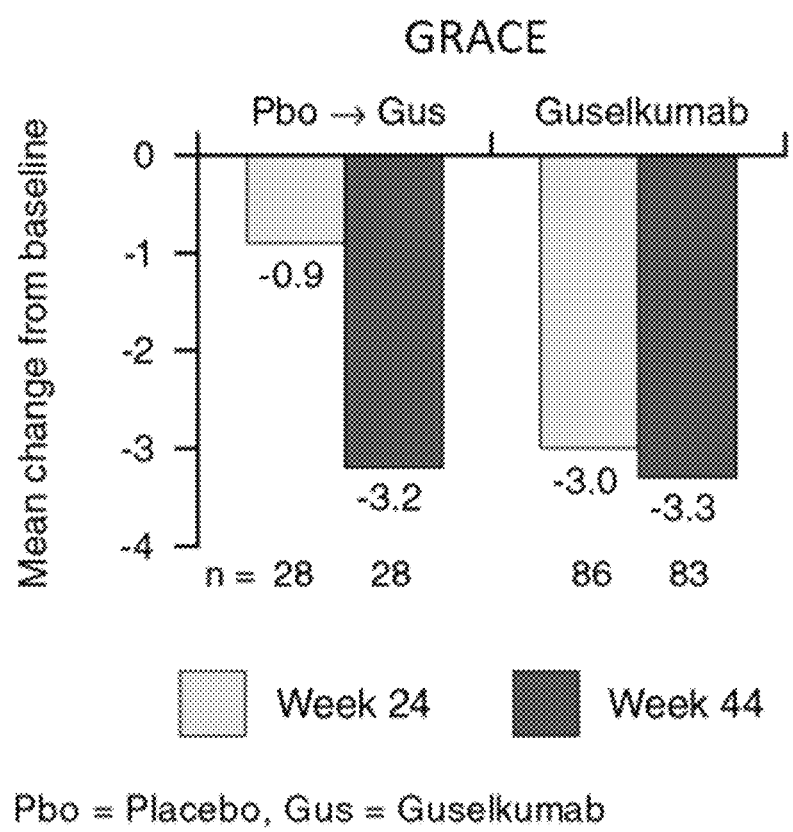
Figure 5G:
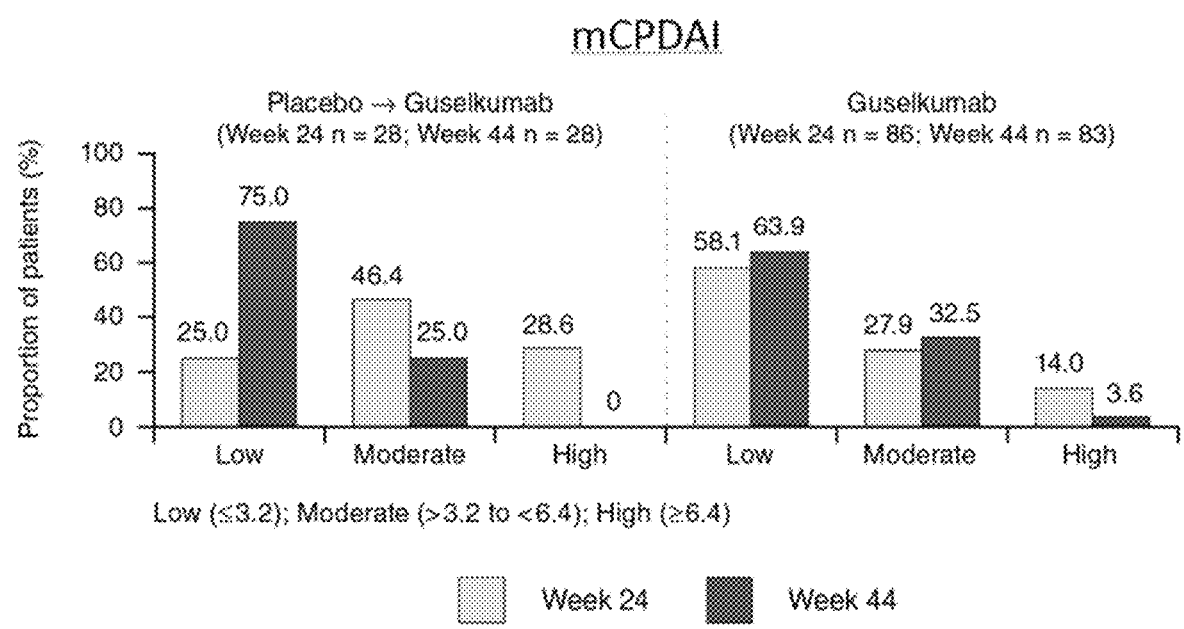
Figure 5H:
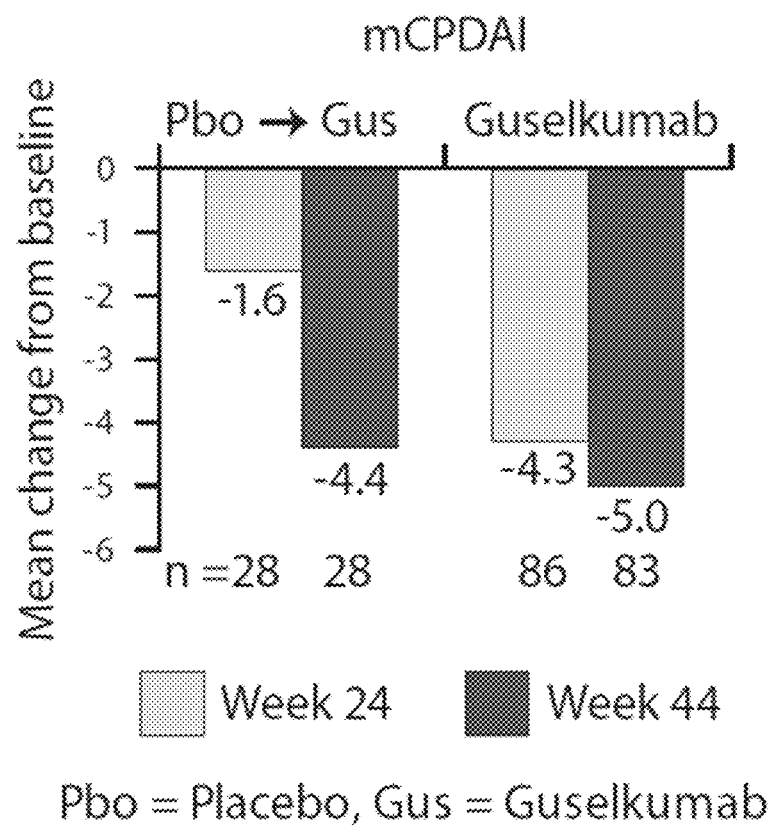
Figure 5I:
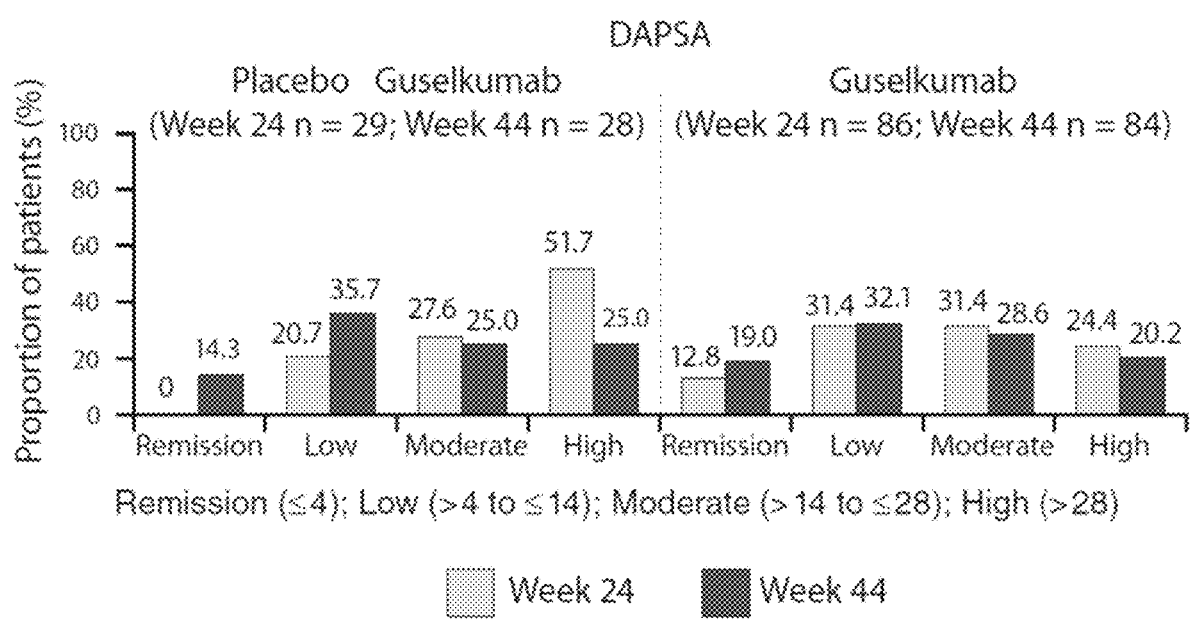
Figure 5J:
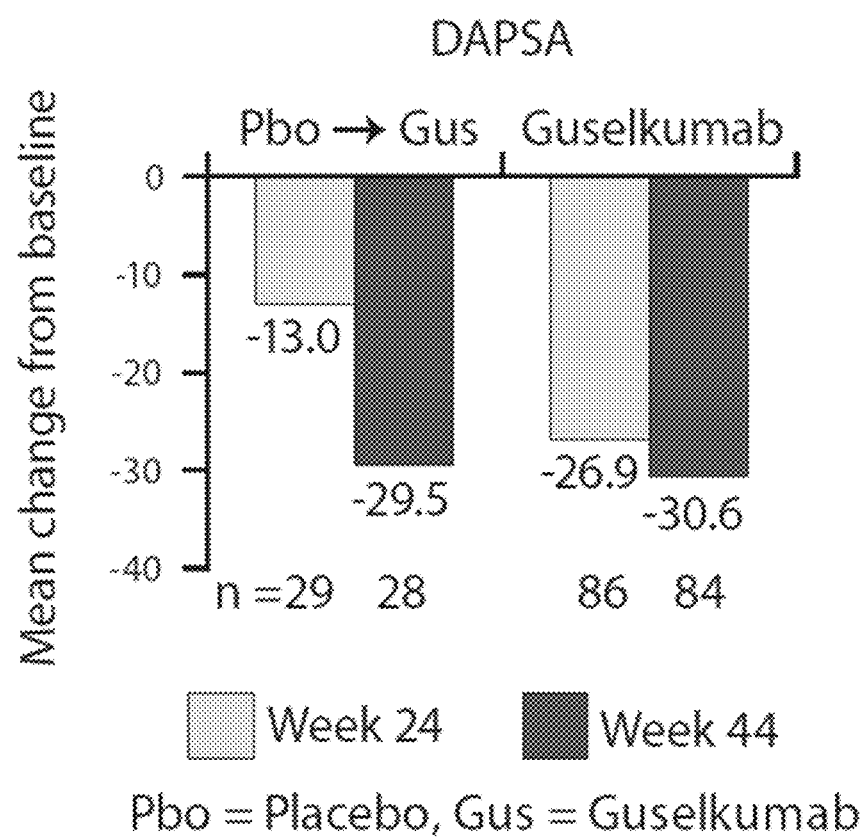

Active-Treatment Period:

In the post-Week 24 efficacy analysis population, observed mean changes in the PsA composite disease activity index scores at Week44 are shown in FIGS. 5D, 5F, 5H, 5J; Week24 data in the same population are included for reference. The improvements afforded by guselkumab at Week24 were sustained through Week44 in guselkumab-randomized patients, and similar improvements were realized in placebo-randomized patients who received guselkumab from Week24 through Week44. Also among patents who crossed over from placebo→guselkumab at Week24, the proportions of patients with low disease activity were higher at Week44 than Week24 prior to guselkumab receipt (i.e., PASDAS very low+low: 39.3% at Week44 vs. 7.1% at Week24; GRACE: 39.3% vs. 7.1%%, respectively; mCP- DAI: 75.0% vs. 25.0%, respectively; and DAPSA remission+low: 50.0% vs. 20.7%, respectively) and were generally consistent with those observed at Week44 among patients receiving guselkumab from Week0 forward (i.e., PASDAS: 28.6% and 30.1%, respectively; GRACE: 39.3% and 42.2%, respectively; mCPDAI: 75.0% and 63.9%, respectively; and DAPSA: 35.7% and 32.1%, respectively; FIGS. 5C, 5E, 5G, 5I). In guselkumab-randomized patients, PASDAS and DAPSA low disease activity response rates were maintained from Week24→Week44 (last on-treatment efficacy assessment, i.e., 29.1%→30.1% for PASDAS and 31.4%→32.1% for DAPSA), while PASDAS very low disease activity (9.3%→15.7%), DAPSA remission (12.8%→19.0%) (FIGS. 5C, 5I), MDA (26.7%→34.5%) and VLDA (7.0%→13.1%) (FIGS. 5A, 5B) response rates all increased from Week24→Week44.

Performance of PsA-Specific Composite Endpoints in Detecting Treatment Effects at Week24

Figure 6A:
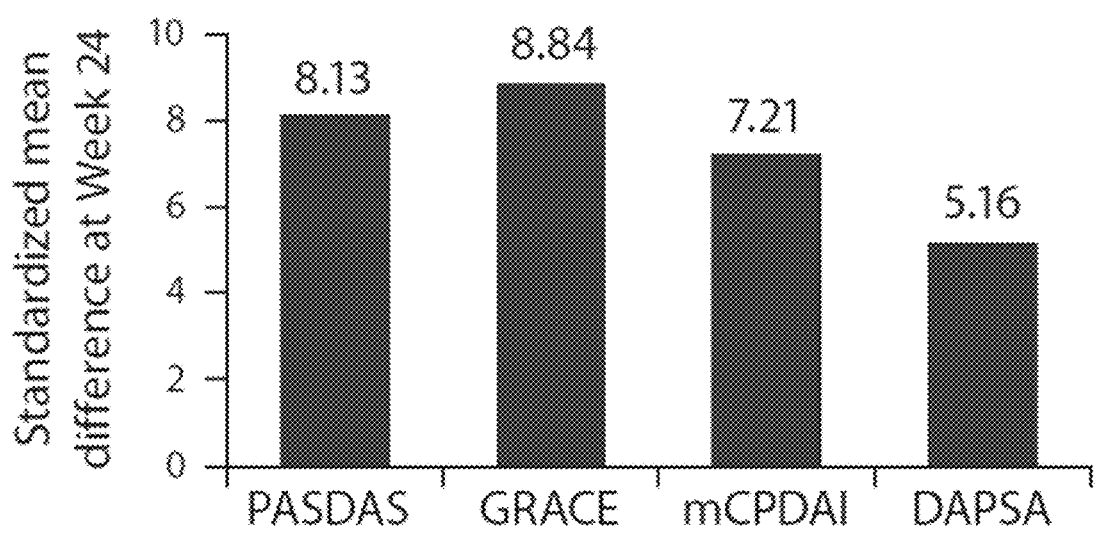
FIGS. 6A-C. Show comparative statistics evaluating guselkumab treatment effects detected at Week 24 according to the PASDAS, GRACE, mCPDAI, and DAPSA PsA-specific composite endpoints: standardized mean difference (6A), effect size (6B), and standardized response mean (6C) (full analysis set; last observation carried forward for missing data). CI=confidence interval, DAPSA=Disease Activity Index for PSoriatic Arthritis, GRACE=Group for Research and Assessment of Psoriasis and Psoriatic Arthritis (GRAppa) Composite scorE, mCPDAI=modified Composite Psoriatic Disease Activity Index, PASDAS=Psoriatic ArthritiS Disease Activity Score, PsA=psoriatic arthritis.
Figure 6B:
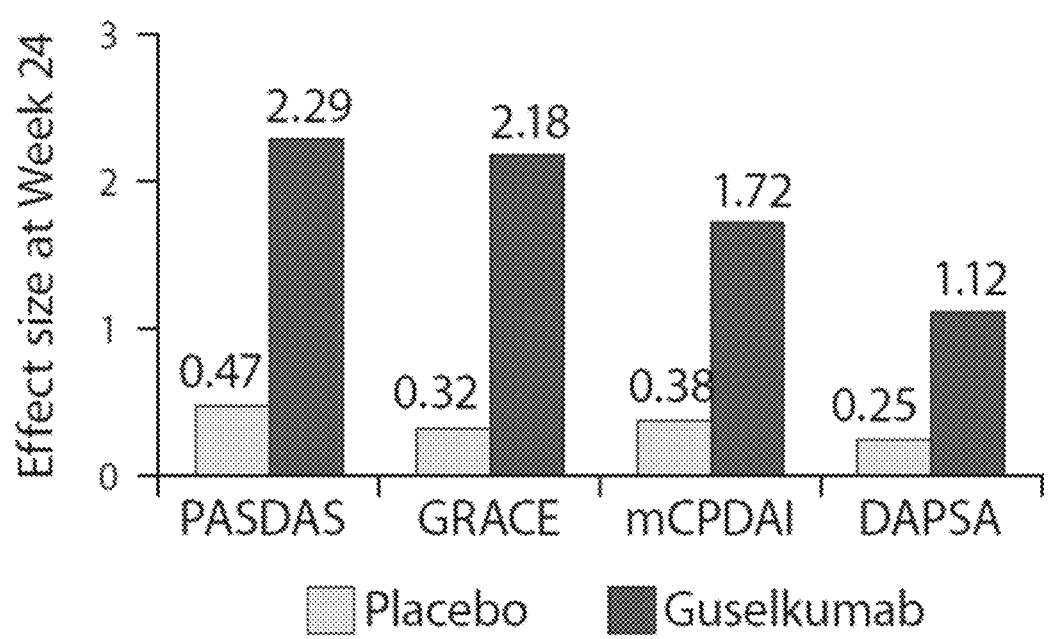
Figure 6C:
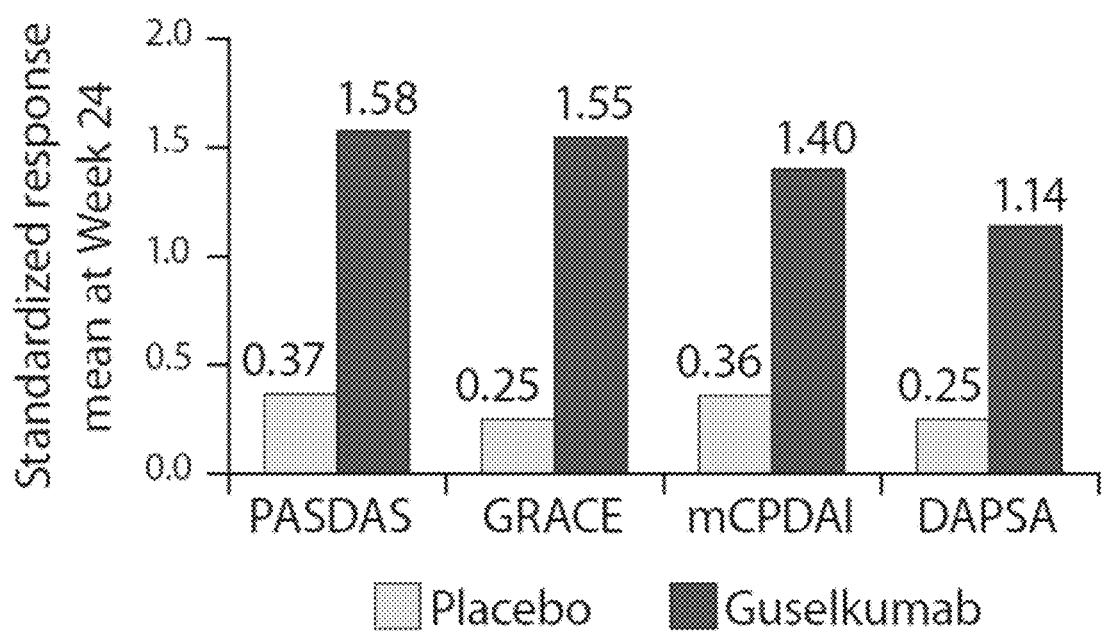

The SMD (5.16-8.13), ES (1.12-2.29), and SRM (1.14-1.58) statistics indicated that guselkumab elicited a large effect in treating the diverse manifestations of PsA compared with placebo, regardless of composite index employed (FIGS. 6A-C). Based on SMD, the PASDAS (8.14) and GRACE (8.84) indices appeared to be more sensitive than mCPDAI (7.21) and DAPSA (5.16) in distinguishing guselkumab treatment effects relative to placebo (FIG. 6A). The ES and SRM statistics also indicated that PASDAS (2.29 and 1.58, respectively) and GRACE Index (2.18 and 1.55, respectively) were more sensitive than mCPDAI (1.72 and 1.40, respectively) and DAPSA (1.12 and 1.14, respectively). in detecting guselkumab treatment effects (FIG. 6B, 6C).

Evaluation of Residual Disease Activity Among Guselkumab-Treated Patients Who Achieved Low/Very Low Disease Activity, Remission, MDA, or VLDA at Week24 Based on PsA Composite Indices The residual skin disease criterion (PASI ≤1) was met in ≥80% of patients achieving PASDAS/GRACE/mCPDAI low or very low disease activity and/or MDA/VLDA; 75.0% of patients achieving DAPSA remission and 70.4% of patients achieving DAPSA low disease activity also demonstrated PASI ≤1. The residual TJC criterion (≤1) was met in 100% of patients achieving PASDAS very low disease activity, DAPSA remission, and/or VLDA; in 87.5% of patients achieving MDA; and in 74.1-79.3% of patients achieving low disease activity based on PASDAS, GRACE, mCPDAI, and DAPSA. The residual SJC criterion (≤1) was met in 100% of patients achieving VLDA; in only ~60% in patients achieving PASDAS very low disease activity, DAPSA remission, and/or MDA; and in only ~30-40% of patients achieving low disease activity based on PASDAS, GRACE, mCPDAI, and DAPSA. The majority of patients achieving low or very low disease activity or remission according to the PsA-specific indices or MDA/VLDA had no enthesitis or dactylitis, but >50% had elevated CRP (>0.287 mg/dL). All patients who achieved PASDAS very low disease activity and ~91% of those who achieved DAPSA remission also met MDA criteria, while <40% also met VLDA criteria (Table S4).

Discussion

Guselkumab has demonstrated efficacy in a Phase 2 trial of patients with active PsA and ≥3% BSA affected by psoriasis (Deodhar A et al, Lancet. 2018, 391:2213-24). In this report of the same trial, guselkumab treatment effects were assessed using composite indices. Guselkumab significantly decreased PASDAS/GRACE/mCPDAI/DAPSA scores vs. placebo, and significantly more guselkumab-than placebo-treated patients achieved MDA and low disease activity states. Overall, PASDAS/GRACE were more sensitive than mCPDAI/DAPSA at detecting treatment effect.

The MDA and VLDA assess joint, skin, and entheseal disease in conjunction with physical function; both be used as response criteria (defining low and very low disease activity, respectively) and provide treatment targets. The PASDAS and GRACE were developed using longitudinal observational data derived from a large international cohort of PsA patients (Helliwell 2013). The PASDAS more heavily weights the patient and physician global assessments than it does joint, skin, dactylitis, enthesitis, acute-phase response, and HRQoL domains, while the GRACE places equal emphasis on each of its domains (joints, skin, function, QoL, global assessments). The domain-based mCPDAI, which assesses axial and peripheral joints, skin, entheses, and dactylitis, employs predefined cutoffs to categorize disease severity that were derived from published literature and expert consensus, while the DAPSA was developed from a clinical cohort of PsA patients to assess joint disease, acute-phase response, and patient assessments of pain and overall disease activity. In this study, the aforementioned PsA-specific indices were validated using the SF-36 PCS score as an anchor, which may be partly circular given that it is a component of the PASDAS. Results showed that the largest improvements in SF-36 PCS scores occurred in patients with remitted/very low/low disease activity according to each index at Week24, and these improvements were significantly higher than those observed in patients with moderate or high disease activity at Week24. Of note, the PASDAS, GRACE and DAPSA composite measures also were externally validated in PsA using radiographic data from the golimumab GO-REVEAL PsA trial. In that analysis, each index was able to differentiate the progression of structural damage of peripheral joints in relation to disease outcome (Helliwell P S et al, Arthritis Care Res 2018, 70:797-800).

As reported herein, additional efficacy assessments in the guselkumab Phase 2 PsA study demonstrated that guselkumab significantly decreased disease activity from Week0→Week24 relative to placebo based on the MDA, VLDA, PASDAS, GRACE, mCPDAI, and DAPSA. Additionally, significantly more guselkumab- than placebo-treated patients achieved a state of low disease activity according to each of the PsA-specific composite indices. Improvements in disease activity were maintained through Week44 in guselkumab-randomized patients and were observed from Week24→Week44 in placebo→guselkumab patients. Findings were consistent with the trial's primary efficacy endpoint (i.e., Week24 ACR20 response: 58% vs. 18%; p<0.0001) (Deodhar 2018), as well as for the general composite measures of disease activity evaluated in this trial (MDA/VLDA). It is important to note that response rates based on the more stringent of the criteria, e.g., VLDA, PASDAS very low disease activity, and DAPSA remission, were further improved beyond Week24 in patients who continued to receive guselkumab (FIGS. 5A-J).

Based on SMD, ES, and SRM, the PASDAS and AMDF-based GRACE indices appear to be more sensitive than the mCPDAI and DAPSA indices in detecting changes in disease activity afforded by guselkumab treatment and distinguishing these effects from those of placebo. Consistently, a previous analysis utilizing data from the golimumab GO-REVEAL trial in PsA indicated that PASDAS and AMDF demonstrated larger effect sizes than mCPDAI and DAPSA (Helliwell 2014). The PASDAS is a weighted measure encompassing a wider spectrum of disease manifestations than, for example, the largely articular DAPSA, and this may account for its larger effect size. The PASDAS was also derived from real patient data using regression analyses, and such methodology is likely to result on more emphasis (weights) being given to domains that show the greatest changes. Both the GRACE and CPDAI are modular measures and, despite covering many important domains, their modular construction may inhibit their responsiveness. It should also be remembered that most patients in this study had polyarticular disease and were treated with a drug that has demonstrated high levels of clinical efficacy; in other circumstances the relative performance of these composite indices may be different.

In terms of residual disease activity, >70% of patients who achieved low, very low, or remitted disease activity based on PASDAS, GRACE, mCPDAI, DAPSA, and MDA/VLDA indices after guselkumab treatment demonstrated little residual skin disease, enthesitis, dactylitis, or tender joints. Consistent results were obtained in previous determinations based on the golimumab GO-REVEAL trial (Helliwell 2014). However, SJC >1 was observed in more than a third of patients achieving PASDAS very low disease activity, DAPSA remission, or MDA and in a majority of patients achieving PASDAS, GRACE, mCPDAI and DAPSA low disease activity. Further, despite achieving remission/low disease activity states, most of these patients still had elevated CRP levels, indicating incomplete resolution of chronic inflammation. Clearly, none of these composite minimal targets represent total abrogation of disease activity.

Among all composite indices evaluated, VLDA appears to represent the most stringent (achieved by only 13.1% of guselkumab-treated patients at Week44). Achievement of VLDA, however, resulted in the least amount residual disease activity across all aspects of disease evaluated other than CRP. While the small number of patients achieving VLDA in this study should be noted, consistent results were recently reported based on a retrospective analysis of 347 patients who received standard or biological DMARDS in either the Tight Control of PsA (TICOPA) study or an observational cohort study (Coates L C et al, Arthritis Rheumatol 2018, 70:345-355). Herein, all patients achieving PASDAS very low disease activity and 20/22 (90.9%) achieving DAPSA remission also achieved MDA, while 15/23 (65.2%) patients who met the MDA criteria did not achieve PASDAS very low disease activity and 13/23 (56.5%) did not meet the DAPSA remission criteria, suggesting PASDAS very low disease activity and DAPSA remission criteria are more stringent and difficult to achieve than MDA.

Future challenges for composite measures will be to strike the correct balance between comprehensiveness and feasibility, particularly in the clinic. Composite indices such as the PASDAS and GRACE are complex and time consuming to fulfill, yet it could be argued that complete evaluation of any patient with PsA requires assessment of all clinical domains. If it is worth collecting the additional data for some of these composite indices, then we need to be clear about the benefit. In the clinic, 'simply' collecting the data required for the DAPSA will encourage incomplete assessment and could give a false impression of overall disease activity. Should the new composite indices only be used in clinical trials? Currently, the answer is in the affirmative (Coates 2018a), but with further use and evolution, it is possible that a 'short-hand' version can be developed for clinic use. Outside of dedicated centers, the use of composite measures might be limited to those patients exhibiting more complex clinical manifestations, while those with "oligosymptomatic" manifestations might readily be managed using conventional tools.

Regarding limitations, the current analyses are hampered by the small size of the Phase 2 trial from which the data derive. Additionally, the SF-36 PCS score is a component of PASDAS, and thus was not an independent measure in PASDAS validation. The evaluation of residual disease is also limited by the small number of patients achieving low/very low/remitted disease activity.

In conclusion, regardless of the PsA-specific composite index employed, guselkumab significantly improved disease activity through Week24; efficacy was well-maintained through Week44. Consistent with results previously reported (Deodhar A et al, Lancet. 2018, 391:2213-24), these findings suggest guselkumab effectively treats diverse clinical presentations of PsA and achieves clinically meaningful therapeutic targets such as low/minimal disease activity or remission. The composite scores assessed are not uniform in either their responses or the disease domains included, indicating that choice of composite score in clinical trials and in clinic requires careful consideration to optimize feasibility and performance.

ABBREVIATIONS AND ACRONYMS

AE adverse event
BCC basal cell carcinoma
BMI body mass index
BSA body surface area
DLQI Dermatology Life Quality Index
f-PGA Fingernail Physician's Global Assessment
hf-PGA Physician's Global Assessment of Hands and/or Feet
HRQoL health-related quality of life
IGA Investigator's Global Assessment
IL interleukin
NAPSI Nail Psoriasis Area and Severity Index
NMSC nonmelanoma skin cancer
PASI Psoriasis Area and Severity Index
PRO patient-reported outcome
PSSD Psoriasis Sign and Symptom Diary
SAE serious adverse event
ss-IGA Scalp-Specific Investigator's Global Assessment
TNFα-inhibitor tumor necrosis factor-α inhibitor Tables

TABLE 1

Summary of baseline patient characteristics (FAS)

|  | Placebo | Guselkumab 100 mg | Total |
| --- | --- | --- | --- |
| Number of patients | 49 | 100 | 149 |
| Age (years) | 44.2 (12.43) | 47.4 (12.83) | 46.3 (12.75) |
| Male, n (%) | 24 (49.0) | 52 (52.0) | 76 (51.0) |
| White, n (%) | 49 (100) | 100 (100) | 149 (100) |
| Body weight (kg) | 86.3 (20.52) | 84.4 (21.41) | 85.0 (21.07) |

TABLE 1-continued

Summary of baseline patient characteristics (FAS)

|  | Placebo | Guselkumab 100 mg | Total |
|---|---|---|---|
| PsA duration (years) | 6.87 (7.24) | 6.98 (7.23) | 6.94 (7.21) |
| No. of swollen joints (0-66) | 10.6 (7.51) | 11.9 (7.60) | 11.5 (7.57) |
| No. of tender joints (0-68) | 20.1 (12.45) | 20.7 (12.16) | 20.5 (12.22) |
| Patient's assessment of pain (0-100 mm VAS) | 61.9 (20.15) | 62.1 (21.53) | 62.0 (21.01) |
| Patient's global assessment of disease activity (arthritis, 0-100 mm VAS) | 64.7 (20.09) | 67.0 (20.63) | 66.2 (20.41) |
| Physician's global assessment of disease activity (0-100 mm VAS) | 61.9 (15.86) | 63.2 (16.76) | 62.8 (16.43) |
| HAQ-DI score (0-3) | 1.34 (0.54) | 1.42 (0.62) | 1.39 (0.60) |
| CRP (mg/dL), median (IQR) | 0.9 (0.4, 2.0) | 0.9 (0.5, 1.8) | 0.9 (0.4, 1.9) |
| BSA, n (%) | 13.6 (12.53) | 17.2 (15.57) | 16.0 (14.70) |
| PASI score (0-72)[a] | 9.9 (7.98) | 12.0 (10.52) | 11.3 (9.78) |
| Patients with enthesitis (per LEI), n (%) | 31 (63.3) | 76 (76.0) | 107 (71.8) |
| Enthesitis score (1-6)[b] | 2.6 (1.48) | 2.7 (1.54) | 2.7 (1.52) |
| Patients with dactylitis, n (%) | 23 (46.9) | 58 (58.0) | 81 (54.4) |
| Dactylitis score (1-60)[c] | 3.9 (3.01) | 6.5 (6.15) | 5.7 (5.55) |
| SF-36 | | | |
| PCS score | 34.4 (8.01) | 33.5 (7.09) | 33.8 (7.39) |
| MCS score | 46.0 (12.52) | 43.3 (11.48) | 44.2 (11.86) |
| Patients with prior use of, n (%) | | | |
| Anti-TNFα agent | 4 (8.2) | 9 (9.0) | 13 (8.7) |
| DMARDs | 41 (83.7) | 90 (90.0) | 131 (87.9) |
| Patients receiving at baseline, n (%) | | | |
| Methotrexate | 19 (38.8) | 47 (47.0) | 66 (44.3) |
| Dose (mg/week) | 16.1 (3.57) | 15.1 (4.20) | 15.4 (4.03) |
| Oral corticosteroids | 8 (16.3) | 12 (12.0) | 20 (13.4) |
| Dose equivalent to prednisone (mg/day) | 5.9 (1.86) | 7.8 (2.57) | 7.0 (2.44) |
| NSAIDs | 36 (73.5) | 70 (70.0) | 106 (71.1) |

Data presented are mean (SD) unless noted otherwise.
[a]Among 146 patients with PASI measurements at baseline (placebo, n = 48; guselkumab, n = 98)
[b]Among 107 patients with enthesitis at baseline (placebo, n = 31; guselkumab, n = 76)
[c]Among 81 patients with dactylitis at baseline (placebo, n = 23; guselkumab, n = 58)
BSA—body surface area,
CRP—C-reactive protein,
DMARDs—disease-modifying antirheumatic drugs,
FAS—full analysis set (randomized and treated patients),
HAQ-DI—Health Assessment Questionnaire-Disability Index,
IQR—interquartile range,
LEI—Leeds Enthesitis Index,
MCS—mental component summary,
NSAIDs—nonsteroidal anti-inflammatory drugs,
PASI—Psoriasis Area and Severity Index,
PCS—physical component summary,
PsA—psoriatic arthritis,
SD—standard deviation,
SF-36—36-item Short-Form,
TNF—tumor necrosis factor,
VAS—visual analog scale

TABLE 2

Summary of efficacy findings at Week 24 (mITT/FAS[a])

| Efficacy Endpoint | Placebo | Guselkumab | p value |
|---|---|---|---|
| Number of patients | 49 | 100 | |
| ACR20, n (%)-Primary endpoint | 9 (18.4) | 58 (58.0) | <0.001[b] |
| % difference[b] (95% CI[c]) | | 39.7 (25.3, 54.1) | |
| Risk Ratio (95% CI[c]) | | 3.2 (1.7, 5.9) | |
| ACR20 with MTX at baseline | 5/19 (26.3) | 27/47 (57.4) | |
| ACR20 without MTX at baseline | 4/30 (13.3) | 31/53 (58.5) | |
| ACR20 with prior anti-TNFα exposure | 0/4 (0) | 6/9 (66.7) | |
| ACR20 without prior anti-TNFα exposure | 9/45 (20.0) | 52/91 (57.1) | |
| ACR50, n (%) | 5 (10.2) | 34 (340) | 0.002[b] |
| % difference[b] (95% CI[c]) | | 23.8 (11.3, 36.3) | |
| ACR70, n (%) | 1 (2.0) | 14 (14.0) | 0.023[b,d] |
| % difference[b] (95% CI[c]) | | 12.0 (4.2, 19.9) | |
| PASI75-Major secondary endpoint | 6/48 (12.5) | 77/98 (78.6) | <0.001[b] |
| % difference[b] (95% CI[c]) | | 66.1 (53.8, 78.4) | |

TABLE 2-continued

| Summary of efficacy findings at Week 24 (mITT/FAS[a]) | | | |
|---|---|---|---|
| Efficacy Endpoint | Placebo | Guselkumab | p value |
| PASI90 | 3/48 (6.3) | 65/98 (66.3) | <0.001[b] |
| % difference[b] (95% CI[c]) | | 60.4 (48.9, 71.9) | |
| PASI100 | 3/48 (6.3) | 39/98 (39.8) | <0.001[b] |
| % difference[b] (95% CI[c]) | | 33.6 (21.7, 45.4) | |
| HAQ-DI, mean (SD) change from baseline-Major secondary endpoint | −0.06 (0.530) | −0.42 (0.512) | <0.001[e] |
| LSMean difference (SE)[e] | | −0.31 (0.082) | |
| (95% CI[e]) | | (−0.471, −0.148) | |
| HAQ-DI responders (≥0.3 improvement[31] from baseline, n (%) | 14 (28.6) | 51 (51.0) | 0.011[b] |
| % difference[b] (95% CI[c]) | | 22.2 (6.2, 38.1) | |
| HAQ-DI responders (≥0.3 improvement[32] from baseline, n (%) | 14 (28.6) | 51 (51.0) | 0.011[b,d] |
| % difference[b] (95% CI[c]) | | 22.2 (6.2, 38.1) | |
| Patients with enthesitis at baseline | 31 | 76 | |
| Median (IQR) % change from baseline-Major secondary endpoint | −33.33 (−100.0, 0.0) | −100.00 (−100.0, −10.0) | 0.009[f] |
| Resolved enthesitis, n (%) | 9 (29.0) | 43 (56.6) | 0.012[b] |
| % difference[b] (95% CI[c]) | | 26.7 (7.2, 46.1) | |
| Patients with dactylitis at baseline | 23 | 58 | |
| Median (IQR) % change from baseline-Major secondary endpoint | −33.33 (−66.7, 0.0) | −100.00 (−100.0, −50.0) | <0.001[f] |
| Resolved dactylitis, n (%) | 4 (17.4) | 32 (55.2) | 0.001[b] |
| % difference[b] (95% CI[c]) | | 39.3 (19.4, 59.2) | |
| SF-36, mean (SD) change from baseline | | | |
| PCS score | 0.46 (6.513) | 6.59 (7.465) | <0.001g |
| Difference (95% CI)[g] | | 6.1 (3.7, 8.6) | |
| MCS score | 0.42 (6.737) | 4.95 (9.064) | 0.002[g] |
| Difference (95% CI)[g] | | 4.5 (1.6, 7.4) | |
| MDA[h] achievement, n (%) | 1 (2.0) | 23 (23.0) | 0.001[b] |
| % difference[b] (95% CI[c]) | | 21.2 (12.0, 30.3) | |
| VLDA[i] achievement, n (%) | 0 (0.0) | 6 (6.0) | 0.08[b] |
| % difference[b] (95% CI[c]) | | 6.1 (1.4, 10.8) | |

[a]Randomised patients who received ≥1 administration of guselkumab or placebo and were analyzed per their assigned treatment group regardless of actual treatment received. Patients who met treatment-failure criteria, early escaped, or had missing data (including missing baseline) were considered nonresponders for ACR/MDA response endpoints at and after treatment failure/early escape. For continuous endpoints, patients with missing baseline values were excluded; LOCF methodology was employed to impute post-baseline missing data. For patients who early escaped, data following early escape were considered as missing and were imputed using LOCF methods.
[b]% differences and P values are based on the CMH test.
[c]CIs are based on the Wald statistic.
[d]Derived from post-hoc analysis.
[e]Statistics are based on the MMRM analysis with treatment group, prior anti-TNF use, baseline HAQ-DI score, baseline MTX use (Yes, No), visit week, and an interaction of treatment and visit week as the independent variables in the model.
[f]P values are based on the Wilcoxon rank sum test.
[g]Differences, CIs, and P values derived from an ANOVA.
[h]Patient's global assessment of disease activity on arthritis and psoriasis VAS score was used as one of the seven outcome measures to derive MDA.
[i]Post-hoc analysis.
ACR20/50/70—American College of Rheumatology 20/50/70% improvement,
ANOVA—analysis of variance,
CI—confidence interval,
CMH—Cochran-Mantel-Haenszel,
FAS—full analysis set,
HAQ-DI—Health Assessment Questionnaire-Disability Index,
LEI—Leeds Enthesitis Index,
LOCF—last observation carried forward,
LS—least squares,
MCS—mental component summary,
MDA—minimal disease activity,
mITT—modified intent-to-treat,
MMRM—mixed model for repeated measures,
MTX—methofrexate,
PASI50/75/90/100—Psoriasis Area and Severity Index 50/75/90/100% improvement,
PCS—physical component summary,
SD—standard deviation,
SE—standard error,
SF-36—36-item Short Form,
TNF—tumor necrosis factor,
VLDA—very low disease activity

TABLE 3

Summary of safety results through Week24 and Week 56 (SAS)

| | Through Week 24 (Placebo-controlled period) | | Through Week 56 | | | | | Placebo/ Guselkumab → Ustekinumab |
|---|---|---|---|---|---|---|---|---|
| | | | Placebo | Guselkumab | | Placebo → | | |
| Number of patients | Placebo[a] 49 | Guselkumab[b] 100 | Guselkumab[c] 29 | Guselkumab[d] 100 | Combined 129 | Ustekinumab[e] 17 | 10 | Combined 27 |
| Mean length of follow up (weeks) | 21·0 | 23·3 | 31·3 | 50·5 | 46·2 | 38·1 | 37·9 | 38·0 |
| Mean number of administrations | 3·6 | 3·9 | 3·9 | 6·4 | 5·8 | 3·8 | 3·9 | 3·9 |
| Patients with 1 or more AE(s), n (%) | 16 (32·7) | 36 (36·0) | 5 (17·2) | 46 (46·0) | 51 (39·5) | 8 (47·1) | 3 (30·0) | 11 (40·7) |
| With MTX at baseline | 6/19 (31·6) | 18/47 (38·3) | 2/12 (16·7) | 23/47 (48·9) | 25/59 (42·4) | 2/7 (28·6) | 1/3 (33·3) | 3/10 (30·0) |
| No MTX at baseline | 10/30 (33·3) | 18/53 (34·0) | 3/17 (17·6) | 23/53 (43·4) | 26/70 (37·1) | 6/10 (60·0) | 2/7 (28·6) | 8/17 (47·1) |
| Common AEs (>2% of guselkumab-treated patients through Week56) | | | | | | | | |
| Elevated transaminases[f] | 1 (2·0) | 4 (4·0) | 2 (6·9) | 9 (9·0) | 11 (8·5)[g] | 0 | 1 (10·0) | 1 (3·7) |
| Nasophalyngitis | 5 (10·2) | 6 (6·0) | 0 | 10 (10·0) | 10 (7·8) | 2 (11·8) | 0 | 2 (7·4) |
| Leukopenia/ WBC count decreased | 0 | 5 (5·0) | 1 (3·4) | 6 (6·0) | 7 (5·4)[h] | 0 | 0 | 0 |
| Neutropenia/ neutrophil count decreased | 0 | 5 (5·0)[i] | 0 | 5 (5·0) | 5 (3·9)[i,j] | 0 | 0 | 0 |
| Upper respiratory tract infection | 1 (2·0) | 1 (1·0) | 1 (3·4) | 3 (3·0) | 4 (3·1) | 0 | 0 | 0 |
| Hepatic steatosis | 0 | 1 (1·0) | 0 | 3 (3·0) | 3 (2·3) | 0 | 0 | 0 |
| Patients with 1 or more SAE(s), n (%) | 1 (2·0) | 1 (1·0) | 0 | 6 (6·0) | 6 (4·7) | 0 | 0 | 0 |
| Joint (knee) injury | 1 (2·0) | 0 | 0 | 0 | 0 | 0 | 0 | 0 |
| Myocardial infarction | 0 | 1 (1·0) | 0 | 1 (1·0) | 1 (0·8) | 0 | 0 | 0 |
| Osteoarthritis | 0 | 0 | 0 | 1 (1·0) | 1 (0·8) | 0 | 0 | 0 |
| Pneumonia | 0 | 0 | 0 | 1 (1·0) | 1 (0·8) | 0 | 0 | 0 |
| Pupils unequal | 0 | 0 | 0 | 1 (1·0) | 1 (0·8) | 0 | 0 | 0 |
| Radius fracture | 0 | 0 | 0 | 1 (1·0) | 1 (0·8) | 0 | 0 | 0 |
| Ulcerative keratitis | 0 | 0 | 0 | 1 (1·0) | 1 (0·8) | 0 | 0 | 0 |
| Patients with AE(s) resulting in study drug d/c, n (%) | 0 | 1 (1·0) | 0 | 2 (2·0)[k] | 2 (1·6)[k] | 0 | 1 (10·0)[k] | 1 (3·7)[k] |
| Leukopenia | 0 | 1 (1·0)[l] | 0 | 1 (1·0) | 1 (0·8)[l] | 0 | 0 | 0 |
| Neutropenia | 0 | 1 (1·0)[l] | 0 | 1 (1·0) | 1 (0·8)[l] | 0 | 0 | 0 |
| Pneumonia | 0 | 0 | 0 | 1 (1·0) | 1 (0·8) | 0 | 0 | 0 |
| Osteoarthritis | 0 | 0 | 0 | 0 | 0 | 0 | 1 (10·0) | 1 (3·7) |
| Patients with infections[m], n (%) | 10 (20·4) | 16 (16·0) | 1 (3·4) | 26 (26·0) | 27 (20·9) | 5 (29·4) | 0 | 5 (18·5) |
| Serious infections | 0 | 0 | 0 | 1 (1·0) | 1 (0·8) | 0 | 0 | 0 |
| Infections treated with oral/parenteral antimicrobial agents[n] | 7 (14·3) | 10 (10·0) | 0 | 16 (16·0) | 16 (12·4) | 2 (11·8) | 0 | 2 (7·4) |

TABLE 3-continued

Summary of safety results through Week24 and Week 56 (SAS)

|  | Through Week 24 (Placebo-controlled period) | | Through Week 56 | | | | | |
|---|---|---|---|---|---|---|---|---|
|  | | | Placebo | | Guselkumab | Placebo → Ustekinumab | | Placebo/ Guselkumab → Ustekinumab |
| Number of patients | Placebo[a] 49 | Guselkumab[b] 100 | Guselkumab[c] 29 | Guselkumab[d] 100 | Combined 129 | Ustekinumab[e] 17 | 10 | Combined 27 |
| Patients with injection-site reactions, n (%) | 1 (2·0) | 0 | 0 | 0 | 0 | 0 | 0 | 0 |

[a]Includes all AEs in placebo patients from Week 0 through Week 24; AEs are only counted for the placebo period.
[b]Includes all AEs in guselkumab patients from Week 0 through Week 24 irrespective of early-escape status; AEs for patients who early escaped at Week 16 are only counted through Week 16.
[c]Includes all AEs in placebo patients who crossed over to guselkumab from Week 24 through Week 56;
[d]Includes all AEs in guselkumab patients from Week 0 through Week 56 irrespective of early escape, AEs for patients who early escaped are counted through Week 16.
[e]Includes all AEs in patients who early escaped from Week 16through Week 56.
[f]Includes the following AE preferred terms: alanine aminotransferase increased, aspartate aminotransferase increased, hepatitis, liver abnormal, liver function test function test increased, and transaminases increased.
[g]Six patients were taking concomitant MTX; three events were considered reasonably related to study treatment by the investigator.
[h]Four patients were taking concomitant MTX and three without concomitant MTX. Among the seven patients with AEs of leukopenia/WBC count decreased, two had the lowest leukocyte counts meeting NCI CTCAE Grade 1 and five had leukocyte counts meeting CTCAE Grade 2 criteria.
[i]Among the five patients with neutropenia, four patients also reported leukopenia/WBC count decreased and were included in the seven patients who reported leukopenia/WBC count decreased. One patient had the lowest neutrophil counts meeting NCI CTCAE Grade 1, three met CTCAE Grade 2, and one met CTCAE Grade 3.
[j]Three patients were taking concomitant MTX and two patients were not taking concomitant MTX.
[k]From Week 0 through Week 44 (final study agent injection).
[l]Leukopenia/neutropenia were reported by the same patient, with onset prior to Week 24 and discontinuation after Week 24.
[m]AEs identified by investigators as infections.
[n]Including antibacterial, antifungal, and antiviral agents.
AE—adverse event,
d/c—discontinuation,
MTX—methotrexate,
SAE—serious adverse event,
SAS—safely analysis set (treated patients),
WBC—white blood cell

TABLE S1

Summary of primary endpoint (ACR20 response at week 24) - sensitivity analysis

|  | Placebo | Guselkumab | p value[a] |
|---|---|---|---|
| Full analysis set | 49 | 100 |  |
| Mean ACR20 response-Bayesian analysis[b], % | 18·8 | 58·0 |  |
| % difference (95% Credible Interval[c]) |  | 39·2 |  |
|  |  | (25·4, 52·4) |  |
| Probability[c] of difference > 0 |  | 100 |  |
| Probability[c] of difference > 20% |  | 99·6 |  |
| ACR20 response-Without treatment-failure rules[d], n (%) | 9 (18·4) | 58 (58·0) | <0.001 |
| % difference[a] (95% CI[e]) |  | 39·7 |  |
|  |  | (25·3, 54·1) |  |
| ACR20 response-Observed data[f], n/N (%) | 11/46 (23·9) | 59/97 (60·8) | <0.001 |
| % difference[a] (95% CI[e]) |  | 36·9 |  |
|  |  | (21·4, 52·5) |  |
| ACR20 response-Excluding patients with all ACR components missing at Week 24[g], n/N (%) | 9/46 (19·6) | 58/97 (59·8) | <0.001 |
| % difference[a] (95% CI[e]) |  | 40·2 |  |
|  |  | (25·3, 55·2) |  |

TABLE S1-continued

Summary of primary endpoint (ACR20 response at week 24) - sensitivity analysis

|  | Placebo | Guselkumab | p value[a] |
|---|---|---|---|
| ACR20 response based on IPW estimates[h], n (%) | 9 (18·5) | 58 (58·2) | |
| % difference (95% CI[i]) | | 39·7 (16·1, 61·1) | |
| ACR20 response in per-protocol set[j] | 9/29 (31·0) | 57/86 (66·3) | 0.0010 |

[a] Differences and P values are based on the CMH test unless otherwise specified.
[b] The mean response is the mean of the posterior distribution of placebo and guselkumab groups, respectively.
[c] 95% credible interval and probabilities are calculated using simulations from the posterior distributions of placebo and guselkumab groups.
d ACR20 response is based on imputed values with early escape and missing data rules applied; no treatment failure rules were applied.
[e] The CIs are based on the Wald statistic.
[f] ACR20 response is based on observed values without any data handling rules applied.
[g] ACR20 response is based on imputed values with treatment failure, early escape and missing data rules applied, but excluding patients who had all ACR components missing at Week 24.
[h] ACR20 response is based on IPW estimates without data handling rules applied. Efficacy measurements after early escape or treatment failure were set to missing, and the inclusion probabilities of non-missing data were estimated using a logistic regression model that included covariates of baseline characteristics, treatment assignment, and the last efficacy measurement before the missing value(s).
[i] The CI is based on the 2·5th and 97·5th percentiles from the bootstrap sample distribution of treatment difference.
[j] Per-protocol set includes all randomized patients who completed the Week-24 visit and did not discontinue study agent administration prior to or at Week 24 and did not early escape at Week 16.
ACR20—American College of Rheumatology 20% improvement,
CI—confidence interval,
CMH—Cochran-Mantel-Haenszel,
FAS—full analysis set,
IPW—Inverse Probability Weighting

TABLE S2

Summary of ACR responses at Week 16, Week 24, Week 44, and Week 56 in patients who early escaped to ustekinumab at Week 16 based on observed data in the ustekinumab populations. Data presented are n (%).

| | Placebo → Ustekinumab | | | | Guselkumab → Ustekinumab | | | |
|---|---|---|---|---|---|---|---|---|
| | Week 16 | Week 24 | Week 44 | Week 56 | Week 16 | Week 24 | Week 44 | Week 56 |
| N | 17 | 17 | 16 | 15 | 10 | 10 | 10 | 8 |
| ACR20 | 0 (0·0) | 2 (11·8) | 8 (50·0) | 5 (33·3) | 0 (0·0) | 1 (10·0) | 5 (50·0) | 5 (62·5) |
| ACR50 | 0 (0·0) | 1 (5·9) | 5 (31·3) | 4 (26·7) | 0 (0·0) | 0 (0·0) | 3 (30·0) | 1 (12·5) |
| ACR70 | 0 (0·0) | 1 (5·9) | 2 (12·5) | 3 (20·0) | 0 (0·0) | 0 (0·0) | 1 (10·0) | 1 (12·5) |

ACR20/50/70-American College of Rheumatology 20/50/70% Improvement

Table S3

Summary of efficacy results from Week 24 through Week 44 and Week 56 based on observed data in the post-Week 24 efficacy analysis set. Data presented are n (%) unless noted otherwise.

| | Placebo → Guselkumab[a] | | | Guselkumab[b] | | |
|---|---|---|---|---|---|---|
| Efficacy Endpoint | Week 24 | Week 44 | Week 56 | Week 24 | Week 44 | Week 56 |
| N[c] | 29 | 28 | 27 | 86 | 84 | 83 |
| ACR20 | 9 (31·0) | 21 (75·0) | 22 (81·5) | 57 (66·3) | 65 (77·4) | 61 (73·5) |
| ACR50 | 5 (17·2) | 13 (46·4) | 18 (66·7) | 34 (39·5) | 39 (46·4) | 44 (53·0) |
| ACR70 | 1 (3·4) | 7 (25·0) | 8/28 (28·6) | 14 (16·3) | 22 (26·2) | 27 (32·5) |
| N[c] | 29 | 28 | 27 | 86 | 83 | 82 |
| PASI75 | 6 (20·7) | 23 (82·1) | 22 (81·5) | 71 (82·6) | 75 (90·4) | 70 (85·4) |
| PASI90 | 3 (10·3) | 21 (75·0) | 20 (74·1) | 61 (70·9) | 68 (81·9) | 64 (78·0) |
| PASI100 | 3 (10·3) | 19 (67·9) | 15 (55·6) | 38 (44·2) | 53 (63·9) | 47 (57·3) |
| N[c] | 29 | 28 | 28 | 86 | 84 | 83 |
| Mean (SD) change from baseline in HAQ-DI | −0·19 (0·581) | −0·63 (0·612) | −0·67 (0·558) | −0·46 (0·530) | −0·54 (0·598) | −0·55 (0·621) |
| HAQ-DI responders (≥0.30) | 13 (44·8) | 20 (71·4) | 21 (75·0) | 48 (55·8) | 52 (61·9) | 49 (59·0) |
| HAQ-DI responders (≥0.35) | 13 (44·8) | 20 (71·4) | 21 (75·0) | 48 (55·8) | 52 (61·9) | 49 (59·0) |
| Patients with baseline enthesitis, N | 18 | 17 | 16 | 67 | 66 | 65 |
| Median (IQR) % change from baseline in LEI | −50·0 (−100·0, 0·0) | −100·0 (−100·0, −60·0) | −100·0 (−100·0, −35·0) | −100·0 (−100·0, −50·0) | −100·0 (−100·0, −50·0) | −100·0 (−100·0, −50·0) |

Table S3-continued

Summary of efficacy results from Week 24 through Week 44 and Week 56 based on observed data in the post-Week 24 efficacy analysis set. Data presented are n (%) unless noted otherwise.

| Efficacy Endpoint | Placebo →Guselkumab[a] | | | Guselkumab[b] | | |
|---|---|---|---|---|---|---|
| | Week 24 | Week 44 | Week 56 | Week 24 | Week 44 | Week 56 |
| Enthesitis resolved, n (%) | 6 (33·3) | 9 (52·9) | 10 (62·5) | 41 (61·2) | 41 (62·1) | 46 (70·8) |
| Patients with baseline dactylitis, N | 16 | 16 | 16 | 50 | 49 | 48 |
| Median (IQR) % change from baseline in dactylitis score | −45·0 (−70·8, 0·0) | −100·0 (−100·0, −100·0) | −100·0 (−100·0, −100·0) | −100·0 (−100·0, −80·0) | −100·0 (−100·0 −100·0) | −100·0 (−100·0, −95·0) |
| Dactylitis resolved, n (%) | 3 (18·8) | 14 (87·5) | 15 (93·8) | 30 (60·0) | 39 (79·6) | 36 (75·0) |
| SF-36, mean (SD) change from baseline, N | 28 | 28 | n/a | 86 | 84 | n/a |
| PCS score | 2·13 (7·365) | 8·02 (8·647) | n/a | 7·40 (7·448) | 8·34 (8·783) | n/a |
| MCS score | 0·51 (6·770) | 5·53 (9·013) | n/a | 5·45 (9·081) | 4·56 (9·548) | n/a |
| MDA[d] achievement, n/N (%) | 1/29 (3·4) | 8/28 (28·6) | n/a | 23/86 (26·7) | 29/84 (34·5) | n/a |
| VLDA[d] achievement, n/N (%) | 0/29 (0·0) | 4/28 (14·3) | n/a | 6/86 7·0) | 11/84 (13·1) | n/a |

[a]Includes the placebo patients who crossed over to receive guselkumab at Week 24. Data at Week 24 represent the last assessments prior to receiving guselkumab.
[b]Includes the patients in the guselkumab group who did not early escape at Week 16 and did not discontinue study treatment prior to or at Week 24.
[c]Unless noted otherwise.
[d]Patient's global assessment of disease activity on arthritis and psoriasis VAS score was used as one of the seven outcome measures to derive MDA or VLDA.
ACR20/50/70—American College of Rheumatology 20/50/70% improvement,
HAQ-DI—Health Assessment Questionnaire-Disability Index,
IQR—interquartile range,
MCS—mental component summary,
MDA—minimal disease activity,
n/a—not assessed,
PASI50/75/90/100—Psoriasis Area and Severity Index 50/75/90/100% improvement,
PCS—physical component summary,
SD—standard deviation,
SF-36—36-item Short Form,
VLDA—very low disease activity Table S4

Number (%) of patients meeting residual disease activity criteria among guselkumab-treated patients achieving low disease activity states defined by PsA composite indices at Week 24 (full analysis set;)*

| Measure of residual disease activity | PASI ≤ 1 | TJC ≤ 1 | SJC ≤ 1 | CRP ≤ ULN | LEI = 0 | Dactylitis = 0 | MDA | VLDA |
|---|---|---|---|---|---|---|---|---|
| PASDAS | | | | | | | | |
| Very low (≤1.9); N = 8 | 7 (87.5) | 8 (100.0) | 5 (62.5) | 4 (50.0) | 8 (100.0) | 8 (100.0) | 8 (100.0) | 3 (37.5) |
| Low (>1.9–≤3.2), N = 27 | 22/26 (84.6) | 20 (74.1) | 12 (44.4) | 12 (44.4) | 23 (85.2) | 25 (92.6) | 12 (48.0) | 3 (12.0) |
| GRACE | | | | | | | | |
| Low (≤2.3), N = 29 | 26 (89.7) | 23 (79.3) | 14 (48.3) | 9 (31.0) | 24 (82.8) | 27 (93.1) | 21 (75.0) | 6 (21.4) |
| mCPDAI | | | | | | | | |
| Low (≤3.2), N = 50 | 40 (80.0) | 38 (76.0) | 19 (38.0) | 20 (40.0) | 46 (92.0) | 46 (92.0) | 22 (44.9) | 6 (12.2) |
| DAPSA | | | | | | | | |
| Remission (≤4), N = 12 | 9 (75.0) | 12 (100.0) | 8 (66.7) | 6 (50.0) | 11 (91.7) | 12 (100.0) | 10 (90.9) | 4 (36.4) |
| Low (>4–≤14), N = 28 | 19/27 (70.4) | 22 (78.6) | 10 (35.7) | 11 (39.3) | 22 (78.6) | 22 (78.6) | 12 (44.4) | 2 (7.4) |

Table S4-continued

Number (%) of patients meeting residual disease activity criteria among guselkumab-treated patients achieving low disease activity states defined by PsA composite indices at Week 24 (full analysis set;)*

| Measure of residual disease activity | PASI ≤ 1 | TJC ≤ 1 | SJC ≤ 1 | CRP ≤ ULN | LEI = 0 | Dactylitis = 0 | MDA | VLDA |
|---|---|---|---|---|---|---|---|---|
| MDA, | | | | | | | | |
| N = 23 | 21 (91.3) | 20 (87.0) | 14 (60.9) | 5 (21.7) | 19 (82.6) | 22 (95.7) | — | 6 (26.1%) |
| VLDA, | | | | | | | | |
| N = 6 | 6 (100) | 6 (100) | 6 (100) | 1 (16.7) | 6 (100) | 6 (100) | 6 (100) | — |

*PsA = psoriatic arthritis,
PASI = Psoriatic Area and Severity Index,
TIC = tender joint count,
SIC = swollen joint count,
CRP = C-reactive protein,
ULN = upper limit of normal (0.287 mg/dL),
LEI = Leeds enthesitis index,
MDA = minimal disease activity,
VLDA = very low disease activity,
PASDAS = Psoriatic ArthritiS Disease Activity Score,
GRACE = Group for Research and Assessment of Psoriasis and Psoriatic Arthritis (GRAppa) Composite scorE,
mCPDAI = modified Composite Psoriatic Disease Activity Index,
DAPSA = Disease Activity Index for PSoriatic Arthritis

TABLE S5

Change in Dactylitis Score in ACR20/50 and PASI75 Responders and Non-responders

| | Mean (SD) change from BL in Dactylitis Score at Wk24 | | |
|---|---|---|---|
| | Non-responders | Responders | p-value |
| ACR 20 | −1.76(7.595), n = 21 | −4.94(4.666), n = 36 | 0.044 |
| ACR 50 | −2.44(6.213), n = 36 | −6.05(5.133), n = 21 | 0.027 |
| PAST 75 | −4.00(2.858), n = 13 | −3.70(6.736), n = 44 | 0.924 |

---

What is claimed:

1. A method of treating psoriatic arthritis in a patient in need thereof, wherein the patient showed an inadequate response to or intolerance to standard non-biologic therapies for psoriatic arthritis, the method comprising:
   (i) subcutaneously administering an antibody to IL-23 to the patient at a dose of 100 mg at week 0, a dose of 100 mg at week 4, and a dose of 100 mg every 8 weeks thereafter (q8 w),
   wherein the antibody comprises a light chain variable region and a heavy chain variable region, said light chain variable region comprising: a LCDR1, a LCDR2 and a LCDR3 comprising the amino acid sequences of SEQ ID NO:50, 56 and 73, respectively; and said heavy chain variable region comprising: a HCDR1, a HCDR2 and a HCDR3 comprising the amino acid sequences of SEQ ID NO:5, 20 and 44, respectively; and wherein the antibody is in a composition comprising 100 mg/mL of the antibody, 7.9% (w/v) sucrose, 4.0 mM Histidine, 6.9 mM L-Histidine monohydrochloride monohydrate, and 0.053% (w/v) Polysorbate 80;
   (ii) measuring whether the patient has achieved a statistically significant improvement in disease activity as determined by at least one endpoint of disease improvement selected from the group consisting of: the American College of Rheumatology 20% improvement criteria (ACR20), the American College of Rheumatology 50% improvement criteria (ACR50), the Psoriasis Area and Severity Index 75, 90 and 100 (PASI75/90/100), the American College of Rheumatology 50% and 70% improvement criteria (ACR50/70), Health Assessment Questionnaire Disability Index (HAQ-DI), Leeds enthesitis index (LEI), a dactylitis assessment score (0=absent, 1=mild, 2=moderate, 3=severe), Short Form Health survey (SF-36), mental and physical component summary (MCS and PCS), a minimal disease activity (MDA) criteria score, a Psoriatic ArthritiS Disease Activity Score (PASDAS), GRAppa Composite scorE (GRACE) Index, modified Composite Psoriatic Disease Activity Index (mCPDAI), Disease Activity Index for Psoriatic Arthritis (DAPSA), and the Routine Assessment of Patient Index Data 3 (RAPID3); and
   (iii) determining that the patient is a responder to treatment with the antibody based on the result of the measurement in step (ii).

2. The method of claim 1, wherein ACR20 is measured at week 16 of treatment with the antibody.

3. The method of claim 1, wherein ACR20 is measured at week 24 of treatment with the antibody.

4. The method of claim 1, wherein PASI75/90/100 is measured at week 24 of treatment with the antibody.

5. The method of claim 1, wherein ACR50/70 is measured at week 24 of treatment with the antibody.

6. The method of claim 1, wherein HAQ-DI is measured at week 24 of treatment with the antibody.

7. The method of claim 1, wherein LEI is measured at week 24 of treatment with the antibody.

8. The method of claim 1, wherein the dactylitis assessment score of 0-3 is measured at week 24 of treatment with the antibody.

9. The method of claim 1, wherein SF-36 is measured at week 24 of treatment with the antibody.

10. The method of claim 1, wherein MCS and PCS are measured at week 24 of treatment with the antibody.

11. The method of claim 1, wherein MDA is measured at week 24 of treatment with the antibody.

12. The method of claim 1, wherein PASDAS is measured at week 24 of treatment with the antibody.

13. The method of claim 1, wherein GRACE Index is measured at week 24 of treatment with the antibody.

14. The method of claim 1, wherein mCPDAI is measured at week 24 of treatment with the antibody.

15. The method of claim 1, wherein DAPSA is measured at week 24 of treatment with the antibody.

16. The method of claim 1, wherein RAPID3 is measured at week 24 of treatment with the antibody.

17. The method of claim 1, wherein ACR20, ACR50, ACR70, PASI70, PASI90, PSAI100, MDA, HAQ-DI, LEI/dactylitis, SF-36 PCS, PASDAS, GRACE, mCPDAI, DAPSA, RAPID3 or MCS is measured 16, 20, 24 or 28 weeks after the initial treatment with the antibody.

18. The method of claim 1, wherein the antibody is effective to reduce a symptom of psoriatic arthritis, induce clinical response, induce or maintain clinical remission, inhibit disease progression, or inhibit a disease complication.

19. The method of claim 1, further comprising administering to the patient one or more additional drugs used to treat psoriasis arthritis.

20. The method of claim 19, wherein the one or more additional drugs is selected from the group consisting of: an immunosuppressive agent, a non-steroidal anti-inflammatory drug (NSAID), methotrexate (MTX), an anti-B-cell surface marker antibody, an anti-CD20 antibody, rituximab, a TNF-inhibitor, and a corticosteroid.

21. A method of treating psoriatic arthritis in a patient in need thereof, wherein the patient showed an inadequate response to or intolerance to standard non-biologic therapies for psoriatic arthritis, the method comprising:
   (i) subcutaneously administering an antibody to IL-23 to the patient at a dose of 100 mg at week 0, a dose of 100 mg at week 4 and a dose of 100 mg every 8 weeks thereafter (q8 w),
   wherein the antibody comprises a light chain variable region comprising the amino acid sequence of SEQ ID NO: 116, and a heavy chain variable region comprising the amino acid sequence of SEQ ID NO: 106; and wherein the antibody is in a composition comprising 100 mg/mL of the antibody, 7.9% (w/v) sucrose, 4.0 mM Histidine, 6.9 mM L-Histidine monohydrochloride monohydrate, and 0.053% (w/v) Polysorbate 80;
   (ii) measuring whether the patient achieves a statistically significant improvement in disease activity as determined by at least one endpoint of disease improvement selected from the group consisting of: the American College of Rheumatology 20% improvement criteria (ACR20), the American College of Rheumatology 50% improvement criteria (ACR50), the Psoriasis Area and Severity Index 75, 90 and 100 (PASI75/90/100), the American College of Rheumatology 50% and 70% improvement criteria (ACR50/70), Health Assessment Questionnaire Disability Index (HAQ-DI), Leeds enthesitis index (LEI), a dactylitis assessment score (0=absent, 1=mild, 2=moderate, 3=severe), Short Form Health survey (SF-36), mental and physical component summary (MCS and PCS), a minimal disease activity (MDA) criteria score, a Psoriatic ArthritiS Disease Activity Score (PASDAS), GRAppa Composite scorE (GRACE) Index, modified Composite Psoriatic Disease Activity Index (mCPDAI), Disease Activity Index for Psoriatic Arthritis (DAPSA), and the Routine Assessment of Patient Index Data 3 (RAPID3); and (iii) determining that the patient is a responder to treatment with the antibody based on the result of the measurement in step (ii).

22. The method of claim 21, wherein ACR20 is measured at week 16 of treatment with the antibody.

23. The method of claim 21, wherein ACR20 is measured at week 24 of treatment with the antibody.

24. The method of claim 21, wherein PASI75/90/100 is measured at week 24 of treatment with the antibody.

25. The method of claim 21, wherein ACR50/70 is measured at week 24 of treatment with the antibody.

26. The method of claim 21, wherein HAQ-DI is measured at week 24 of treatment with the antibody.

27. The method of claim 21, wherein LEI is measured at week 24 of treatment with the antibody.

28. The method of claim 21, wherein the dactylitis assessment score of 0-3 is measured at week 24 of treatment with the antibody.

29. The method of claim 21, wherein SF-36 is measured at week 24 of treatment with the antibody.

30. The method of claim 21, wherein MCS and PCS are measured at week 24 of treatment with the antibody.

31. The method of claim 21, wherein MDA is measured at week 24 of treatment with the antibody.

32. The method of claim 21, wherein PASDAS is measured at week 24 of treatment with the antibody.

33. The method of claim 21, wherein GRACE Index is measured at week 24 of treatment with the antibody.

34. The method of claim 21, wherein mCPDAI is measured at week 24 of treatment with the antibody.

35. The method of claim 21, wherein DAPSA is measured at week 24 of treatment with the antibody.

36. The method of claim 21, wherein RAPID3 is measured at week 24 of treatment with the antibody.

37. The method of claim 21, wherein ACR20, ACR50, ACR70, PASI70, PASI90, PSAI100, MDA, HAQ-DI, LEI/dactylitis, SF-36 PCS, PASDAS, GRACE, mCPDAI, DAPSA, RAPID3 or MCS is measured 16, 20, 24 or 28 weeks after the initial treatment with the antibody.

38. The method of claim 21, wherein the antibody is effective to reduce a symptom of psoriatic arthritis, induce clinical response, induce or maintain clinical remission, inhibit disease progression, or inhibit a disease complication.

39. The method of claim 21, further comprising administering to the patient one or more additional drugs used to treat psoriasis arthritis.

40. The method of claim 39, wherein the one or more additional drugs is selected from the group consisting of: an immunosuppressive agent, a non-steroidal anti-inflammatory drug (NSAID), methotrexate (MTX), an anti-B-cell surface marker antibody, an anti-CD20 antibody, rituximab, a TNF-inhibitor, and a corticosteroid.

41. The method of claim 21, wherein the antibody is guselkumab.

* * * * *

SEQUENCE LISTING

<160> NUMBER OF SEQ ID NOS: 148

<210> SEQ ID NO 1
<211> LENGTH: 5
<212> TYPE: PRT
<213> ORGANISM: Homo sapiens

<400> SEQUENCE: 1

Asn Tyr Ala Ile Ser
1               5

<210> SEQ ID NO 2
<211> LENGTH: 5
<212> TYPE: PRT
<213> ORGANISM: Homo sapiens

<400> SEQUENCE: 2

Ser Asn Tyr Ile Ser
1               5

<210> SEQ ID NO 3
<211> LENGTH: 5
<212> TYPE: PRT

```
<213> ORGANISM: Homo sapiens

<400> SEQUENCE: 3

Asn Tyr Trp Ile Ser
1               5

<210> SEQ ID NO 4
<211> LENGTH: 5
<212> TYPE: PRT
<213> ORGANISM: Homo sapiens

<400> SEQUENCE: 4

Ser Tyr Trp Ile Thr
1               5

<210> SEQ ID NO 5
<211> LENGTH: 5
<212> TYPE: PRT
<213> ORGANISM: Homo sapiens

<400> SEQUENCE: 5

Asn Tyr Trp Ile Gly
1               5

<210> SEQ ID NO 6
<211> LENGTH: 5
<212> TYPE: PRT
<213> ORGANISM: Homo sapiens

<400> SEQUENCE: 6

Ser Phe Gly Met Ser
1               5

<210> SEQ ID NO 7
<211> LENGTH: 17
<212> TYPE: PRT
<213> ORGANISM: Homo sapiens

<400> SEQUENCE: 7

Gly Ile Ile Pro Met Phe Gly Tyr Ala Asn Tyr Ala Gln Lys Phe Gln
1               5                   10                  15

Gly

<210> SEQ ID NO 8
<211> LENGTH: 17
<212> TYPE: PRT
<213> ORGANISM: Homo sapiens

<400> SEQUENCE: 8

Gly Ile Ile Pro Val Phe Gly Phe Thr His Tyr Ala Gln Lys Phe Gln
1               5                   10                  15

Gly

<210> SEQ ID NO 9
<211> LENGTH: 17
<212> TYPE: PRT
<213> ORGANISM: Homo sapiens

<400> SEQUENCE: 9

Gly Ile Ile Pro Ile Phe Gly His Ala Asn Tyr Ala Gln Lys Phe Gln
1               5                   10                  15

Gly
```

```
<210> SEQ ID NO 10
<211> LENGTH: 17
<212> TYPE: PRT
<213> ORGANISM: Homo sapiens

<400> SEQUENCE: 10

Ile Ile Ile Pro Pro Ile Gly Asn Ala Trp Tyr Ala Gln Lys Phe Gln
1               5                   10                  15

Gly

<210> SEQ ID NO 11
<211> LENGTH: 17
<212> TYPE: PRT
<213> ORGANISM: Homo sapiens

<400> SEQUENCE: 11

Leu Ile Asp Pro Asn Phe Gly Gly Ala Tyr Tyr Ala Gln Lys Phe Gln
1               5                   10                  15

Gly

<210> SEQ ID NO 12
<211> LENGTH: 17
<212> TYPE: PRT
<213> ORGANISM: Homo sapiens

<400> SEQUENCE: 12

Leu Ile Asp Pro Val Phe Gly Gly Ala Tyr Tyr Ala Gln Lys Phe Gln
1               5                   10                  15

Gly

<210> SEQ ID NO 13
<211> LENGTH: 17
<212> TYPE: PRT
<213> ORGANISM: Homo sapiens

<400> SEQUENCE: 13

Leu Ile Asp Pro Met Phe Gly Gly Ala Tyr Tyr Ala Gln Lys Phe Gln
1               5                   10                  15

Gly

<210> SEQ ID NO 14
<211> LENGTH: 16
<212> TYPE: PRT
<213> ORGANISM: Homo sapiens

<400> SEQUENCE: 14

Ile Asn Ala His Leu Gly Gly Thr Trp Tyr Ala Gln Lys Phe Gln Gly
1               5                   10                  15

<210> SEQ ID NO 15
<211> LENGTH: 17
<212> TYPE: PRT
<213> ORGANISM: Homo sapiens

<400> SEQUENCE: 15

Ile Ser Pro Gly Thr Gly Ile Asn Ala Tyr Tyr Ala Gln Lys Phe Gln
1               5                   10                  15

Gly

<210> SEQ ID NO 16
<211> LENGTH: 17
```

```
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be G, I, or L
<220> FEATURE:
<221> NAME/KEY: unsure
<222> LOCATION: (2)
<223> OTHER INFORMATION: Where Xaa can be I or S
<220> FEATURE:
<221> NAME/KEY: unsure
<222> LOCATION: (3)
<223> OTHER INFORMATION: Where Xaa can be I, P, N, or D
<220> FEATURE:
<221> NAME/KEY: unsure
<222> LOCATION: (4)
<223> OTHER INFORMATION: Where Xaa can be P, G, or A
<220> FEATURE:
<221> NAME/KEY: unsure
<222> LOCATION: (5)
<223> OTHER INFORMATION: Where Xaa can be I, M, P,
<223> OTHER INFORMATION: T, H, N, or V
<220> FEATURE:
<221> NAME/KEY: unsure
<222> LOCATION: (6)
<223> OTHER INFORMATION: Where Xaa can be F, I, G, or L
<220> FEATURE:
<221> NAME/KEY: unsure
<222> LOCATION: (7)
<223> OTHER INFORMATION: Where Xaa can G or I
<220> FEATURE:
<221> NAME/KEY: unsure
<222> LOCATION: (8)
<223> OTHER INFORMATION: Where Xaa can be H, Y, N, or G
<220> FEATURE:
<221> NAME/KEY: unsure
<222> LOCATION: (9)
<223> OTHER INFORMATION: Where Xaa can be A or T
<220> FEATURE:
<221> NAME/KEY: unsure
<222> LOCATION: (10)
<223> OTHER INFORMATION: Where Xaa can be N, W, or Y

<400> SEQUENCE: 16

Xaa Xaa Xaa Xaa Xaa Xaa Xaa Xaa Xaa Xaa Tyr Ala Gln Lys Phe Gln
1               5                   10                  15

Gly

<210> SEQ ID NO 17
<211> LENGTH: 17
<212> TYPE: PRT
<213> ORGANISM: Homo sapiens

<400> SEQUENCE: 17

Trp Ile Arg Pro Gly Asp Ser Asp Thr Arg Tyr Ser Pro Ser Phe Glu
1               5                   10                  15

Gly

<210> SEQ ID NO 18
<211> LENGTH: 19
<212> TYPE: PRT
<213> ORGANISM: Homo sapiens

<400> SEQUENCE: 18

Val Ser Tyr Ile Ser Ser Ser Gly Ser Ser Thr Tyr Tyr Ala Asp Ser
1               5                   10                  15

Val Lys Gly
```

<210> SEQ ID NO 19
<211> LENGTH: 17
<212> TYPE: PRT
<213> ORGANISM: Homo sapiens

<400> SEQUENCE: 19

Ile Ile Asp Pro Ser Asn Ser Tyr Thr Asn Tyr Ser Pro Ser Phe Gln
1               5                   10                  15

Gly

<210> SEQ ID NO 20
<211> LENGTH: 17
<212> TYPE: PRT
<213> ORGANISM: Homo sapiens

<400> SEQUENCE: 20

Ile Ile Asp Pro Ser Asn Ser Tyr Thr Arg Tyr Ser Pro Ser Phe Gln
1               5                   10                  15

Gly

<210> SEQ ID NO 21
<211> LENGTH: 17
<212> TYPE: PRT
<213> ORGANISM: Homo sapiens

<400> SEQUENCE: 21

Ile Ile Asp Pro Ser Asn Ser Tyr Thr Asp Tyr Ser Pro Ser Phe Gln
1               5                   10                  15

Gly

<210> SEQ ID NO 22
<211> LENGTH: 17
<212> TYPE: PRT
<213> ORGANISM: Homo sapiens

<400> SEQUENCE: 22

Ile Ile Ser Pro Thr Gly Ser Val Thr Trp Tyr Ser Pro Ser Phe Gln
1               5                   10                  15

Gly

<210> SEQ ID NO 23
<211> LENGTH: 17
<212> TYPE: PRT
<213> ORGANISM: Homo sapiens

<400> SEQUENCE: 23

Ile Ile Ser Pro Thr Gly Ser Ser Thr Trp Tyr Ser Pro Ser Phe Gln
1               5                   10                  15

Gly

<210> SEQ ID NO 24
<211> LENGTH: 17
<212> TYPE: PRT
<213> ORGANISM: Homo sapiens

<400> SEQUENCE: 24

Phe Ile Ser Pro Asp Gly Ser His Thr Trp Tyr Ser Pro Ser Phe Gln
1               5                   10                  15

Gly

```
<210> SEQ ID NO 25
<211> LENGTH: 17
<212> TYPE: PRT
<213> ORGANISM: Homo sapiens

<400> SEQUENCE: 25

Ile Ile Ser Pro Ser Gly Ser Thr Thr Trp Tyr Ser Pro Ser Phe Gln
1               5                   10                  15

Gly

<210> SEQ ID NO 26
<211> LENGTH: 17
<212> TYPE: PRT
<213> ORGANISM: Homo sapiens

<400> SEQUENCE: 26

Ile Ile Ser Pro Thr Gly Ser Ala Thr Trp Tyr Ser Pro Ser Phe Gln
1               5                   10                  15

Gly

<210> SEQ ID NO 27
<211> LENGTH: 17
<212> TYPE: PRT
<213> ORGANISM: Homo sapiens

<400> SEQUENCE: 27

Ile Ile Asp Pro Val Ser Ser Trp Thr Lys Tyr Ser Pro Ser Phe Gln
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be D or S
<220> FEATURE:
<221> NAME/KEY: unsure
<222> LOCATION: (5)
<223> OTHER INFORMATION: Where Xaa can be S, V, D, or T
<220> FEATURE:
<221> NAME/KEY: unsure
<222> LOCATION: (6)
<223> OTHER INFORMATION: Where Xaa can be N, S, or G
<220> FEATURE:
<221> NAME/KEY: unsure
<222> LOCATION: (8)
<223> OTHER INFORMATION: Where Xaa can be Y, W, T, H, V, S, or A
<220> FEATURE:
<221> NAME/KEY: unsure
<222> LOCATION: (10)
<223> OTHER INFORMATION: Where Xaa can be N, D, R, K, or W

<400> SEQUENCE: 28

Ile Ile Xaa Pro Xaa Xaa Ser Xaa Thr Xaa Tyr Ser Pro Ser Phe Gln
1               5                   10                  15

Gly

<210> SEQ ID NO 29
<211> LENGTH: 17
<212> TYPE: PRT
<213> ORGANISM: Homo sapiens
```

<400> SEQUENCE: 29

Asn Ile Ser Ser Ser Gly Ser Ser Thr Tyr Tyr Ala Asp Ser Val Lys
1               5                   10                  15

Gly

<210> SEQ ID NO 30
<211> LENGTH: 19
<212> TYPE: PRT
<213> ORGANISM: Homo sapiens

<400> SEQUENCE: 30

Asn Ile Glu His Lys Tyr Leu Asn Tyr Ala Thr Tyr Tyr Ala Ala Ser
1               5                   10                  15

Val Lys Gly

<210> SEQ ID NO 31
<211> LENGTH: 19
<212> TYPE: PRT
<213> ORGANISM: Homo sapiens

<400> SEQUENCE: 31

Asn Ile Glu His Lys Phe Met Gly Tyr Thr Thr Tyr Tyr Ala Ala Gly
1               5                   10                  15

Val Lys Gly

<210> SEQ ID NO 32
<211> LENGTH: 19
<212> TYPE: PRT
<213> ORGANISM: Homo sapiens

<400> SEQUENCE: 32

Gly Ile Glu His Lys Tyr Leu Ser Tyr Thr Thr His Tyr Ala Ala Ser
1               5                   10                  15

Val Lys Gly

<210> SEQ ID NO 33
<211> LENGTH: 19
<212> TYPE: PRT
<213> ORGANISM: Homo sapiens

<400> SEQUENCE: 33

Ser Ile Glu His Lys Tyr Thr Gly Tyr Thr Thr Tyr Tyr Ala Ala Pro
1               5                   10                  15

Val Lys Gly

<210> SEQ ID NO 34
<211> LENGTH: 19
<212> TYPE: PRT
<213> ORGANISM: Homo sapiens

<400> SEQUENCE: 34

Gln Ile Glu His Lys Tyr Leu Ser Tyr Thr Thr Leu Tyr Ala Ala Ser
1               5                   10                  15

Val Lys Gly

<210> SEQ ID NO 35
<211> LENGTH: 19
<212> TYPE: PRT
<213> ORGANISM: Homo sapiens

<400> SEQUENCE: 35

```
Ser Ile Glu His Lys Tyr Leu Ser Tyr Thr Thr Phe Tyr Ala Ala Ser
1               5                   10                  15

Val Lys Gly
```

<210> SEQ ID NO 36
<211> LENGTH: 19
<212> TYPE: PRT
<213> ORGANISM: Homo sapiens

<400> SEQUENCE: 36

```
Asn Ile Glu Gly Lys Tyr Thr Ser Tyr Thr Tyr Tyr Ala Ala Ser
1               5                   10                  15

Val Lys Gly
```

<210> SEQ ID NO 37
<211> LENGTH: 19
<212> TYPE: PRT
<213> ORGANISM: Homo sapiens

<400> SEQUENCE: 37

```
Gly Ile Glu His Lys Tyr Leu Ser Tyr Ala Thr Leu Tyr Ala Ala Ser
1               5                   10                  15

Val Lys Gly
```

<210> SEQ ID NO 38
<211> LENGTH: 19
<212> TYPE: PRT
<213> ORGANISM: Homo sapiens

<400> SEQUENCE: 38

```
Asn Ile Glu His Lys Tyr Leu Gly Tyr Ala Thr Val Tyr Ala Ala Ser
1               5                   10                  15

Val Lys Gly
```

<210> SEQ ID NO 39
<211> LENGTH: 19
<212> TYPE: PRT
<213> ORGANISM: Homo sapiens

<400> SEQUENCE: 39

```
Ser Ile Glu His Lys Tyr Leu Ser Tyr Ala Thr Tyr Tyr Ala Ala Gly
1               5                   10                  15

Val Lys Gly
```

<210> SEQ ID NO 40
<211> LENGTH: 8
<212> TYPE: PRT
<213> ORGANISM: Homo sapiens

<400> SEQUENCE: 40

```
Asp Ile Tyr Ala Gly Met Asp Val
1               5
```

<210> SEQ ID NO 41
<211> LENGTH: 18
<212> TYPE: PRT
<213> ORGANISM: Homo sapiens

<400> SEQUENCE: 41

```
Ser Lys Lys Gly Met Tyr Gly Gly Trp Thr Tyr Pro Leu Met Met Phe
1               5                   10                  15
```

Asp Leu

<210> SEQ ID NO 42
<211> LENGTH: 7
<212> TYPE: PRT
<213> ORGANISM: Homo sapiens

<400> SEQUENCE: 42

His Tyr Tyr Gly Met Asp Tyr
1               5

<210> SEQ ID NO 43
<211> LENGTH: 12
<212> TYPE: PRT
<213> ORGANISM: Homo sapiens

<400> SEQUENCE: 43

Gly Thr Phe Trp Ser Phe Gly Asn Tyr Phe Ala Asn
1               5                   10

<210> SEQ ID NO 44
<211> LENGTH: 8
<212> TYPE: PRT
<213> ORGANISM: Homo sapiens

<400> SEQUENCE: 44

Trp Tyr Tyr Lys Pro Phe Asp Val
1               5

<210> SEQ ID NO 45
<211> LENGTH: 12
<212> TYPE: PRT
<213> ORGANISM: Homo sapiens

<400> SEQUENCE: 45

Tyr Trp Gly Thr Pro Tyr Leu Met Gln Phe Asp Asn
1               5                   10

<210> SEQ ID NO 46
<211> LENGTH: 12
<212> TYPE: PRT
<213> ORGANISM: Homo sapiens

<400> SEQUENCE: 46

Arg Ala Ser Gln Ser Val Leu Gly Asn Tyr Leu Ala
1               5                   10

<210> SEQ ID NO 47
<211> LENGTH: 12
<212> TYPE: PRT
<213> ORGANISM: Homo sapiens

<400> SEQUENCE: 47

Arg Ala Ser Gln Ser Val Ser Ser Asn Tyr Leu Ala
1               5                   10

<210> SEQ ID NO 48
<211> LENGTH: 13
<212> TYPE: PRT
<213> ORGANISM: Homo sapiens

<400> SEQUENCE: 48

Ser Gly Ser Ser Ser Asn Ile Gly Ser Tyr Tyr Val Asn
1               5                   10

```
<210> SEQ ID NO 49
<211> LENGTH: 11
<212> TYPE: PRT
<213> ORGANISM: Homo sapiens

<400> SEQUENCE: 49

Arg Ala Ser Gln Ser Ile Phe Tyr Asn Leu Ala
1               5                   10

<210> SEQ ID NO 50
<211> LENGTH: 14
<212> TYPE: PRT
<213> ORGANISM: Homo sapiens

<400> SEQUENCE: 50

Thr Gly Ser Ser Ser Asn Ile Gly Ser Gly Tyr Asp Val His
1               5                   10

<210> SEQ ID NO 51
<211> LENGTH: 14
<212> TYPE: PRT
<213> ORGANISM: Homo sapiens

<400> SEQUENCE: 51

Thr Gly Thr Ser Ser Asp Val Gly Gly Tyr Asn Ser Val Ser
1               5                   10

<210> SEQ ID NO 52
<211> LENGTH: 7
<212> TYPE: PRT
<213> ORGANISM: Homo sapiens

<400> SEQUENCE: 52

Gly Ala Ser Ser Arg Ala Thr
1               5

<210> SEQ ID NO 53
<211> LENGTH: 7
<212> TYPE: PRT
<213> ORGANISM: Homo sapiens

<400> SEQUENCE: 53

Tyr Ala Ser Arg Arg Ala Thr
1               5

<210> SEQ ID NO 54
<211> LENGTH: 7
<212> TYPE: PRT
<213> ORGANISM: Homo sapiens

<400> SEQUENCE: 54

Gly Asn Thr His Arg Pro Ser
1               5

<210> SEQ ID NO 55
<211> LENGTH: 7
<212> TYPE: PRT
<213> ORGANISM: Homo sapiens

<400> SEQUENCE: 55

Gly Ala Ser Asn Arg Ala Thr
1               5
```

```
<210> SEQ ID NO 56
<211> LENGTH: 7
<212> TYPE: PRT
<213> ORGANISM: Homo sapiens

<400> SEQUENCE: 56

Gly Asn Ser Lys Arg Pro Ser
1               5

<210> SEQ ID NO 57
<211> LENGTH: 7
<212> TYPE: PRT
<213> ORGANISM: Homo sapiens

<400> SEQUENCE: 57

Ser Val Ser Ser Arg Pro Ser
1               5

<210> SEQ ID NO 58
<211> LENGTH: 9
<212> TYPE: PRT
<213> ORGANISM: Homo sapiens

<400> SEQUENCE: 58

His Gln Tyr Gly Ser Ile Ser Thr Thr
1               5

<210> SEQ ID NO 59
<211> LENGTH: 9
<212> TYPE: PRT
<213> ORGANISM: Homo sapiens

<400> SEQUENCE: 59

Gln Gln Tyr Ser His Leu Leu Ile Thr
1               5

<210> SEQ ID NO 60
<211> LENGTH: 9
<212> TYPE: PRT
<213> ORGANISM: Homo sapiens

<400> SEQUENCE: 60

Gln Gln Tyr Ser His Ile Ser Leu Thr
1               5

<210> SEQ ID NO 61
<211> LENGTH: 9
<212> TYPE: PRT
<213> ORGANISM: Homo sapiens

<400> SEQUENCE: 61

Gln Gln Phe Ala His Ile Leu Leu Thr
1               5

<210> SEQ ID NO 62
<211> LENGTH: 9
<212> TYPE: PRT
<213> ORGANISM: Homo sapiens

<400> SEQUENCE: 62

Gln Gln Thr Ser Asn Thr Pro Phe Thr
1               5

<210> SEQ ID NO 63
<211> LENGTH: 9
```

```
<212> TYPE: PRT
<213> ORGANISM: Homo sapiens

<400> SEQUENCE: 63

Gln Gln Phe Ile Thr Tyr Leu Pro Thr
1               5

<210> SEQ ID NO 64
<211> LENGTH: 9
<212> TYPE: PRT
<213> ORGANISM: Homo sapiens

<400> SEQUENCE: 64

Gln Gln Asp Ala Leu Ser Pro Phe Thr
1               5

<210> SEQ ID NO 65
<211> LENGTH: 9
<212> TYPE: PRT
<213> ORGANISM: Homo sapiens

<400> SEQUENCE: 65

Gln Gln Asp Arg Gly Thr Pro Phe Thr
1               5

<210> SEQ ID NO 66
<211> LENGTH: 9
<212> TYPE: PRT
<213> ORGANISM: Homo sapiens

<400> SEQUENCE: 66

Gln Gln Ser Leu Asn Ile Pro Phe Thr
1               5

<210> SEQ ID NO 67
<211> LENGTH: 9
<212> TYPE: PRT
<213> ORGANISM: Homo sapiens

<400> SEQUENCE: 67

Gln Gln Asp Thr Ser Ser Pro Phe Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be T, F, D, or S
<220> FEATURE:
<221> NAME/KEY: unsure
<222> LOCATION: (4)
<223> OTHER INFORMATION: Where Xaa can be S, I, A, T, R, or L
<220> FEATURE:
<221> NAME/KEY: unsure
<222> LOCATION: (5)
<223> OTHER INFORMATION: Where Xaa can be N, T, L, S, or G
<220> FEATURE:
<221> NAME/KEY: unsure
<222> LOCATION: (6)
<223> OTHER INFORMATION: Where Xaa can be T, Y, S, or I
<220> FEATURE:
<221> NAME/KEY: unsure
<222> LOCATION: (7)
<223> OTHER INFORMATION: Where Xaa can be P or L
```

```
<220> FEATURE:
<221> NAME/KEY: unsure
<222> LOCATION: (8)
<223> OTHER INFORMATION: Where Xaa can be F or P

<400> SEQUENCE: 68

Gln Gln Xaa Xaa Xaa Xaa Xaa Xaa Phe Thr
1               5                   10

<210> SEQ ID NO 69
<211> LENGTH: 11
<212> TYPE: PRT
<213> ORGANISM: Homo sapiens

<400> SEQUENCE: 69

Gln Thr Tyr Ala Ser Leu Gly Pro Gly Glu Val
1               5                   10

<210> SEQ ID NO 70
<211> LENGTH: 9
<212> TYPE: PRT
<213> ORGANISM: Homo sapiens

<400> SEQUENCE: 70

Gln Gln Tyr Ser Ser Glu Pro Val Thr
1               5

<210> SEQ ID NO 71
<211> LENGTH: 9
<212> TYPE: PRT
<213> ORGANISM: Homo sapiens

<400> SEQUENCE: 71

Ser Ser Trp Thr Pro Ser Ser Val Val
1               5

<210> SEQ ID NO 72
<211> LENGTH: 11
<212> TYPE: PRT
<213> ORGANISM: Homo sapiens

<400> SEQUENCE: 72

Ser Ser Trp Thr Asp Thr Pro Asn Met Ile Val
1               5                   10

<210> SEQ ID NO 73
<211> LENGTH: 11
<212> TYPE: PRT
<213> ORGANISM: Homo sapiens

<400> SEQUENCE: 73

Ala Ser Trp Thr Asp Gly Leu Ser Leu Val Val
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be S or A
<220> FEATURE:
<221> NAME/KEY: unsure
<222> LOCATION: (6)
```

<223> OTHER INFORMATION: Where Xaa can be T or G
<220> FEATURE:
<221> NAME/KEY: unsure
<222> LOCATION: (7)
<223> OTHER INFORMATION: Where Xaa can be P or L
<220> FEATURE:
<221> NAME/KEY: unsure
<222> LOCATION: (8)
<223> OTHER INFORMATION: Where Xaa can be S or N
<220> FEATURE:
<221> NAME/KEY: unsure
<222> LOCATION: (9)
<223> OTHER INFORMATION: Where Xaa can be S, M, or L
<220> FEATURE:
<221> NAME/KEY: unsure
<222> LOCATION: (10)
<223> OTHER INFORMATION: Where Xaa can be I or V

<400> SEQUENCE: 74

Xaa Ser Trp Thr Asp Xaa Xaa Xaa Xaa Xaa Val
1               5                   10

<210> SEQ ID NO 75
<211> LENGTH: 11
<212> TYPE: PRT
<213> ORGANISM: Homo sapiens

<400> SEQUENCE: 75

Ser Ser Tyr Asp Thr Asn Lys Pro Leu Val Val
1               5                   10

<210> SEQ ID NO 76
<211> LENGTH: 11
<212> TYPE: PRT
<213> ORGANISM: Homo sapiens

<400> SEQUENCE: 76

Gly Ser Tyr Asp Val Tyr Gly Arg Phe Tyr Val
1               5                   10

<210> SEQ ID NO 77
<211> LENGTH: 11
<212> TYPE: PRT
<213> ORGANISM: Homo sapiens

<400> SEQUENCE: 77

Ser Ser Tyr Tyr Phe Tyr Leu Gln Arg Ile Val
1               5                   10

<210> SEQ ID NO 78
<211> LENGTH: 11
<212> TYPE: PRT
<213> ORGANISM: Homo sapiens

<400> SEQUENCE: 78

Gln Thr Tyr Tyr Phe Ser Tyr Ser Gly Pro Val
1               5                   10

<210> SEQ ID NO 79
<211> LENGTH: 11
<212> TYPE: PRT
<213> ORGANISM: Homo sapiens

<400> SEQUENCE: 79

Gly Ser Trp Asp Pro Ile Phe Ser Tyr Glu Val
1               5                   10

-continued

```
<210> SEQ ID NO 80
<211> LENGTH: 117
<212> TYPE: PRT
<213> ORGANISM: Homo sapiens

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Gly Tyr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
        115

<210> SEQ ID NO 81
<211> LENGTH: 117
<212> TYPE: PRT
<213> ORGANISM: Homo sapiens

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Phe Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
        115

<210> SEQ ID NO 82
<211> LENGTH: 108
<212> TYPE: PRT
<213> ORGANISM: Homo sapiens

<400> SEQUENCE: 82

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Tyr Gly Ser Ile Ser
                85                  90                  95

Thr Thr Phe Gly Gln Gly Thr Lys Val Glu Ile Lys
                100                 105

<210> SEQ ID NO 83
<211> LENGTH: 108
<212> TYPE: PRT
<213> ORGANISM: Homo sapiens

<400> SEQUENCE: 83

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Ile Ser
                85                  90                  95

Leu Thr Phe Gly Gln Gly Thr Lys Val Glu Ile Lys
                100                 105

<210> SEQ ID NO 84
<211> LENGTH: 108
<212> TYPE: PRT
<213> ORGANISM: Homo sapiens

<400> SEQUENCE: 84

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser His Leu Ile
                85                  90                  95

Ile Thr Phe Gly Gln Gly Thr Lys Val Glu Ile Lys
                100                 105

<210> SEQ ID NO 85
<211> LENGTH: 108
<212> TYPE: PRT
<213> ORGANISM: Homo sapiens

<400> SEQUENCE: 85

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ala His Ile Leu
                85                  90                  95

Leu Thr Phe Gly Gln Gly Thr Lys Val Glu Ile Lys
            100                 105
```

<210> SEQ ID NO 86
<211> LENGTH: 127
<212> TYPE: PRT
<213> ORGANISM: Homo sapiens

<400> SEQUENCE: 86

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Gly Ile Ile Pro Ile Phe Gly His Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
                100                 105                 110

Met Phe Asp Leu Trp Gly Gln Gly Thr Leu Val Thr Val Ser Ser
            115                 120                 125
```

<210> SEQ ID NO 87
<211> LENGTH: 127
<212> TYPE: PRT
<213> ORGANISM: Homo sapiens

<400> SEQUENCE: 87

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Ile Ile Pro Pro Ile Gly Asn Ala Trp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Lys Lys Gly Met Tyr Gly Gly Trp Thr Tyr Pro Leu Met
                100                 105                 110

Met Phe Asp Leu Trp Gly Gln Gly Thr Leu Val Thr Val Ser Ser
            115                 120                 125

<210> SEQ ID NO 88
<211> LENGTH: 127
<212> TYPE: PRT
<213> ORGANISM: Homo sapiens

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
            35                  40                  45

Gly Ile Ser Pro Gly Thr Gly Ile Asn Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
                100                 105                 110

Met Phe Asp Leu Trp Gly Gln Gly Thr Leu Val Thr Val Ser Ser
            115                 120                 125

<210> SEQ ID NO 89
<211> LENGTH: 126
<212> TYPE: PRT
<213> ORGANISM: Homo sapiens

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
            35                  40                  45

Gly Ile Asn Ala His Leu Gly Gly Thr Trp Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Lys Lys Gly Met Tyr Gly Gly Trp Thr Tyr Pro Leu Met Met
                100                 105                 110

Phe Asp Leu Trp Gly Gln Gly Thr Leu Val Thr Val Ser Ser
            115                 120                 125

<210> SEQ ID NO 90
<211> LENGTH: 127
<212> TYPE: PRT
<213> ORGANISM: Homo sapiens

<400> SEQUENCE: 90

Gln Val Gln Leu Val Gln Ser Gly Ala Glu Val Lys Lys Pro Gly Ser
```

```
                1               5                   10                  15
Ser Val Lys Val Ser Cys Lys Ala Ser Gly Gly Thr Phe Ser Ser Asn
                20                  25                  30

Tyr Ile Ser Trp Val Arg Gln Ala Pro Gly Gln Gly Leu Glu Trp Met
            35                  40                  45

Gly Leu Ile Asp Pro Asn Phe Gly Gly Ala Tyr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
                100                 105                 110

Met Phe Asp Leu Trp Gly Gln Gly Thr Leu Val Thr Val Ser Ser
                115                 120                 125

<210> SEQ ID NO 91
<211> LENGTH: 127
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
                20                  25                  30

Tyr Ile Ser Trp Val Arg Gln Ala Pro Gly Gln Gly Leu Glu Trp Met
            35                  40                  45

Gly Leu Ile Asp Pro Val Phe Gly Gly Ala Tyr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
                100                 105                 110

Met Phe Asp Leu Trp Gly Gln Gly Thr Leu Val Thr Val Ser Ser
                115                 120                 125

<210> SEQ ID NO 92
<211> LENGTH: 127
<212> TYPE: PRT
<213> ORGANISM: Homo sapiens

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
                20                  25                  30

Tyr Ile Ser Trp Val Arg Gln Ala Pro Gly Gln Gly Leu Glu Trp Met
            35                  40                  45

Gly Leu Ile Asp Pro Met Phe Gly Gly Ala Tyr Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
            85                  90                  95
Ala Arg Ser Lys Lys Gly Met Tyr Gly Gly Trp Thr Tyr Pro Leu Met
            100                 105                 110
Met Phe Asp Leu Trp Gly Gln Gly Thr Leu Val Thr Val Ser Ser
            115                 120                 125

<210> SEQ ID NO 93
<211> LENGTH: 108
<212> TYPE: PRT
<213> ORGANISM: Homo sapiens

<400> SEQUENCE: 93

Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Thr Tyr Tyr Cys Gln Gln Thr Ser Asn Thr Pro
                85                  90                  95
Phe Thr Phe Gly Gln Gly Thr Lys Val Glu Ile Lys
            100                 105

<210> SEQ ID NO 94
<211> LENGTH: 108
<212> TYPE: PRT
<213> ORGANISM: Homo sapiens

<400> SEQUENCE: 94

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Thr Ser Asn Thr Pro
                85                  90                  95
Phe Thr Phe Gly Gln Gly Thr Lys Val Glu Ile Lys
            100                 105

<210> SEQ ID NO 95
<211> LENGTH: 108
<212> TYPE: PRT
<213> ORGANISM: Homo sapiens

<400> SEQUENCE: 95

Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
```

```
Tyr Leu Ala Trp Tyr Gln Gln Lys Pro Gly Gln Ala Pro Arg Leu Leu
            35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65              70                  75                  80

Pro Glu Asp Phe Ala Val Tyr Tyr Cys Gln Gln Phe Ile Thr Tyr Leu
                85                  90                  95

Pro Thr Phe Gly Gln Gly Thr Lys Val Glu Ile Lys
            100                 105

<210> SEQ ID NO 96
<211> LENGTH: 108
<212> TYPE: PRT
<213> ORGANISM: Homo sapiens

<400> SEQUENCE: 96

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
            35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65              70                  75                  80

Pro Glu Asp Phe Ala Val Tyr Tyr Cys Gln Gln Asp Ala Leu Ser Pro
                85                  90                  95

Phe Thr Phe Gly Gln Gly Thr Lys Val Glu Ile Lys
            100                 105

<210> SEQ ID NO 97
<211> LENGTH: 108
<212> TYPE: PRT
<213> ORGANISM: Homo sapiens

<400> SEQUENCE: 97

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
            35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65              70                  75                  80

Pro Glu Asp Phe Ala Val Tyr Tyr Cys Gln Gln Asp Arg Gly Thr Pro
                85                  90                  95

Phe Thr Phe Gly Gln Gly Thr Lys Val Glu Ile Lys
            100                 105

<210> SEQ ID NO 98
<211> LENGTH: 108
<212> TYPE: PRT
<213> ORGANISM: Homo sapiens
```

<400> SEQUENCE: 98

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Ser Leu Asn Ile Pro
                85                  90                  95

Phe Thr Phe Gly Gln Gly Thr Lys Val Glu Ile Lys
            100                 105

<210> SEQ ID NO 99
<211> LENGTH: 116
<212> TYPE: PRT
<213> ORGANISM: Homo sapiens

<400> SEQUENCE: 99

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Ala Pro Gly Lys Gly Leu Glu Trp Met
        35                  40                  45

Gly Trp Ile Arg Pro Gly Asp Ser Asp Thr Arg Tyr Ser Pro Ser Phe
    50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Tyr Tyr Gly Met Asp Tyr Trp Gly Gln Gly Thr Leu Val
            100                 105                 110

Thr Val Ser Ser
        115

<210> SEQ ID NO 100
<211> LENGTH: 110
<212> TYPE: PRT
<213> ORGANISM: Homo sapiens

<400> SEQUENCE: 100

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Tyr
            20                  25                  30

Tyr Val Asn Trp Tyr Gln Gln Leu Pro Gly Thr Ala Pro Lys Leu Leu
        35                  40                  45

Ile Tyr Gly Asn Thr His Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

-continued

Ser Glu Asp Glu Ala Asp Tyr Tyr Cys Gln Thr Tyr Ala Ser Leu Gly
                85                  90                  95

Pro Gly Glu Val Phe Gly Gly Gly Thr Lys Leu Thr Val Leu
            100                 105                 110

<210> SEQ ID NO 101
<211> LENGTH: 121
<212> TYPE: PRT
<213> ORGANISM: Homo sapiens

<400> SEQUENCE: 101

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile Thr Trp Val Arg Gln Ala Pro Gly Lys Gly Leu Glu Trp Val
        35                  40                  45

Ser Tyr Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Phe Trp Ser Phe Gly Asn Tyr Phe Ala Asn Trp Gly
            100                 105                 110

Gln Gly Thr Leu Val Thr Val Ser Ser
        115                 120

<210> SEQ ID NO 102
<211> LENGTH: 107
<212> TYPE: PRT
<213> ORGANISM: Homo sapiens

<400> SEQUENCE: 102

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Phe Tyr Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Tyr Ser Ser Glu Pro Val
                85                  90                  95

Thr Phe Gly Gln Gly Thr Lys Val Glu Ile Lys
            100                 105

<210> SEQ ID NO 103
<211> LENGTH: 117
<212> TYPE: PRT
<213> ORGANISM: Homo sapiens

<400> SEQUENCE: 103

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr

-continued

```
                20                  25                  30
Trp Ile Gly Trp Val Arg Gln Met Pro Gly Lys Gly Leu Glu Trp Met
            35                  40                  45
Gly Ile Ile Asp Pro Ser Asn Ser Tyr Thr Asn Tyr Ser Pro Ser Phe
 50                      55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
            115

<210> SEQ ID NO 104
<211> LENGTH: 117
<212> TYPE: PRT
<213> ORGANISM: Homo sapiens

<400> SEQUENCE: 104

Gln Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Ser Asn Tyr
                20                  25                  30
Trp Ile Gly Trp Val Arg Gln Met Pro Gly Lys Gly Leu Glu Trp Met
            35                  40                  45
Gly Ile Ile Asp Pro Ser Asn Ser Tyr Thr Asp Tyr Ser Pro Ser Phe
 50                      55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
            115

<210> SEQ ID NO 105
<211> LENGTH: 117
<212> TYPE: PRT
<213> ORGANISM: Homo sapiens

<400> SEQUENCE: 105

Gln Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Ser Asn Tyr
                20                  25                  30
Trp Ile Gly Trp Val Arg Gln Met Pro Gly Lys Gly Leu Glu Trp Met
            35                  40                  45
Gly Ile Ile Asp Pro Ser Asn Ser Tyr Thr Arg Tyr Ser Pro Ser Phe
 50                      55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
```

-continued

```
                    100                 105                 110

Val Thr Val Ser Ser
        115

<210> SEQ ID NO 106
<211> LENGTH: 117
<212> TYPE: PRT
<213> ORGANISM: Homo sapiens

<400> SEQUENCE: 106

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 107
<211> LENGTH: 117
<212> TYPE: PRT
<213> ORGANISM: Homo sapiens

<400> SEQUENCE: 107

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Asp Pro Val Ser Ser Trp Thr Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
        115

<210> SEQ ID NO 108
<211> LENGTH: 117
<212> TYPE: PRT
<213> ORGANISM: Homo sapiens

<400> SEQUENCE: 108

Gln Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Ser Pro Ser Gly Ser Thr Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 109
<211> LENGTH: 117
<212> TYPE: PRT
<213> ORGANISM: Homo sapiens

<400> SEQUENCE: 109

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Phe Ile Ser Pro Asp Gly Ser His Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 110
<211> LENGTH: 117
<212> TYPE: PRT
<213> ORGANISM: Homo sapiens

<400> SEQUENCE: 110

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Ser Pro Thr Gly Ser Val Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Trp Tyr Tyr Lys Pro Phe Asp Val Trp Gly Gln Gly Thr Leu
            100                 105                 110

Val Thr Val Ser Ser
            115

<210> SEQ ID NO 111
<211> LENGTH: 117
<212> TYPE: PRT
<213> ORGANISM: Homo sapiens

<400> SEQUENCE: 111

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Ser Pro Thr Gly Ser Ser Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
            115

<210> SEQ ID NO 112
<211> LENGTH: 117
<212> TYPE: PRT
<213> ORGANISM: Homo sapiens

<400> SEQUENCE: 112

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Ser Pro Thr Gly Ser Ala Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
            115

<210> SEQ ID NO 113
<211> LENGTH: 109
<212> TYPE: PRT
<213> ORGANISM: Homo sapiens

<400> SEQUENCE: 113
```

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ser Ser Trp Thr Pro Ser
                85                  90                  95

Ser Val Val Phe Gly Gly Gly Thr Lys Leu Thr Val Leu
            100                 105

<210> SEQ ID NO 114
<211> LENGTH: 111
<212> TYPE: PRT
<213> ORGANISM: Homo sapiens

<400> SEQUENCE: 114

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ser Ser Trp Thr Asp Thr
                85                  90                  95

Pro Asn Met Ile Val Phe Gly Gly Gly Thr Lys Leu Thr Val Leu
            100                 105                 110

<210> SEQ ID NO 115
<211> LENGTH: 111
<212> TYPE: PRT
<213> ORGANISM: Homo sapiens

<400> SEQUENCE: 115

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 116
<211> LENGTH: 111
<212> TYPE: PRT
<213> ORGANISM: Homo sapiens

<400> SEQUENCE: 116

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
            100                 105                 110

<210> SEQ ID NO 117
<211> LENGTH: 121
<212> TYPE: PRT
<213> ORGANISM: Homo sapiens

<400> SEQUENCE: 117

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Gly Thr Pro Tyr Leu Met Gln Phe Asp Asn Trp Gly
            100                 105                 110

Gln Gly Thr Leu Val Thr Val Ser Ser
            115                 120

<210> SEQ ID NO 118
<211> LENGTH: 123
<212> TYPE: PRT
<213> ORGANISM: Homo sapiens

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Phe Met Gly Tyr Thr Thr Tyr Tyr Ala Ala

```
                    50                  55                  60
Gly Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Arg Tyr Trp Gly Thr Pro Tyr Leu Met Gln Phe Asp Asn
                    100                 105                 110

Trp Gly Gln Gly Thr Leu Val Thr Val Ser Ser
            115                 120
```

<210> SEQ ID NO 119
<211> LENGTH: 123
<212> TYPE: PRT
<213> ORGANISM: Homo sapiens

<400> SEQUENCE: 119

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Glu His Lys Tyr Thr Gly Tyr Thr Thr Tyr Tyr Ala Ala
 50                  55                  60

Pro Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Arg Tyr Trp Gly Thr Pro Tyr Leu Met Gln Phe Asp Asn
                    100                 105                 110

Trp Gly Gln Gly Thr Leu Val Thr Val Ser Ser
            115                 120
```

<210> SEQ ID NO 120
<211> LENGTH: 123
<212> TYPE: PRT
<213> ORGANISM: Homo sapiens

<400> SEQUENCE: 120

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Asn Ile Glu His Lys Tyr Thr Ser Tyr Thr Thr Tyr Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Arg Tyr Trp Gly Thr Pro Tyr Leu Met Gln Phe Asp Asn
                    100                 105                 110

Trp Gly Gln Gly Thr Leu Val Thr Val Ser Ser
            115                 120
```

```
<210> SEQ ID NO 121
<211> LENGTH: 123
<212> TYPE: PRT
<213> ORGANISM: Homo sapiens

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Leu Asn Tyr Ala Thr Tyr Tyr Ala Ala
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 122
<211> LENGTH: 123
<212> TYPE: PRT
<213> ORGANISM: Homo sapiens

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Leu Gly Tyr Ala Thr Val Tyr Ala Ala
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 123
<211> LENGTH: 123
<212> TYPE: PRT
<213> ORGANISM: Homo sapiens

<400> SEQUENCE: 123

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45
```

```
Ser Ser Ile Glu His Lys Tyr Leu Ser Tyr Ala Thr Tyr Tyr Ala Ala
        50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
                115                 120

<210> SEQ ID NO 124
<211> LENGTH: 123
<212> TYPE: PRT
<213> ORGANISM: Homo sapiens

<400> SEQUENCE: 124

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Ser Ile Glu His Lys Tyr Leu Ser Tyr Thr Thr Phe Tyr Ala Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
                115                 120

<210> SEQ ID NO 125
<211> LENGTH: 123
<212> TYPE: PRT
<213> ORGANISM: Homo sapiens

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Gly Ile Glu His Lys Tyr Leu Ser Tyr Thr Thr His Tyr Ala Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
                115                 120
```

<210> SEQ ID NO 126
<211> LENGTH: 123
<212> TYPE: PRT
<213> ORGANISM: Homo sapiens

<400> SEQUENCE: 126

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Gln Ile Glu His Lys Tyr Leu Ser Tyr Thr Thr Leu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 127
<211> LENGTH: 123
<212> TYPE: PRT
<213> ORGANISM: Homo sapiens

<400> SEQUENCE: 127

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Gly Ile Glu His Lys Tyr Leu Ser Tyr Ala Thr Leu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 128
<211> LENGTH: 111
<212> TYPE: PRT
<213> ORGANISM: Homo sapiens

<400> SEQUENCE: 128

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
                35                  40                  45

Met Ile Tyr Ser Val Ser Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Thr Asn
                 85                  90                  95

Lys Pro Leu Val Val Phe Gly Gly Gly Thr Lys Leu Thr Val Leu
                100                 105                 110

<210> SEQ ID NO 129
<211> LENGTH: 111
<212> TYPE: PRT
<213> ORGANISM: Homo sapiens

<400> SEQUENCE: 129

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
                35                  40                  45

Met Ile Tyr Ser Val Ser Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Tyr Phe Tyr
                 85                  90                  95

Leu Gln Arg Ile Val Phe Gly Gly Gly Thr Lys Leu Thr Val Leu
                100                 105                 110

<210> SEQ ID NO 130
<211> LENGTH: 111
<212> TYPE: PRT
<213> ORGANISM: Homo sapiens

<400> SEQUENCE: 130

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
                35                  40                  45

Met Ile Tyr Ser Val Ser Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Thr Tyr Tyr Phe Ser
                 85                  90                  95

Tyr Ser Gly Pro Val Phe Gly Gly Gly Thr Lys Leu Thr Val Leu
                100                 105                 110

<210> SEQ ID NO 131
<211> LENGTH: 111
<212> TYPE: PRT
<213> ORGANISM: Homo sapiens -continued

<400> SEQUENCE: 131

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Ser Val Ser Ser Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Val Tyr
                85                  90                  95

Gly Arg Phe Tyr Val Phe Gly Gly Gly Thr Lys Leu Thr Val Leu
            100                 105                 110

<210> SEQ ID NO 132
<211> LENGTH: 111
<212> TYPE: PRT
<213> ORGANISM: Homo sapiens

<400> SEQUENCE: 132

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Ser Val Ser Ser Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Trp Asp Pro Ile
                85                  90                  95

Phe Ser Tyr Glu Val Phe Gly Gly Gly Thr Lys Leu Thr Val Leu
            100                 105                 110

<210> SEQ ID NO 133
<211> LENGTH: 381
<212> TYPE: DNA
<213> ORGANISM: Homo sapiens

<400> SEQUENCE: 133
caggtgcagc tggtgcagtc tggggctgag gtgaagaagc ctgggtcctc ggtgaaggtc     60
tcctgcaagg cttctggagg caccttcagc agcaactaca tcagctgggt gcgacaggcc    120
cctggacaag gcttgagtg gatggggatc agccctggca ccggtatcaa cgcatactac    180
gcacagaagt tccagggcag agtcacgatt accgcggacg aatccacgag cacagcctac    240
atggagctga gcagcctgag atctgaggac acggccgtgt attactgtgc gagaagcaag    300
aagggcatgt acgcggctg gacctacccc ctgatgatgt tcgacctgtg gggccagggc    360
accctggtga ccgtgagcag c                                              381

<210> SEQ ID NO 134
<211> LENGTH: 381
<212> TYPE: DNA
<213> ORGANISM: Homo sapiens

<400> SEQUENCE: 134

```
caggtgcagc tggtgcagag cggcgccgag gtgaagaagc ccggcagcag cgtgaaggtg      60
agctgcaagg ccagcggcgg caccttcagc agcaactaca tcagctgggt gcgccaggcc     120
cccggccagg gctggagtg gatgggcatc agccccggca ccggcatcaa cgcctactac     180
gcccagaagt tccagggccg cgtgaccatc accgccgacg agagcaccag caccgcctac     240
atggagctga gcagcctgcg cagcgaggac accgccgtgt actactgcgc cgcagcaag      300
aagggcatgt acggcggctg gacctacccc ctgatgatgt tcgacctgtg gggccagggc     360
accctggtga ccgtgagcag c                                                381
```

<210> SEQ ID NO 135
<211> LENGTH: 381
<212> TYPE: DNA
<213> ORGANISM: Homo sapiens

<400> SEQUENCE: 135

```
caggtgcaat tggttcagtc tggcgcggaa gtgaaaaaac cgggcagcag cgtgaaagtg      60
agctgcaaag cctccggagg cactttttct tctaattata tttcttgggt gcgccaagcc     120
cctgggcagg gtctcgagtg gatgggcatt tctcctggta ctggtattaa tgcttattat     180
gctcagaagt tcagggtcg ggtgaccatt accgcggatg aaagcaccag caccgcgtat     240
atggaactga gcagcctgcg tagcgaagat acggccgtgt attattgcgc gcgttctaag     300
aagggtatgt atggtggttg gacttatcct cttatgatgt ttgatctttg gggccaaggc     360
accctggtga cggttagctc a                                                381
```

<210> SEQ ID NO 136
<211> LENGTH: 324
<212> TYPE: DNA
<213> ORGANISM: Homo sapiens

<400> SEQUENCE: 136

```
gagatcgtgc tgacccagag ccccgccacc ctgagcctga gccccggcga gcgcgccacc      60
ctgagctgcc gcgccagcca gagcgtgagc agcaactacc tggcctggta ccagcagaag     120
cccggccagg ccccccgcct gctgatctac tacgccagcc gccgcgccac cggcgtgccc     180
gcccgcttca gcggcagcgg cagcggcacc gacttcaccc tgaccatcag cagcctggag     240
cccgaggact tcgccgtgta ctactgccag cagaccagca cacccccctt caccttcggc     300
cagggcacca aggtggagat caag                                             324
```

<210> SEQ ID NO 137
<211> LENGTH: 324
<212> TYPE: DNA
<213> ORGANISM: Homo sapiens

<400> SEQUENCE: 137

```
gaaattgtgt tgacacagtc tccagccacc ctgtctttgt ctccagggga aagagccacc      60
ctctcctgca gggccagtca gagtgttagc agcaactact tagcctggta ccaacagaaa     120
cctggccagg ctcccaggct cctcatctat tacgcatccc gcagggccac tggcgtgcca     180
gccaggttca gtggcagtgg gtctgggaca gacttcactc tcaccatcag cagcctagag     240
cctgaagatt ttgcagtttta ttactgtcag cagacttcta atactccttt tacctttggc     300
cagggtacga aagttgaaat taaa                                             324
```

<210> SEQ ID NO 138
<211> LENGTH: 324
<212> TYPE: DNA
<213> ORGANISM: Homo sapiens

<400> SEQUENCE: 138

| | | | | | |
|---|---|---|---|---|---|
| gagatcgtgc | tgacccagag | cccggcgacc | ctgagcctgt | ctccgggcga | acgtgcgacc | 60 |
| ctgagctgca | gagcgagcca | gtctgttcct | tctaattatc | tggcttggta | ccagcagaaa | 120 |
| ccaggtcaag | caccgcgtct | attaatttat | tatgcttctc | gtcgtgcaac | tggggtcccg | 180 |
| gcgcgtttta | gcggctctgg | atccggcacg | gattttaccc | tgaccattag | cagcctggaa | 240 |
| cctgaagact | ttgcggtgta | ttattgccag | cagacttcta | atactccttt | tacctttggc | 300 |
| cagggtacga | aagttgaaat | taaa | | | | 324 |

<210> SEQ ID NO 139
<211> LENGTH: 351
<212> TYPE: DNA
<213> ORGANISM: Homo sapiens

<400> SEQUENCE: 139

| | | | | | |
|---|---|---|---|---|---|
| gaggtgcagc | tggtgcagtc | tggagcagag | gtgaaaaagc | ccggggagtc | tctgaagatc | 60 |
| tcctgtaagg | gttctggata | cagctttagc | aactactgga | tcggctgggt | gcgccagatg | 120 |
| cccgggaaag | gcctggagtg | gatggggatc | atcgacccta | gcaactctta | caccagatac | 180 |
| agcccgtcct | tccaaggcca | ggtcaccatc | tcagccgaca | agtccatcag | caccgcctac | 240 |
| ctgcagtgga | gcagcctgaa | ggcctcggac | accgccatgt | attactgtgc | gagatggtac | 300 |
| tacaagccct | tcgacgtgtg | gggccagggc | accctggtga | ccgtgagcag | c | 351 |

<210> SEQ ID NO 140
<211> LENGTH: 351
<212> TYPE: DNA
<213> ORGANISM: Homo sapiens

<400> SEQUENCE: 140

| | | | | | |
|---|---|---|---|---|---|
| gaggtgcagc | tggtgcagag | cggcgccgag | gtgaagaagc | ccggcgagag | cctgaagatc | 60 |
| agctgcaagg | gcagcggcta | cagcttcagc | aactactgga | tcggctgggt | gcgccagatg | 120 |
| cccggcaagg | gcctggagtg | gatgggcatc | atcgacccca | gcaacagcta | caccgcctac | 180 |
| agccccagct | tccagggcca | ggtgaccatc | agcgccgaca | agagcatcag | caccgcctac | 240 |
| ctgcagtgga | gcagcctgaa | ggccagcgac | accgccatgt | actactgcgc | ccgctggtac | 300 |
| tacaagccct | tcgacgtgtg | gggccagggc | accctggtga | ccgtgagcag | c | 351 |

<210> SEQ ID NO 141
<211> LENGTH: 351
<212> TYPE: DNA
<213> ORGANISM: Homo sapiens

<400> SEQUENCE: 141

| | | | | | |
|---|---|---|---|---|---|
| gaggtgcaat | tggttcagag | cggcgcggaa | gtgaaaaaac | cgggcgaaag | cctgaaaatt | 60 |
| agctgcaaag | gttccggata | ttccttttct | aattattgga | ttggttgggt | gcgccagatg | 120 |
| cctgggaagg | gtctcgagtg | gatgggcatt | atcgatccgt | ctaatagcta | tacccgctat | 180 |
| tctccgagct | ttcagggcca | ggtgaccatt | agcgcggata | aaagcattag | caccgcgtat | 240 |
| cttcaatgga | gcagcctgaa | agcgagcgat | acggccatgt | attattgcgc | gcgttggtat | 300 |
| tataagccctt | tgatgtttg | gggccaaggc | accctggtga | cggttagctc | a | 351 |

<210> SEQ ID NO 142
<211> LENGTH: 336
<212> TYPE: DNA
<213> ORGANISM: Homo sapiens

<400> SEQUENCE: 142
cagtctgtgc tgacgcagcc gccctcagtg tctggggccc cagggcagag ggtcaccatc    60
tcctgcactg ggagcagctc caacatcggg agcggttatg atgtacactg gtaccagcag   120
cttccaggaa cagcccccaa actcctcatc tatggtaaca gcaagcggcc ctcaggggtc   180
cctgaccgat tctctggctc caagtctggc acctcagcct ccctggccat cactgggctc   240
cagagcgagg atgaggctga ttattactgc gccagctgga ccgacggcct gagcctggtg   300
gtgttcggcg gcggcaccaa gctgaccgtg ctgggc                              336

<210> SEQ ID NO 143
<211> LENGTH: 336
<212> TYPE: DNA
<213> ORGANISM: Homo sapiens

<400> SEQUENCE: 143
cagagcgtgc tgacccagcc ccccagcgtg agcggcgccc ccggccagcg cgtgaccatc    60
agctgcaccg gcagcagcag caacatcggc agcggctacg acgtgcactg gtaccagcag   120
ctgcccggca ccgcccccaa gctgctgatc tacggcaaca gcaagcgccc cagcggcgtg   180
cccgaccgct tcagcggcag caagagcggc accagcgcca gcctggccat caccggcctc   240
cagagcgagg acgaggccga ctactactgt gccagctgga ccgacggcct gagcctggtg   300
gtgttcggcg gcggcaccaa gctgaccgtg ctgggc                              336

<210> SEQ ID NO 144
<211> LENGTH: 336
<212> TYPE: DNA
<213> ORGANISM: Homo sapiens

<400> SEQUENCE: 144
cagagcgtgc tgacccagcc gccttcagtg agtggcgcac aggtcagcg tgtgaccatc    60 tcgtgtacgg gcagcagcag caacattggt tctggttatg atgtgcattg gtaccagcag   120
ttgcccggga cggcgccgaa acttctgatt tatggtaatt ctaagcgtcc ctcaggcgtg   180
ccggatcgtt ttagcggatc caaaagcggc accagcgcga ccttgcgat acgggcctg    240 caaagcgaag acgaagcgga ttattattgc gcttcttgga ctgatggtct ttctcttgtt   300
gtgtttggcg gcggcacgaa gttaaccgtt cttggc                              336

<210> SEQ ID NO 145
<211> LENGTH: 189
<212> TYPE: PRT
<213> ORGANISM: Homo sapiens

<400> SEQUENCE: 145

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr

```
                 50                  55                  60
Thr Asn Asp Val Pro His Ile Gln Cys Gly Asp Gly Cys Asp Pro Gln
 65                  70                  75                  80

Gly Leu Arg Asp Asn Ser Gln Phe Cys Leu Gln Arg Ile His Gln Gly
                     85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Ala Gln Leu His Ala Ser Leu
            115                 120                 125

Leu Gly Leu Ser Gln Leu Leu Gln Pro Glu Gly His His Trp Glu Thr
        130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 146
<211> LENGTH: 19
<212> TYPE: PRT
<213> ORGANISM: Homo sapiens

<400> SEQUENCE: 146

```
Asn Ile Glu His Lys Tyr Leu Gly Tyr Ala Thr Ser Tyr Ala Ala Ser
  1               5                  10                  15

Val Lys Gly
```

<210> SEQ ID NO 147
<211> LENGTH: 123
<212> TYPE: PRT
<213> ORGANISM: Homo sapiens

<400> SEQUENCE: 147

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Asn Ile Glu His Lys Tyr Leu Gly Tyr Ala Thr Ser Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120
```

<210> SEQ ID NO 148
<211> LENGTH: 12
<212> TYPE: PRT
<213> ORGANISM: Homo sapiens

```
<400> SEQUENCE: 148

His Gln Gly Leu Ile Phe Tyr Glu Lys Leu Leu Gly
1               5                   10
```